(12) United States Patent
Lee et al.

(10) Patent No.: US 9,125,580 B2
(45) Date of Patent: Sep. 8, 2015

(54) ELECTROCARDIOGRAPHY SIGNAL EXTRACTION METHOD

(71) Applicant: NATIONAL CHENG KUNG UNIVERSITY, Tainan (TW)

(72) Inventors: Gwo Giun Lee, Tainan (TW); Jhen-Yue Hu, Tainan (TW); Chun-Fu Chen, Tainan (TW); Jhu-Syuan Ho, Tainan (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 0 days.

(21) Appl. No.: 14/020,429

(22) Filed: Sep. 6, 2013

(65) Prior Publication Data
US 2015/0045681 A1 Feb. 12, 2015

(30) Foreign Application Priority Data
Aug. 7, 2013 (TW) .............................. 102128332 A

(51) Int. Cl.
*A61B 5/0452* (2006.01)
*A61B 5/00* (2006.01)
*A61B 5/0456* (2006.01)

(52) U.S. Cl.
CPC .............. *A61B 5/0452* (2013.01); *A61B 5/0456* (2013.01); *A61B 5/7203* (2013.01)

(58) Field of Classification Search
None
See application file for complete search history.

(56) References Cited

U.S. PATENT DOCUMENTS 7,818,049 B2   10/2010  Halperin et al.
8,332,023 B2   12/2012  Frank et al.

OTHER PUBLICATIONS

Gabor Feature Extraction for Electrocardiogram Signals, Lin et al., Biomedical Circuits and Systems Conferences, pp. 304-307, Nov. 28-30, 2012.*
Detection and classification of P Waves Using Gabor Wavelets, Sommer et al., IEEE Computers in Cardiology pp. 531-534, Sep. 5-8, 1993.*

* cited by examiner

*Primary Examiner* — Paula J Stice
(74) *Attorney, Agent, or Firm* — WPAT, P.C.; Anthony King

(57) ABSTRACT

An electrocardiography signal extraction method is performed on a processor of a computer system and includes receiving an electrocardiography signal, performing a time-frequency transformation on the received electrocardiography signal to generate a corresponding scalogram, selecting a predetermined R-pertinent scale, performing the time-frequency transformation at the selected predetermined R-pertinent scale to generate a R-pertinent summarized response, obtaining a R peak position, selecting a predetermined QRS-pertinent scale, performing the time-frequency transformation at the selected predetermined QRS-pertinent scale, obtaining a Q peak position and a S peak position of the electrocardiography signal by finding relative maximum negative responses before and behind the R peak position respectively, obtaining a QRSon position and a QRSoff position by finding relative minimum second derivatives of the responses before the Q peak position and behind the S peak position, respectively.

11 Claims, 52 Drawing Sheets
(9 of 52 Drawing Sheet(s) Filed in Color)

ELECTROCARDIOGRAPHY SIGNAL EXTRACTION METHOD

BACKGROUND OF THE INVENTION

1. Field of the Invention

The present disclosure generally relates to an electrocardiography (ECG) signal extraction method and, more particularly, to an ECG signal extraction method which can avoid the effect of the baseline drift without the baseline drift removal.

2. Description of the Related Art

Electrocardiography (ECG) is a transthoracic interpretation of the electrical activity of the heart over a period of time, as detected by electrodes attached to the surface of the skin and recorded by a device external to the body.

Baseline drift in ECG signal is the biggest hurdle in visualization of correct waveform and computerized detection of wave complexes based on threshold decision. The baseline drift may be linear, static, nonlinear or wavering. Reducing the baseline drift to a near zero value greatly helps in visually inspecting the morphology of the wave components as well as in computerized detection and delineation of the wave complexes. FIG. 1 shows a traditional ECG signal extraction method, which bears a baseline drift removal step.

SUMMARY OF THE INVENTION

The objective of this disclosure is to avoid the effect of the baseline drift without a baseline drift removal.

Another objective of this disclosure is to accomplish an accurately detecting to find a waveform similarity between each wave in ECG signals and corresponding bases.

A further objective of this disclosure is to extract accurate features for clinical use but omitting the step of baseline drift removal.

In an embodiment, an electrocardiography signal extraction method comprises receiving an electrocardiography signal, performing a time-frequency transformation on the received electrocardiography signal to generate a corresponding scalogram, selecting a pre-defined R-pertinent scale for the corresponding scalogram, performing the time-frequency transformation on the corresponding scalogram at the selected pre-defined R-pertinent scale to generate a R-pertinent summarized response, obtaining a R peak position of the electrocardiography signal by finding relative maximum responses on the R-pertinent summarized response, selecting a pre-defined QRS-pertinent scale for the corresponding scalogram, performing the time-frequency transformation on the corresponding scalogram at the selected pre-defined QRS-pertinent scale to generate a QRS-pertinent transferred response, obtaining a Q peak position of the electrocardiography signal by finding relative maximum negative responses before the R peak position, obtaining a S peak position of the electrocardiography signal by finding relative maximum negative responses behind the R peak position, obtaining a QRSon position of the electrocardiography signal by finding relative minimum second derivatives of the responses before the Q peak position, and obtaining a QRSoff position of the electrocardiography signal by finding relative minimum second derivatives of the responses behind the S peak position.

In a form shown, the time-frequency transformation comprises Continuous Wavelet Transform with Gabor mother wavelet.

In the form shown, the pre-defined R-pertinent scale comprises three pre-defined R-pertinent scales.

In the form shown, the electrocardiography signal extraction method further comprises de-noising the wave before performing the time-frequency transformation, selecting a pre-defined P-pertinent scale for the corresponding scalogram, performing the time-frequency transformation on the corresponding scalogram at the selected pre-defined P-pertinent scale to generate a P-pertinent transferred response, obtaining a P peak position of the electrocardiography signal by finding relative maximum responses before the R peak position, selecting a pre-defined T-pertinent scale for the corresponding scalogram, performing the time-frequency transformation on the corresponding scalogram at the selected pre-defined T-pertinent scale to generate a T-pertinent transferred response, and obtaining a T peak position of the electrocardiography signal by finding relative maximum responses behind the R peak position.

In the form shown, the electrocardiography signal extraction method further comprises detecting a P wave of the electrocardiography signal by the P peak position, separating the P wave into a left wave and a right wave, normalizing the left wave and a plurality of scales of Gaussian, comparing the normalized left wave with a left part of the normalized scales of Gaussian, acquiring a left part error function, indicating a left minimum comparative error, selecting a left scale of Gaussian with the left minimum comparative error, obtaining a left duration of the P wave according to the selected left scale of Gaussian, obtaining a Pon by the left duration, normalizing the right wave, comparing the normalized right wave with a right part of the normalized scales of Gaussian, acquiring a right part error function, indicating a right minimum comparative error, selecting a right scale of Gaussian with the right minimum comparative error, obtaining a right duration of the P wave according to the selected right scale of Gaussian, obtaining a Poff by the right duration and the P peak position, and obtaining an extracted P wave.

In the form shown, the electrocardiography signal extraction method further comprises detecting a T wave of the electrocardiography signal by the T peak position, separating the T wave into a left wave and a right wave, normalizing the left wave and a plurality of scales of Gaussian, comparing the normalized left wave with a left part of the normalized scales of Gaussian, acquiring a left part error function, indicating a left minimum comparative error, selecting a left scale of Gaussian with the left minimum comparative error, obtaining a left duration of the T wave according to the selected left scale of Gaussian, obtaining a Ton by the left duration, normalizing the right wave, comparing the normalized right wave with a right part of the normalized scales of Gaussian, acquiring a right part error function, indicating a right minimum comparative error, selecting a right scale of Gaussian with the right minimum comparative error, obtaining a right duration of the T wave according to the selected right scale of Gaussian, obtaining a Toff by the right duration, and obtaining an extracted T wave.

In the form shown, the electrocardiography signal extraction method further comprises de-noising the wave before or after performing the time-frequency transformation.

In the form shown, the electrocardiography signal extraction method further comprises estimating a R amplitude by calculating a difference between the R peak and a linear interpolation line connected between QRSon and QRSoff, estimating a Q depth by calculating a difference between the Q peak and QRSon, and estimating a S depth by calculating a difference between the Q peak and QRSoff.

In the form shown, the electrocardiography signal extraction method further comprises estimating a P amplitude by calculating a difference between the P peak and a linear interpolation line connected between Pon and Poff.

In the form shown, the electrocardiography signal extraction method further comprises estimating a T amplitude by calculating a difference between the T peak and a linear interpolation line connected between Ton and Toff.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present disclosure will become more fully understood from the detailed description given hereinafter and the accompanying drawings which are given by way of illustration only, and thus are not limitative of the present invention, and wherein.

Figure 1:
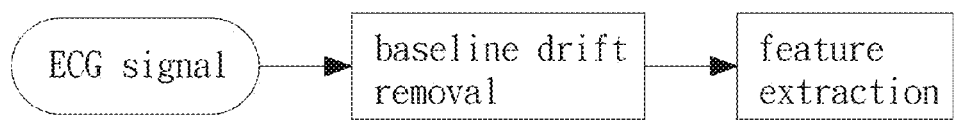
FIG. 1 shows a traditional ECG signal extraction method, which bears a baseline drift removal step.

In the various figures of the drawings, the same numerals designate the same or similar parts. Furthermore, when the terms "first", "second", "third", "fourth", "inner", "outer", "top", "bottom", "front", "rear" and similar terms are used hereinafter, it should be understood that these terms have reference only to the structure shown in the drawings as it would appear to a person viewing the drawings, and are utilized only to facilitate describing the invention.

DETAILED DESCRIPTION OF THE INVENTION

Figure 2:
FIG. 2 shows the spirit of the ECG signal extraction method of the present disclosure, which does not need a baseline drift removal step.
Figure 3A:
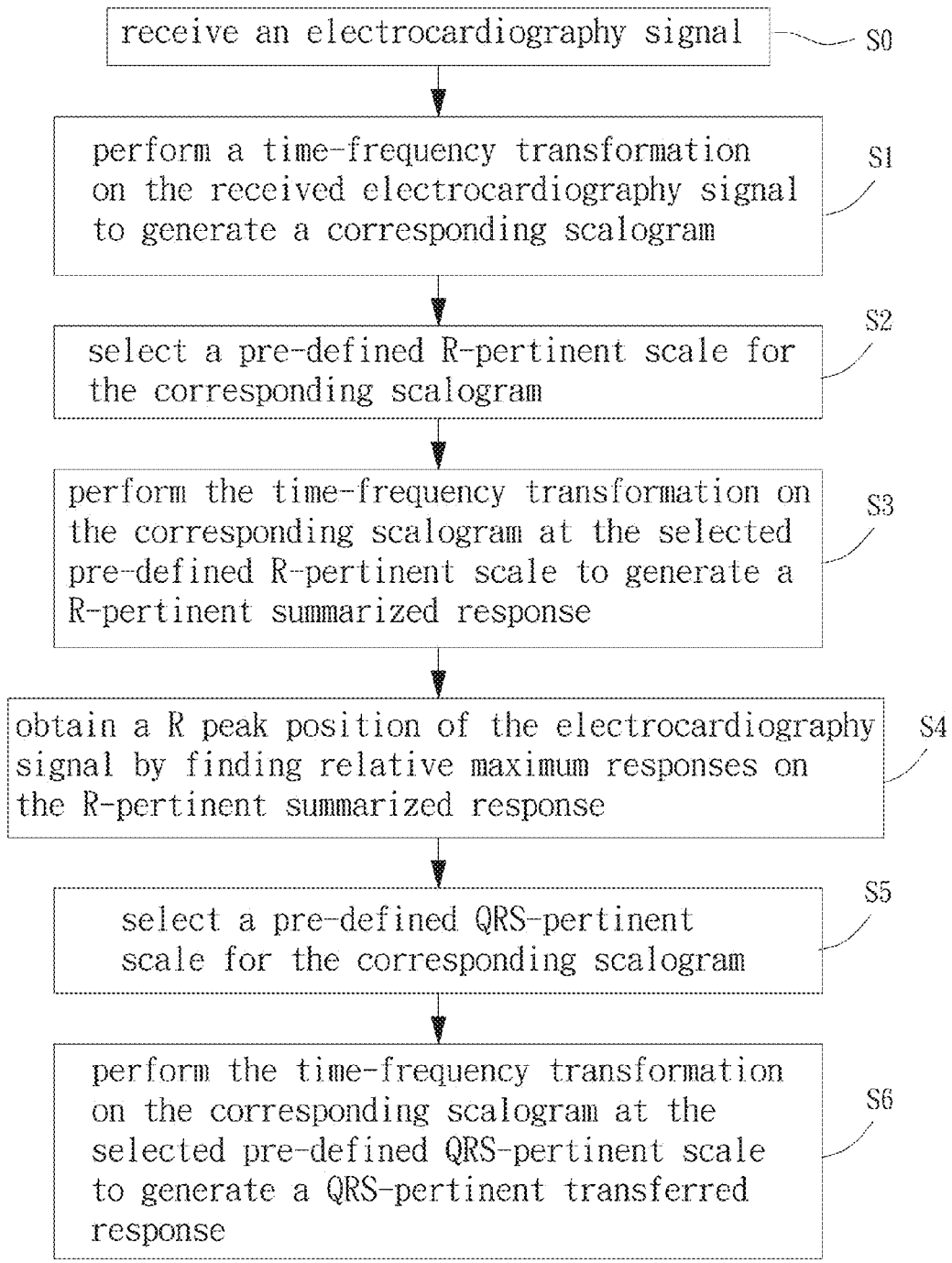
FIGS. 3a and 3b show the general idea of the ECG signal extraction method of the present disclosure.
Figure 3B:
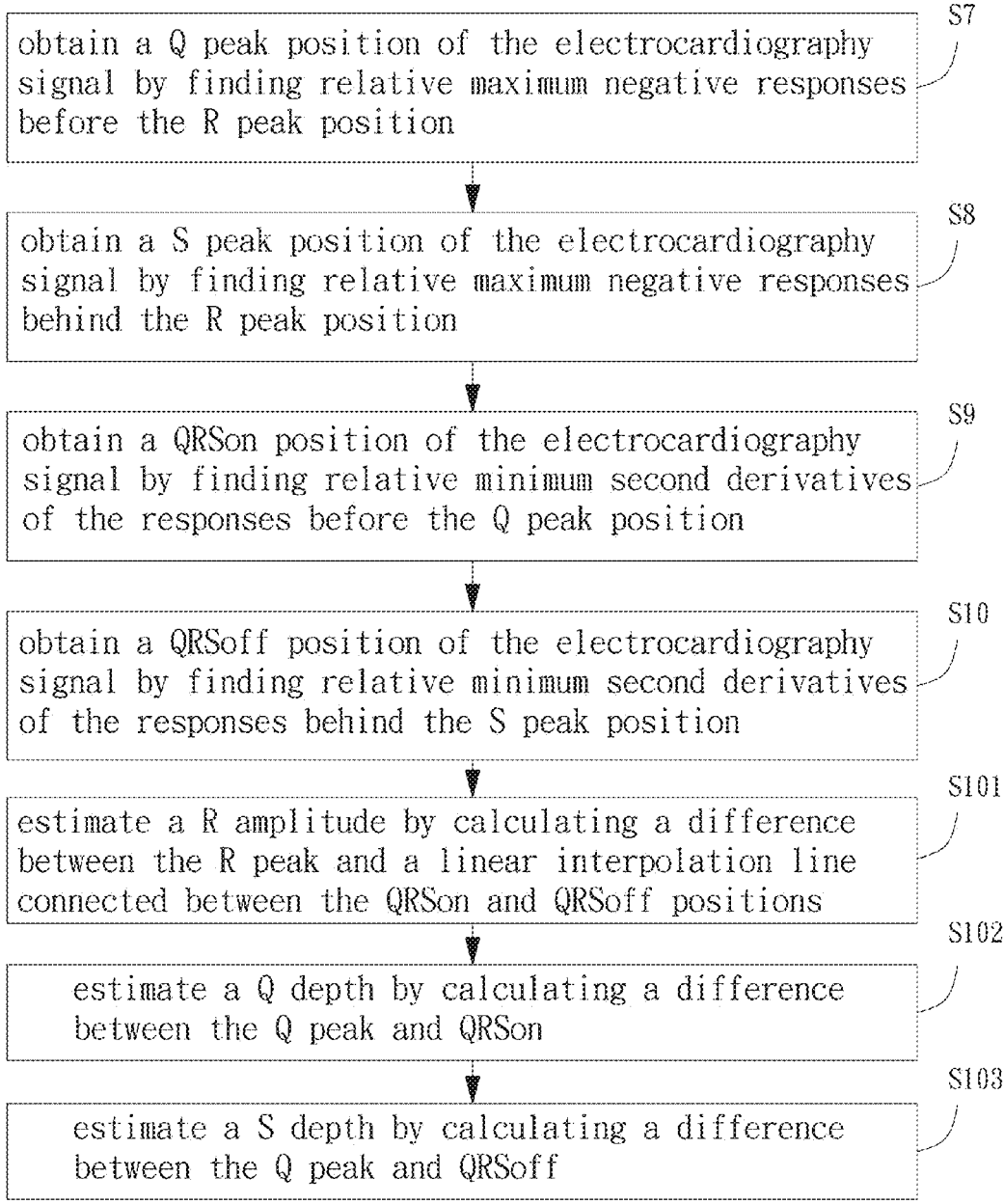
Figure 30:
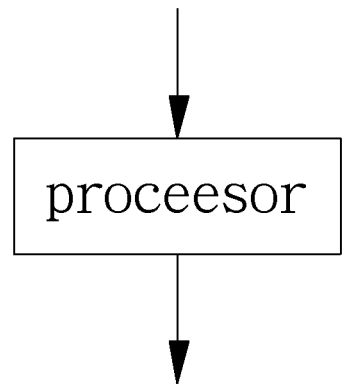
FIG. 30 shows a processor used to receive an electrocardiography signal and to output the extracted features.

The spirit of the ECG signal extraction method of this disclosure is presented in FIG. 2, which shows the present disclosure does not need a baseline drift removal to extract ECG signals. FIG. 3a is the general idea of the ECG signal extraction method of the present disclosure, wherein the sequence therein does not limit the method of this disclosure. FIG. 3b shows an embodiment of FIG. 3a. FIG. 30 shows that the ECG signal is received by a processor of a computer system, wherein the claimed ECG signal extraction method of the present disclosure is performed by the processor, and the clinically useful features are therefore produced by the processor. The clinically useful features, for example. includes R peak position, Q peak position, S peek position, QRSon position, QRSoff position, P peak position, T peak position of the electrocardiography signal, etc.

FIG. 3 shows further details of this disclosure, including receiving an electrocardiography signal (S0), performing a time-frequency transformation on the received electrocardiography signal to generate a corresponding scalogram (S1), selecting a pre-defined R-pertinent scale for the corresponding scalogram (S2), performing the time-frequency transformation on the corresponding scalogram at the selected pre-defined R-pertinent scale to generate a R-pertinent summarized response (S3), obtaining a R peak position of the electrocardiography signal by finding relative maximum responses on the R-pertinent summarized response (S4), selecting a pre-defined QRS-pertinent scale for the corresponding scalogram (S5), performing the time-frequency transformation on the corresponding scalogram at the selected pre-defined QRS-pertinent scale to generate a QRS-pertinent transferred response (S6), obtaining a Q peak position of the electrocardiography signal by finding relative maximum negative responses before the R peak position (S7), obtaining a S peak position of the electrocardiography signal by finding relative maximum negative responses behind the R peak position (S8), obtaining a QRSon position of the electrocardiography signal by finding relative minimum second derivatives of the responses before the Q peak position (S9), and obtaining a QRSoff position of the electrocardiography signal by finding relative minimum second derivatives of the responses behind the S peak position (S10). The ECG signal extraction method of the disclosure may further include estimating a R amplitude by calculating a difference between the R peak and a linear interpolation line connected between QRSon and QRSoff (S101), estimating a Q depth by calculating a difference between the Q peak and QRSon (S102), and estimating a S depth by calculating a difference between the Q peak and QRSoff (S103).

Figure 4:
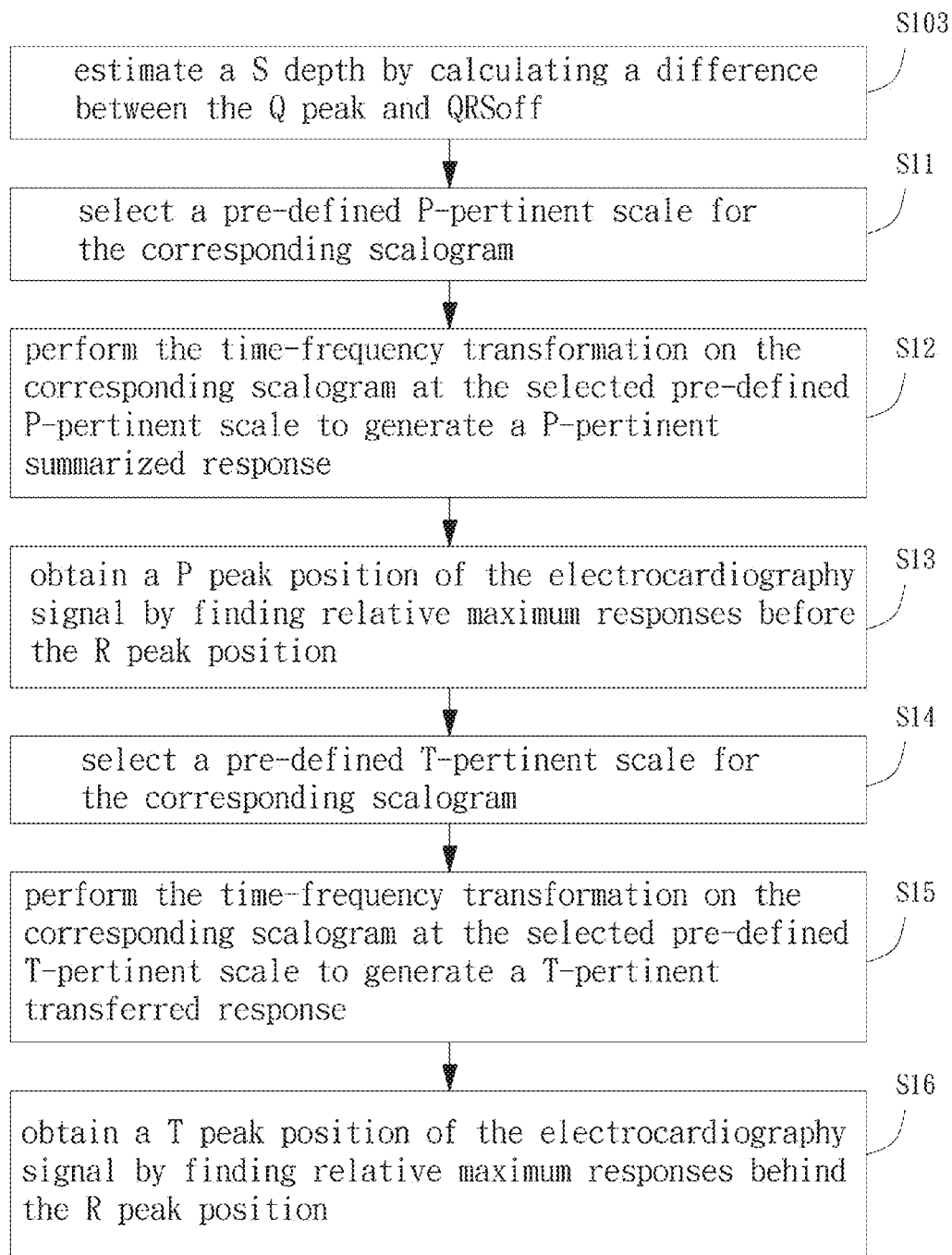
FIG. 4 shows further steps of the general idea of the ECG signal extraction method of the present disclosure.

Referring to FIG. 4, the ECG signal extraction method of the disclosure may further comprise selecting a pre-defined P-pertinent scale for the corresponding scalogram (S11), performing the time-frequency transformation on the corresponding scalogram at the selected pre-defined P-pertinent scale to generate a P-pertinent summarized response (S12), obtaining a P peak position of the electrocardiography signal by finding relative maximum responses before the R peak position (S13), selecting a pre-defined T-pertinent scale for the corresponding scalogram (S14), performing the time-frequency transformation on the corresponding scalogram at the selected pre-defined T-pertinent scale to generate a T-pertinent transferred response (S15), and obtaining a T peak position of the electrocardiography signal by finding relative maximum responses behind the R peak positions (S16).

Figure 5:
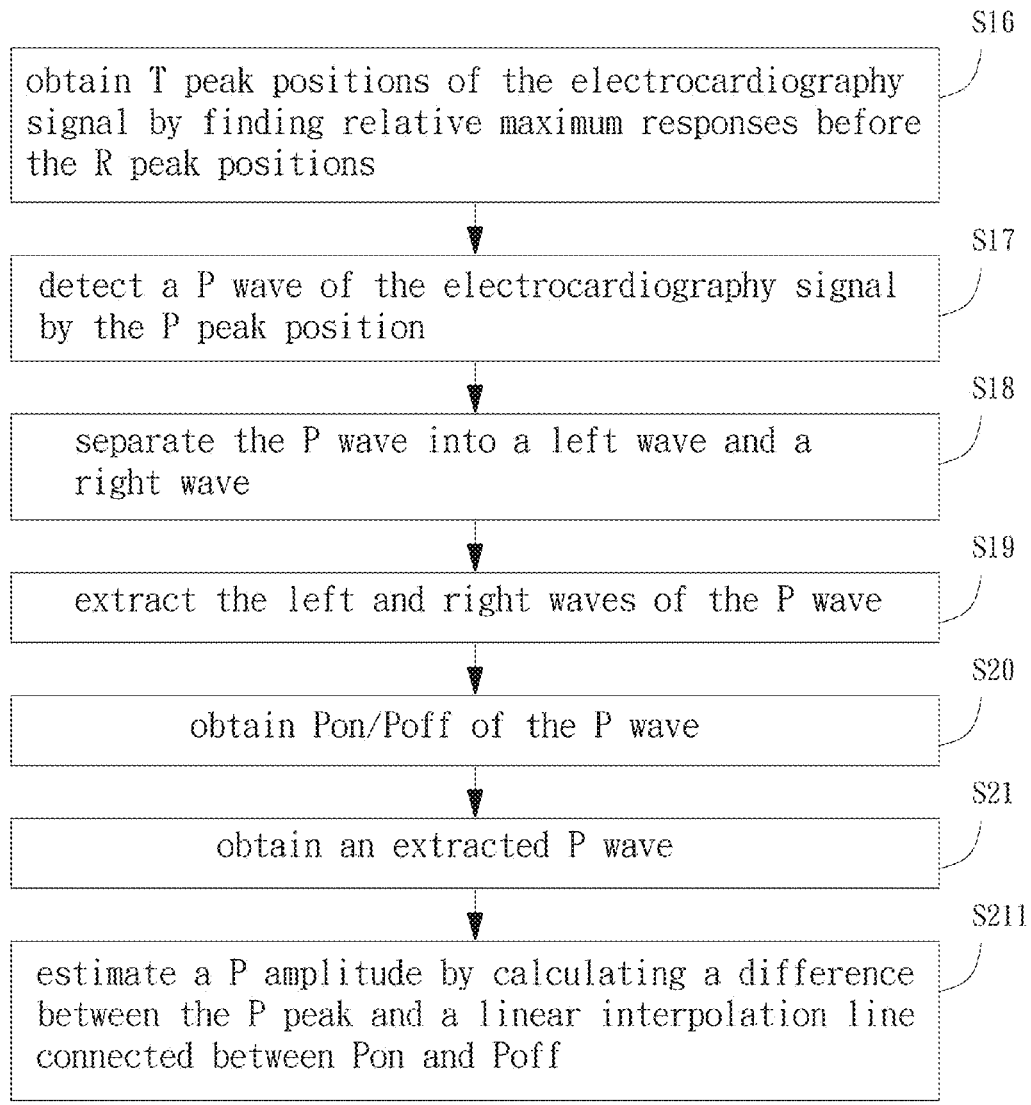
FIG. 5 shows yet further steps of the general idea of the ECG signal extraction method of the present disclosure.
Figure 6:
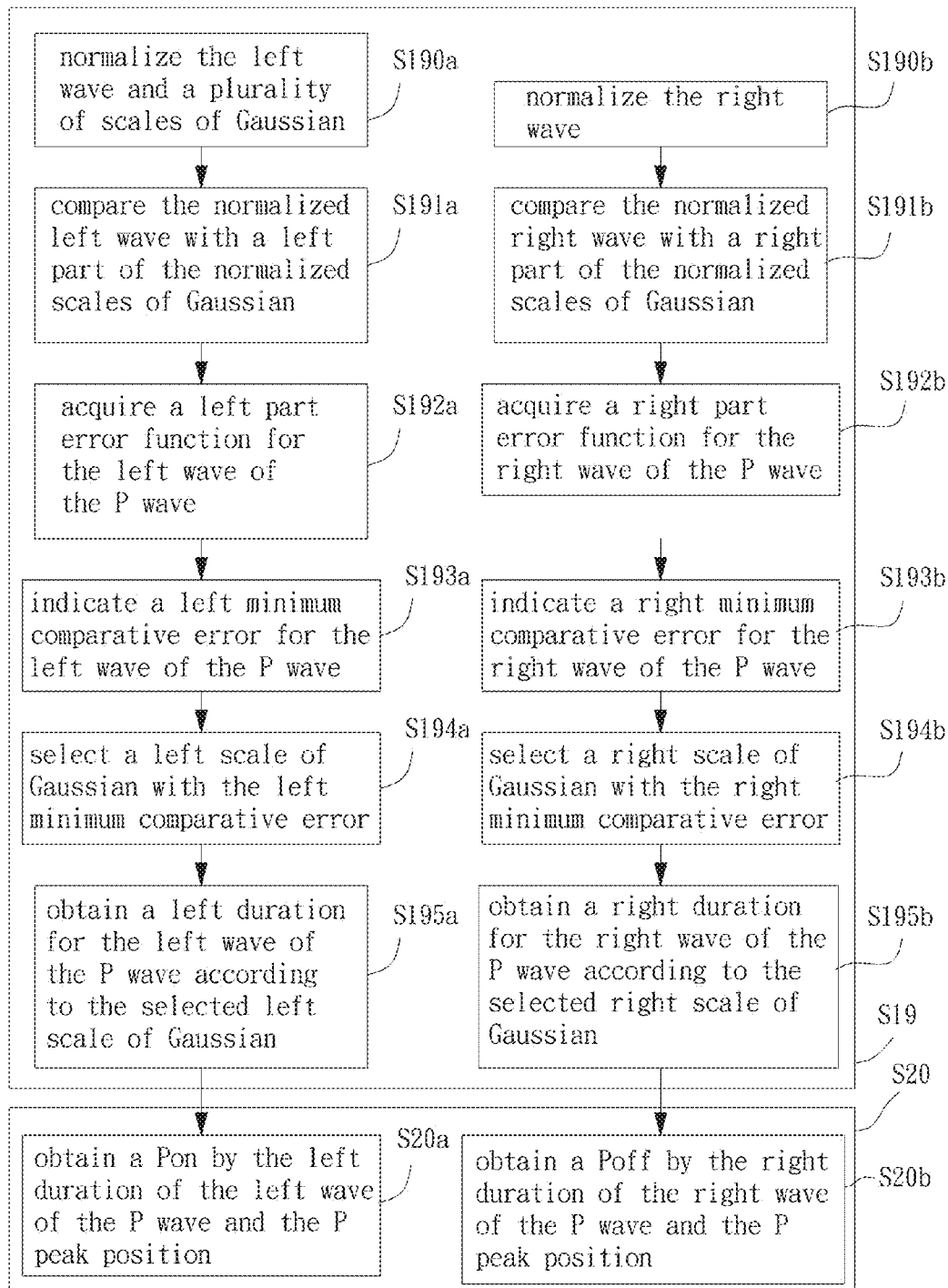
FIG. 6 shows detailed flowcharts of the steps S19 and S20.

Referring to FIG. 5, the ECG signal extraction method may further include detecting a P wave of the electrocardiography signal by the P peak position (S17), separating the P wave into a left wave and a right wave (S18), extracting the left and right waves of the P wave (S19), obtaining Pon/Poff of the P wave (S20) and obtaining an extracted P wave (S21). Referring to FIG. 6, the step S19 may comprise a left extraction step (S19a) and a right extraction step (S19b). The left extraction step may comprise normalizing the left wave and a plurality of scales of Gaussian (S190a), comparing the normalized left wave with a left part of the normalized scales of Gaussian (S191a), acquiring a left part error function for the left wave of the P wave (S192a), indicating a left minimum comparative error for the left wave of the P wave (S193a), selecting a left scale of Gaussian with the left minimum comparative error (S194a), and obtaining a left duration for the left wave of the P wave according to the selected left scale of Gaussian (S195a). Similarly, the right extraction step may comprise normalizing the right wave (S190b), comparing the normalized right wave with a right part of the normalized scales of Gaussian (S191b), acquiring a right part error function for the right wave of the P wave (S192b), indicating a right minimum comparative error for the right wave of the P wave (S193b), selecting a right scale of Gaussian with the right minimum comparative error (S194b), and obtaining a right duration for the right wave of the P wave according to the selected right scale of Gaussian (S195b). The step S20 may comprise obtaining a Pon by the left duration of the left wave of the P wave and the P peak position (S20a) following the left extraction step, as well as obtaining a Poff by the right duration of the right wave of the P wave and the P peak position (S20b) following the right extraction step. The ECG signal extraction method of the disclosure may further include estimating a P amplitude by calculating a difference between the P peak and a linear interpolation line connected between Pon and Poff (S211).

Figure 7:
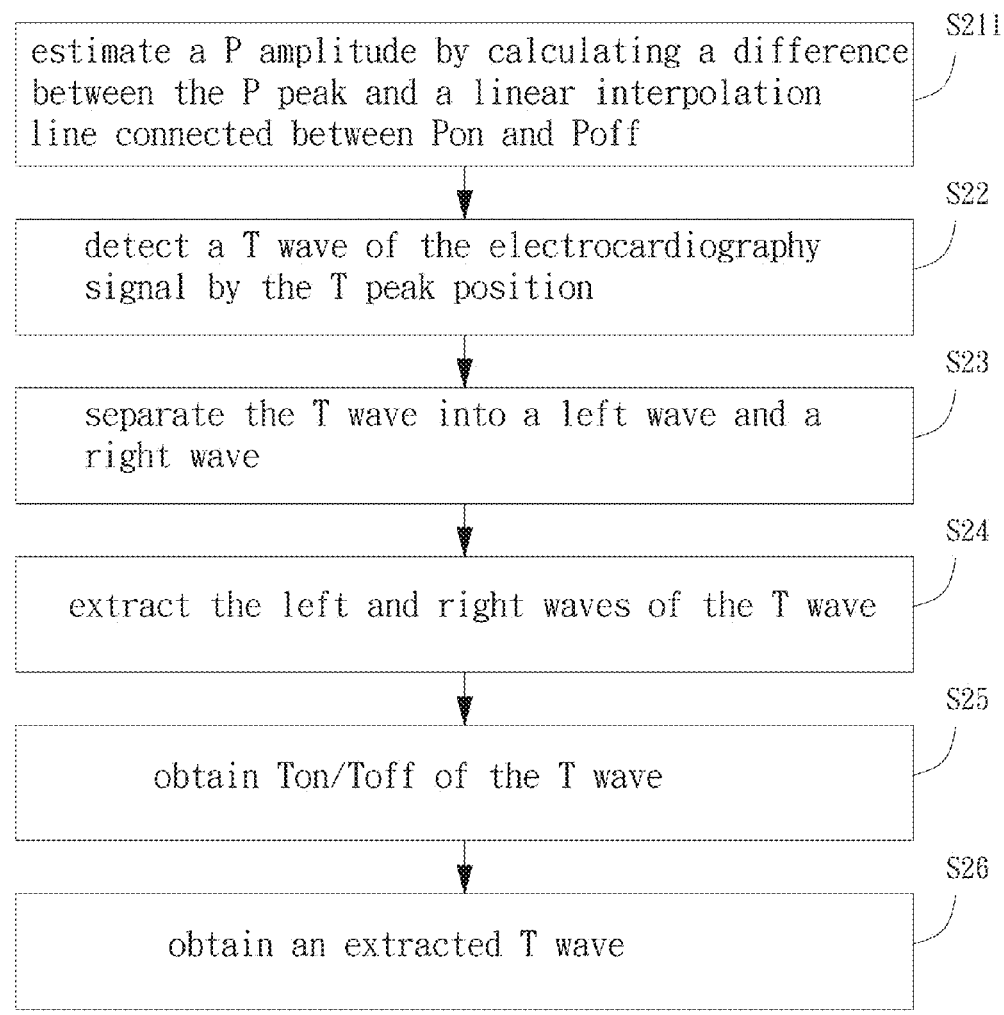
FIG. 7 shows yet further steps of the general idea of the ECG signal extraction method of the present disclosure.
Figure 8:
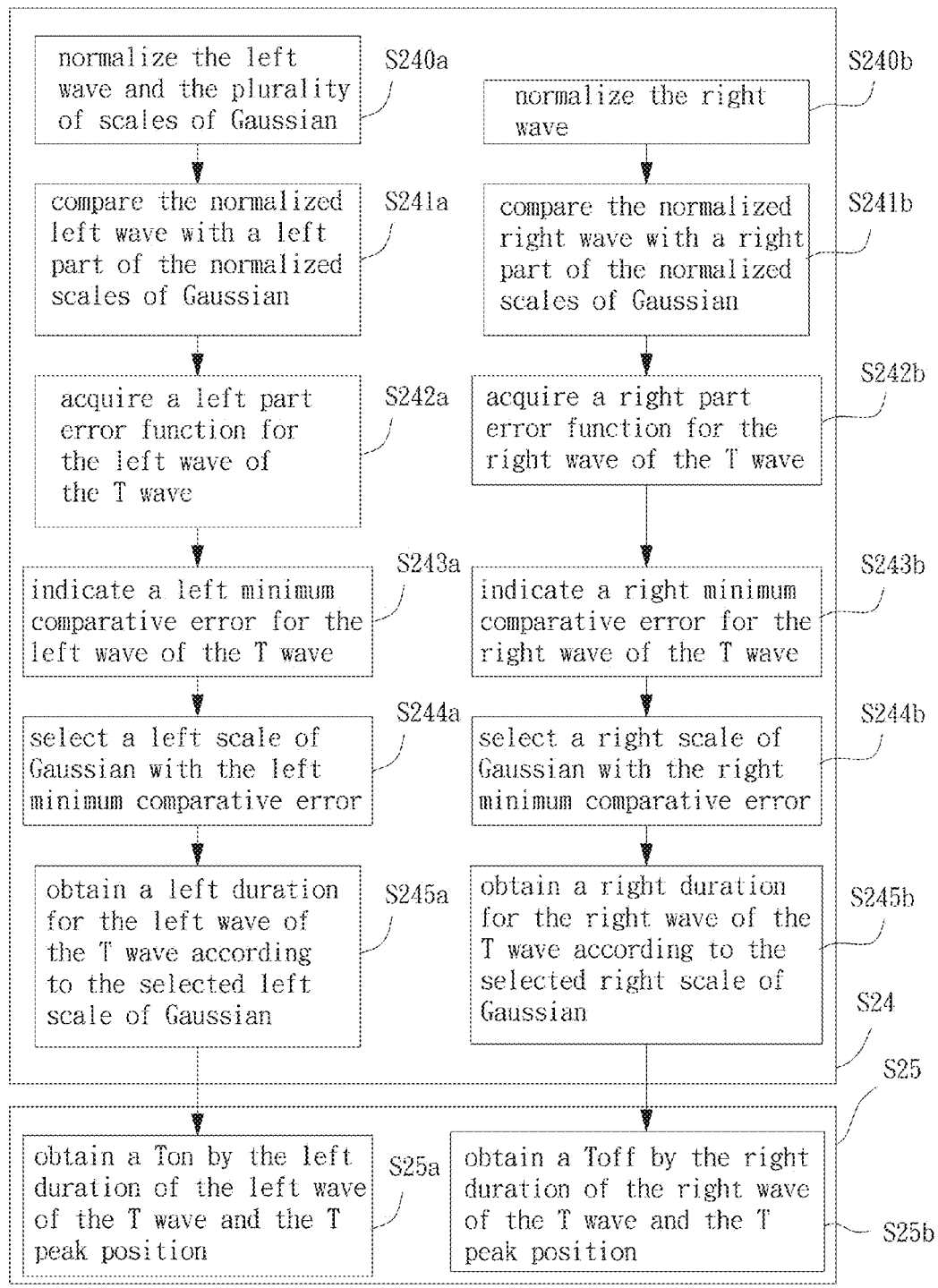
FIG. 8 detailed flowcharts of the steps S24 and S25.

Referring to FIG. 7, the ECG signal extraction method may further include detecting a T wave of the electrocardiography signal by the T peak position (S22), separating the T wave into a left wave and a right wave (S23), extracting the left and right waves of the T wave (S24), obtaining Ton/Toff of the T wave (S25) and obtaining an extracted T wave (S26). Referring to FIG. 8, the step S24 may comprise a left extraction step (S24a) and a right extraction step (S24b). The left extraction step may comprise normalizing the left wave of the T wave and the plurality of scales of Gaussian (S240a), comparing the normalized left wave with a left part of the normalized scales of Gaussian (S241a), acquiring a left part error function for the left wave of the T wave (S242a), indicating a left minimum comparative error for the left wave of the T wave (S243a), selecting a left scale of Gaussian with the left minimum comparative error (S244a), obtaining a left duration of the left wave of the T wave according to the selected left scale of Gaussian (S245a). Similarly, the right extraction step may comprise normalizing the right wave of the T wave (S240b), comparing the normalized right wave with a right part of the normalized scales of Gaussian (S241b), acquiring a right part error function for the right wave of the T wave (S242b), indicating a right minimum comparative error for the right wave of the T wave (S243b), selecting a right scale of Gaussian with the right minimum comparative error (S244b), obtaining a right duration of the right wave of the T wave according to the selected right scale of Gaussian (S245b). The step S25 may comprise obtaining a Ton by the left duration of the left wave of the T wave and the T peak position (S25a) following the left extraction step, as well as obtaining a Toff by the right duration of the right wave of the T wave and the T peak position (S25b) following the right extraction step. The ECG signal extraction method of the disclosure may further include estimating a T amplitude by calculating a difference between the T peak and a linear interpolation line connected between Ton and Toff (S361).

Figure 9:
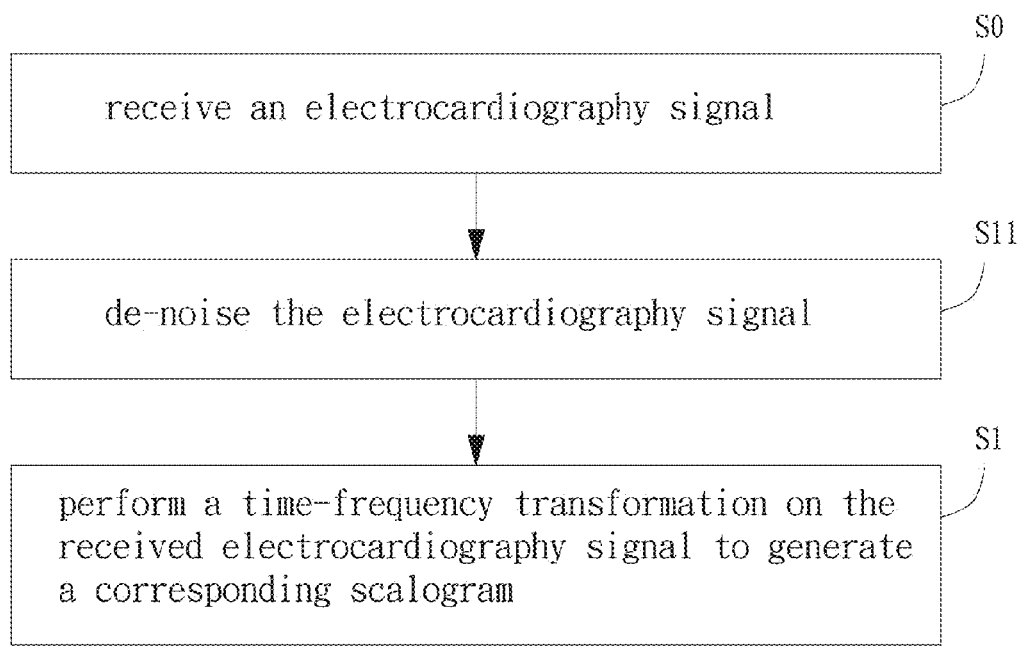
FIG. 9 shows a de-noising step performed after the step S0.

Referring to FIG. 9, for a better extracting effect, de-noising the electrocardiography signal (S11) may be processed before performing the time-frequency transformation (S1). However, de-noising the electrocardiography signal (S11) may also be processed after performing the time-frequency transformation (S1). Therefore, the method of this disclosure can avoid the effect of the baseline drift without a baseline drift removal. Namely, this disclosure can accomplish an accurate detection to find a waveform similarity between each wave in ECG signals and corresponding bases, and extract accurate features for clinical use while omitting the step of baseline drift removal.

In comparison with the conventional ECG signal extraction method, the advantages of the ECG signal extraction method of this disclosure include extracting features accurately from the received ECG signal and omitting the procedure of "baseline drift removal". The accurate detections are achieved by finding the waveform similarity between each wave in the ECG signals and the corresponding bases. The concepts to omit the step of "baseline drift removal" without being affected by the baseline drift make it possible to prevent filtering the affected frequency band of the baseline drift as well as detecting the onsets and offsets independently.

Based on the concepts of this disclosure, this ECG signal extraction method may utilize CWT with Gabor wavelet as well as the matching process using Gaussian models with a plurality of scales (MPGMVS) for extracting the features within QRS complex and P, T peak detections as well as Pon, Poff, Ton, Toff detections, respectively.

For a better understanding, an embodiment is explained with the following description.

Embodiment of ECG Signal Extraction System

Figure 10:
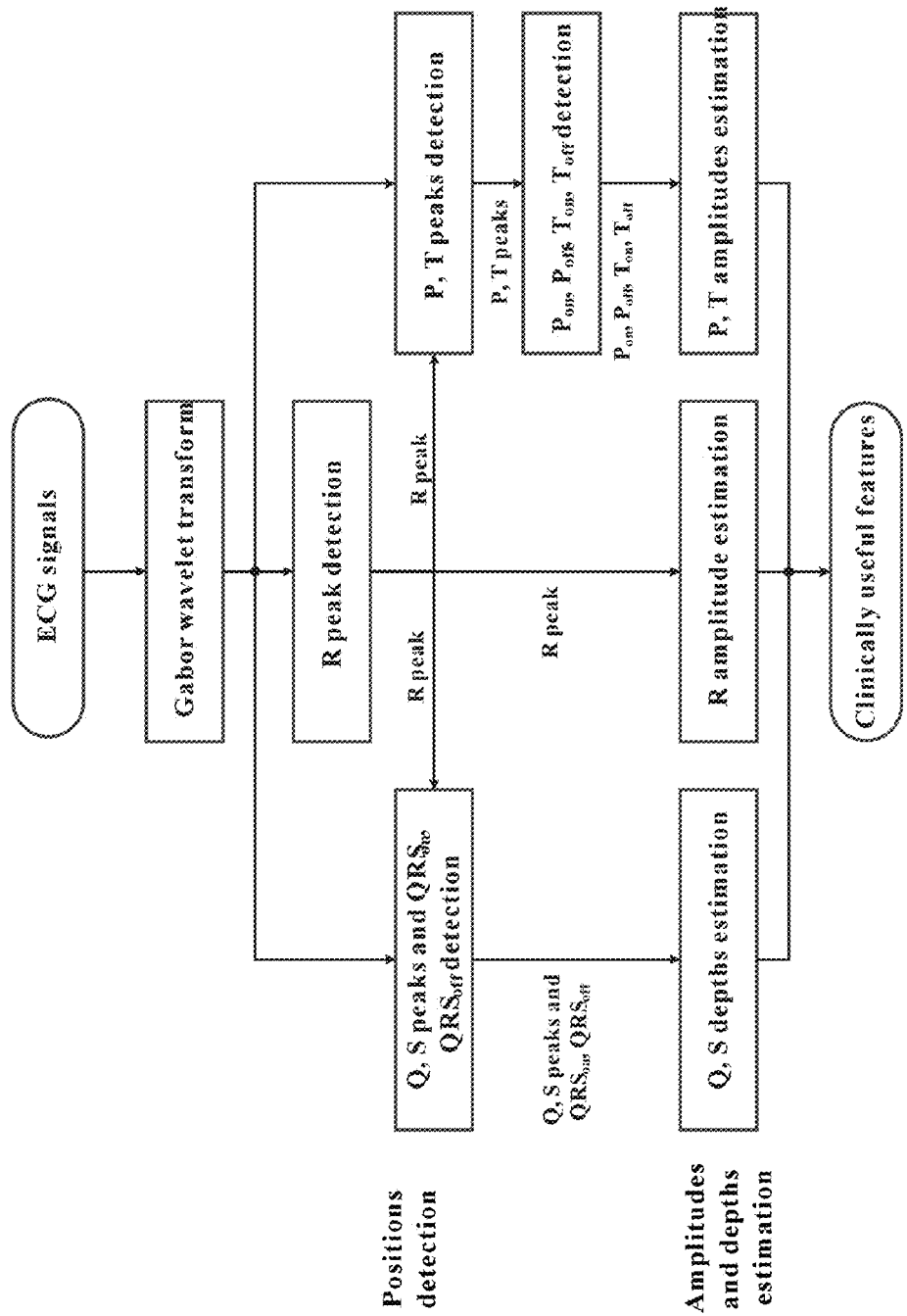
FIG. 10 shows an embodiment of a full ECG signal extraction of the present disclosure.

FIG. 10 shows an embodiment of a full ECG signal extraction of the present disclosure. The embodiment may be separated into two parts. First part is the position detections containing R peak detection, Q, S peak and QRSon, QRSoff detections, P, T peak detections, and Pon, Poff, Ton, Toff detections. Second part is the amplitude and depth estimations including R amplitude, Q, S depth, and P, T amplitude estimations.

In the first part, the position detection may first be performed by detecting the peak of the wave of the ECG signal, and the detecting may include performing a time-frequency transformation on the received electrocardiography signal, e.g. CWT with Gabor wavelet is performed. Here, the Continuous Wavelet Transform (CWT) with Gabor mother wavelet (Gabor Wavelet Transform, GWT) may be a better embodiment.

Next, the R peak may be detected by obtaining the R peak by finding a maximum voltage. Then, the Q, S peaks and QRSon, QRSoff and P, T peaks may be detected. Namely, the P peak may be obtained by finding a first maximum voltage before the R peak, or the T peak may be obtained by finding a first maximum voltage behind the R peak. Finally, Pon, Poff, Ton, and Toff are extracted.

In the second part, for the amplitude/depth estimations, R amplitude estimation, Q, S depth estimations, and P, T amplitude estimations may be performed at the same time.

Figure 11A:
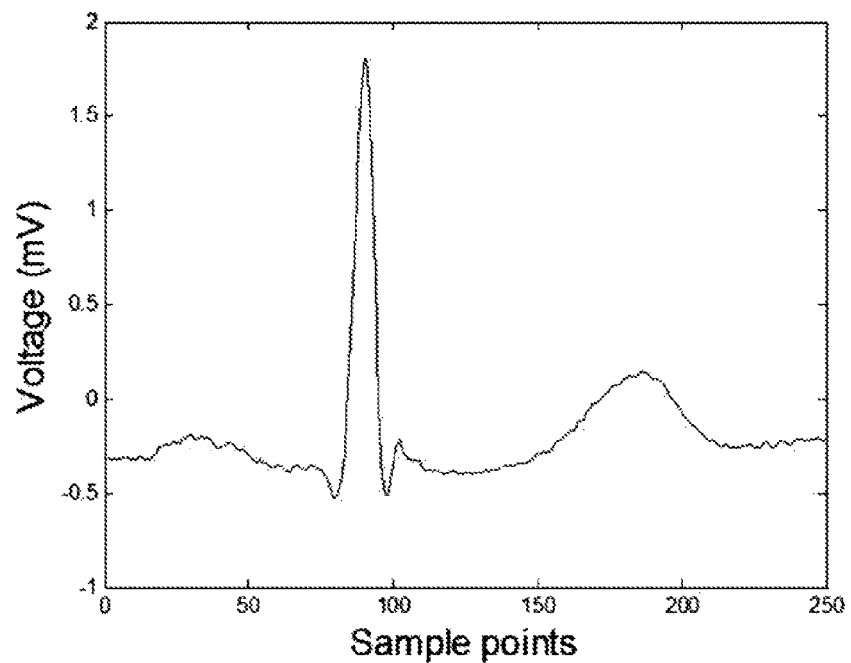
FIG. 11a and FIG. 11b show the comparison between a real ECG signal (FIG. 11a) and a synthesized ECG signal (FIG. 11b) using different Gaussian windows.
Figure 11B:
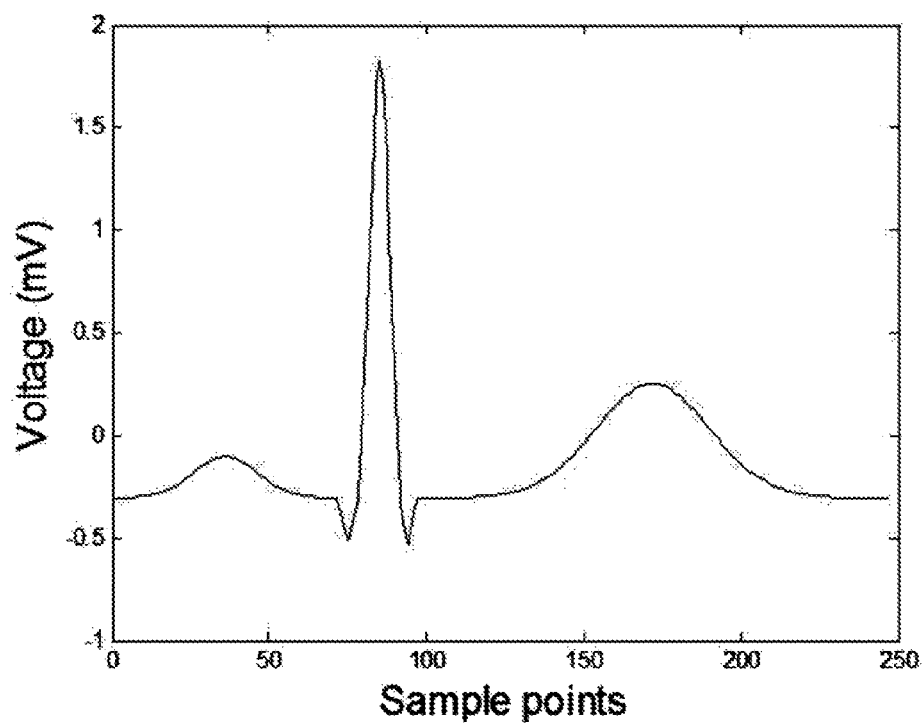

ECG signals can be regarded as Gaussian like waves. Specifically, ECG signals can be viewed as the combination of plural scales and the translations of Gaussian functions. FIG. 11a and FIG. 11b show the comparison between a real ECG signal (FIG. 11a) and a synthesized ECG signal (FIG. 11b) using different Gaussian windows. It may be proved that the two signals are very similar. In addition, the envelope of a Gabor filter may be also a Gaussian function. This is the reason why "Gabor" may be a better embodiment to be utilized in the method of present disclosure as described above.

Figure 12A:
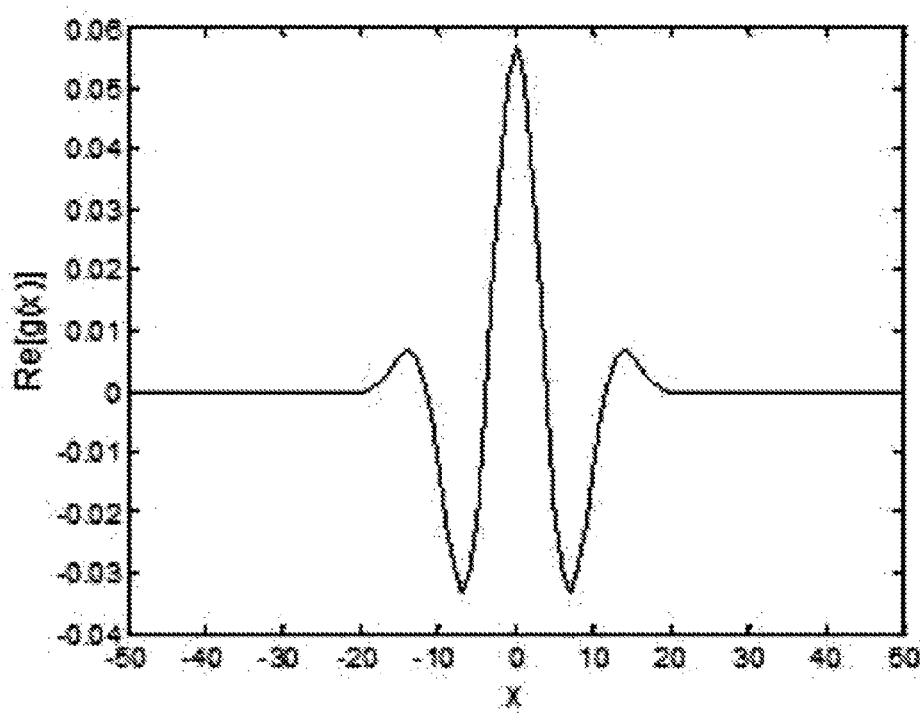
FIG. 12a, FIG. 12b and FIG. 12c show the selected waveforms of the Gabor filters.
Figure 12B:
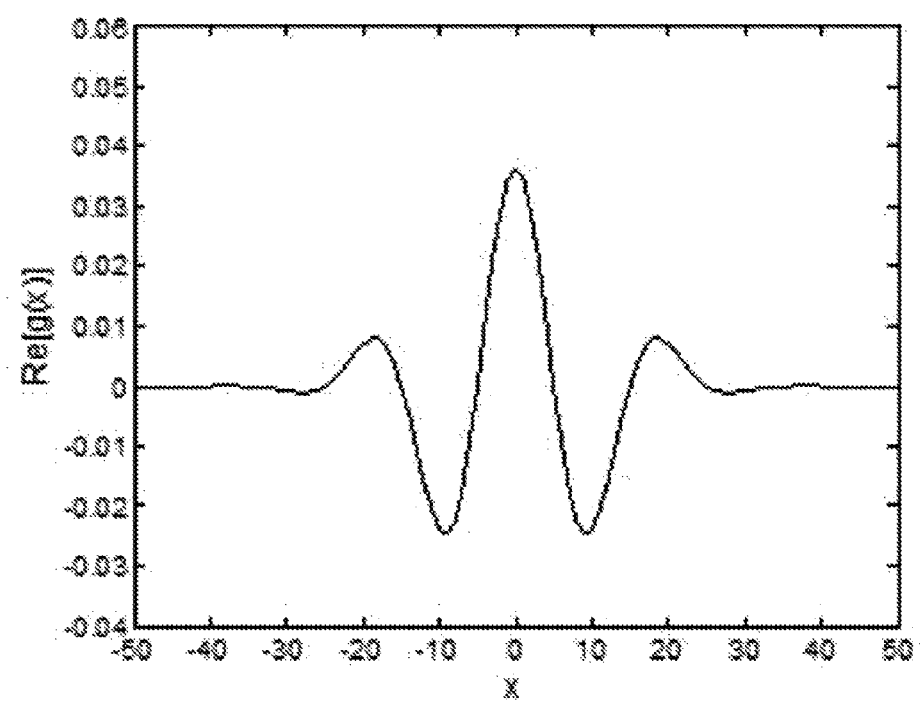
Figure 12C:
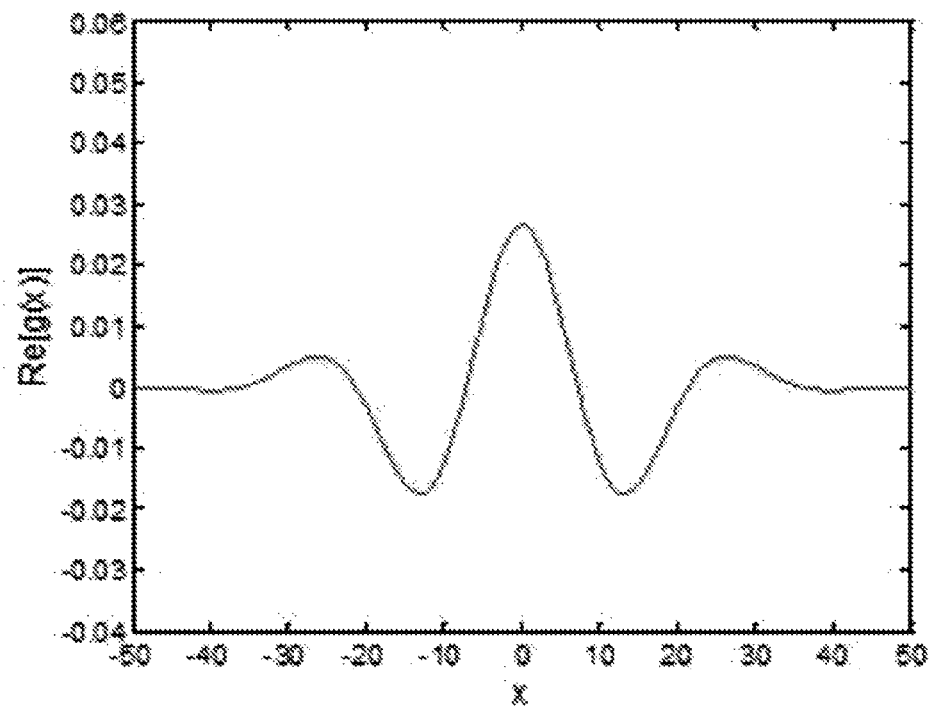
Figure 13A:
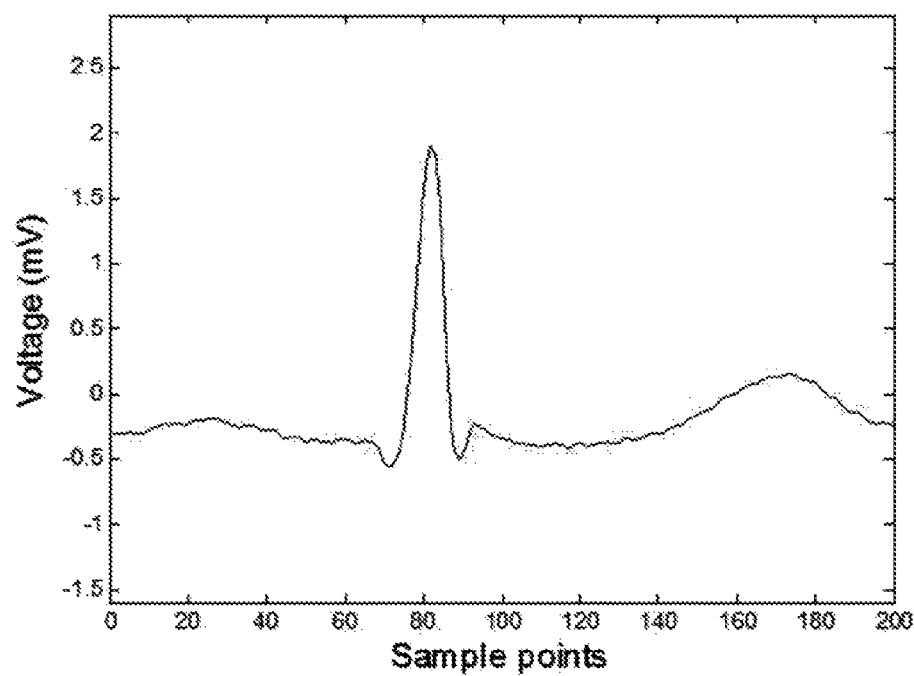
FIG. 13a, FIG. 13b and FIG. 13c show the Gabor filters may be chosen for different durations of the received QRS complex detection.
Figure 13B:
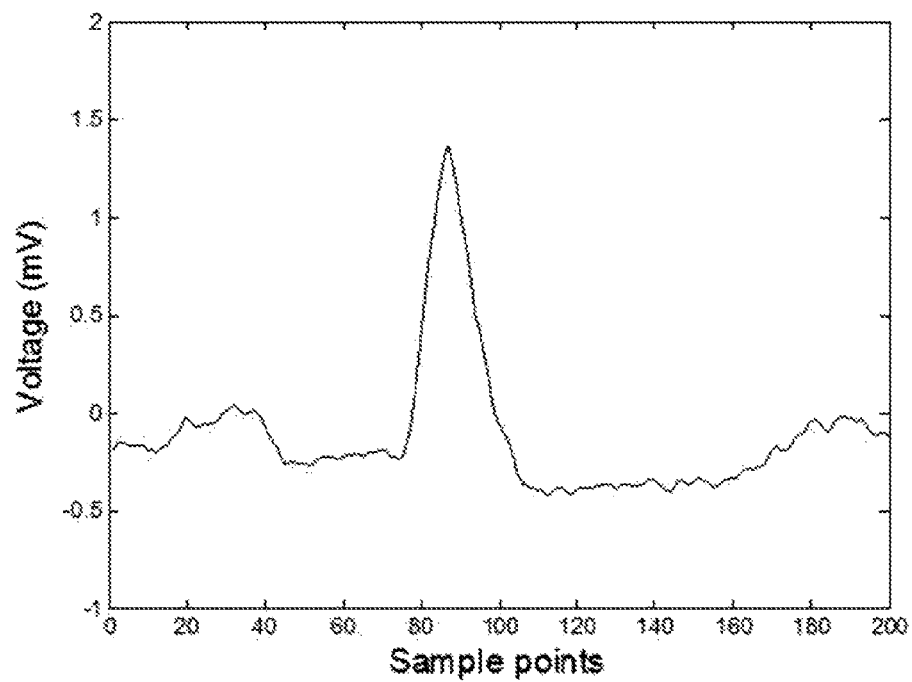
Figure 13C:
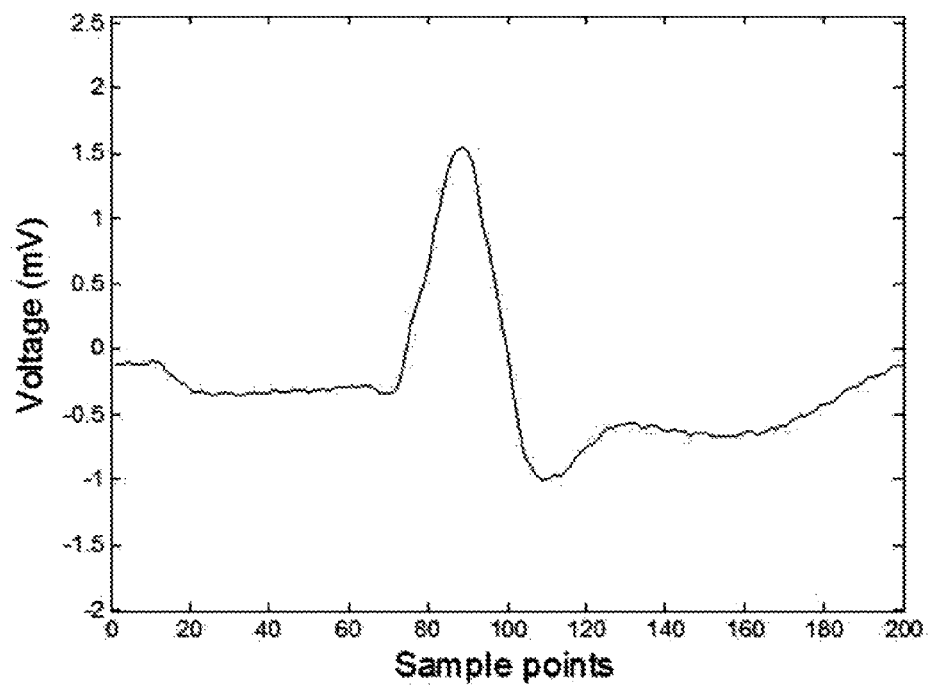
Figure 14A:
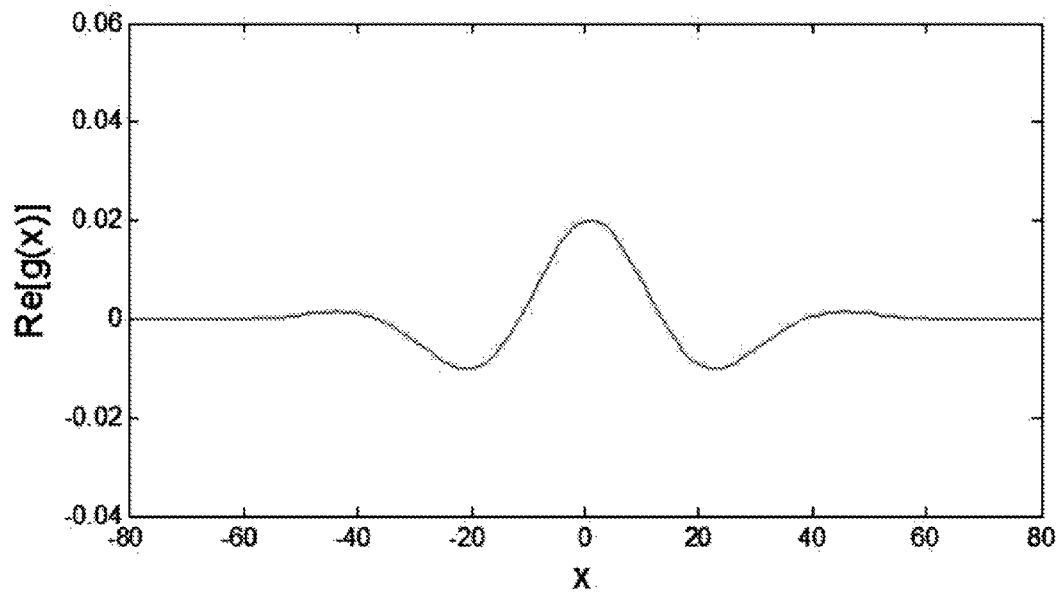
FIG. 14a shows the selected waveforms of the Gabor filters for P peak detection.
Figure 14B:
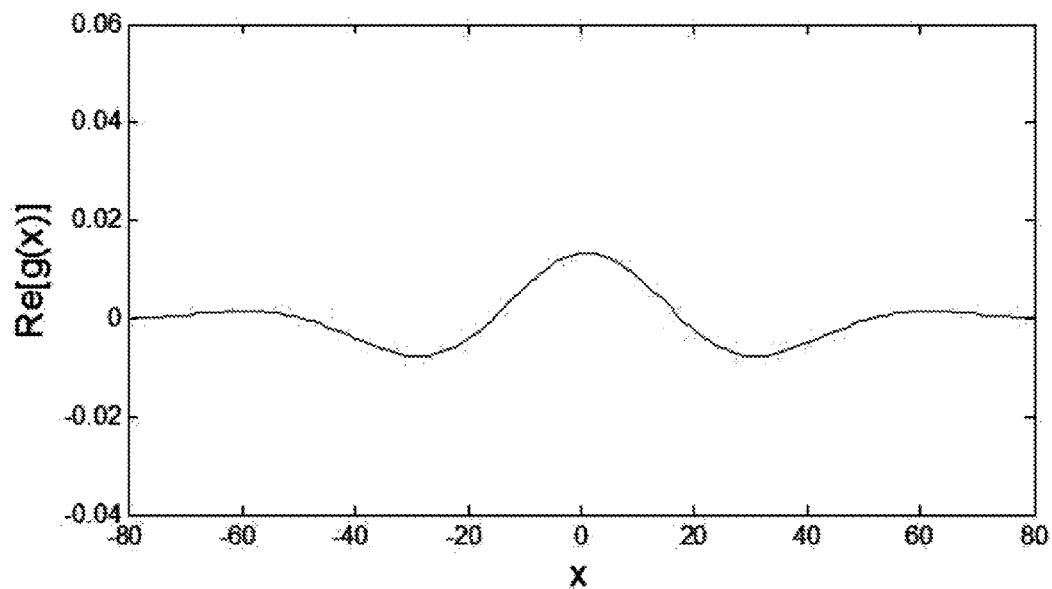
FIG. 14b shows the selected waveforms of the Gabor filters for T peak detection.
Figure 15A:
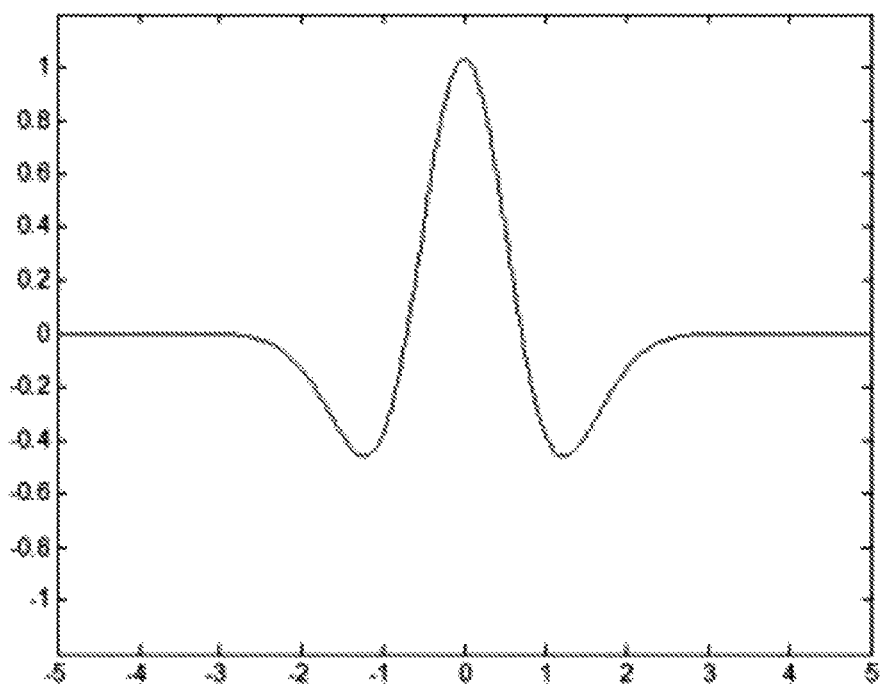
FIGS. 15a to 15d show various embodiments of Gabor mother wavelets by tuning different parameters in the Gabor function.
Figure 15B:
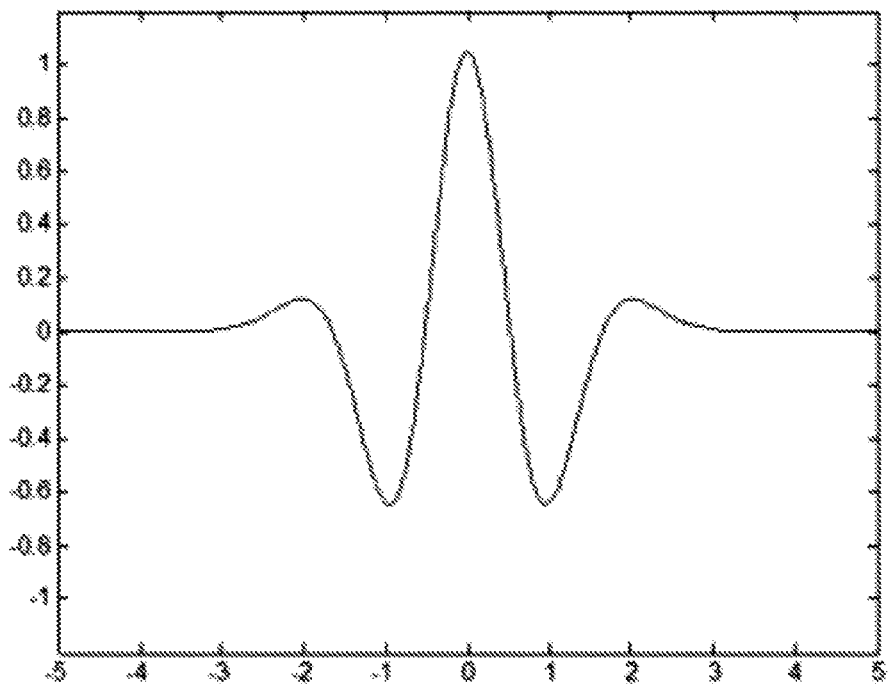
Figure 15C:
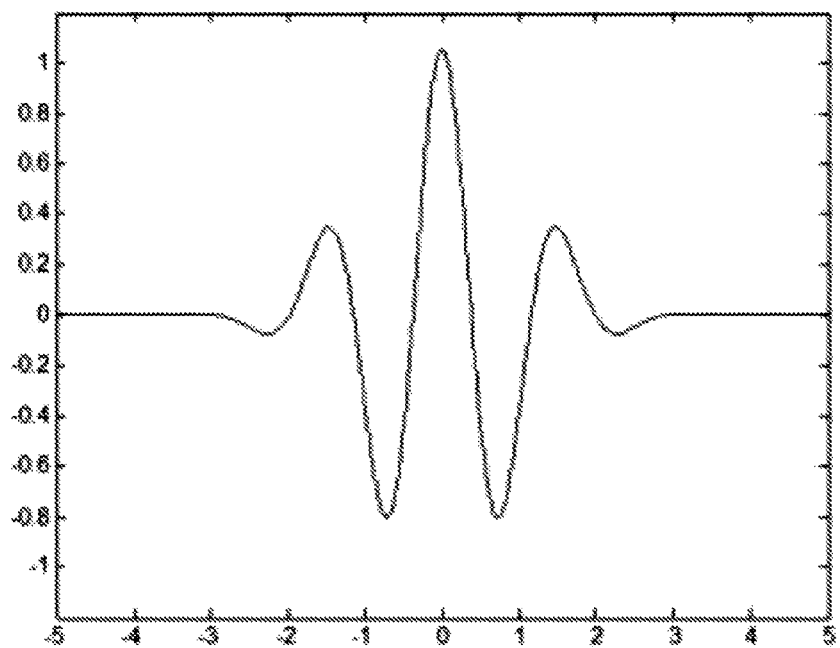
Figure 15D:
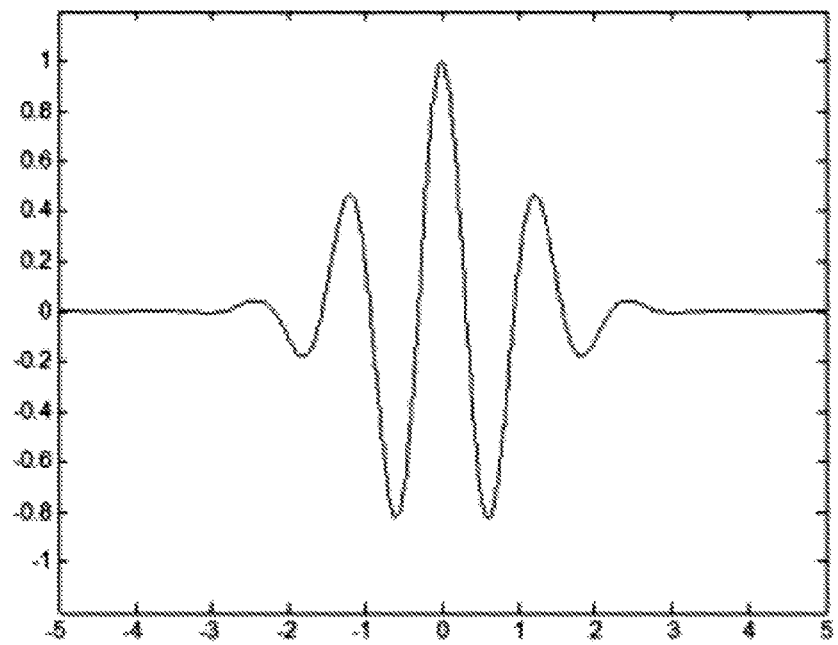

For the features within the QRS complex detection, the selected waveforms of the Gabor filters are shown in FIG. 12a, FIG. 12b and FIG. 12c. These Gabor filters may be chosen for different durations of the received QRS complex detection, as shown in FIG. 13a, FIG. 13b and FIG. 13c. In addition, for P peak detection, the selected waveforms of the Gabor filters are shown in FIG. 14a, and also, for T peak detection, the selected waveforms of the Gabor filters are shown in FIG. 14b.

It can be observed from these kinds of selected Gabor filters that the waveforms are very similar. The difference is the degree of dilation or erosion. There is a parameter 'a' that can be used to tune the scale of the corresponding mother wavelet. Hence, instead of using different parameters of Gabor filters to detect different features, WT with Gabor (Morlet) mother wavelet may be better since almost all features can be extracted by just one transformation. In other word, WT may be the merged results by different parameters of Gabor filters. Further, the "continuous" wavelet transform may be utilized, because the fine scale-tuning is needed.

In addition, further reason for the method of the present disclosure can omit the baseline drift removal is because the selected frequency band for feature detection will not overlap the affected frequency of the baseline drift (0 Hz~0.5 Hz). According to the property of WT, the frequency band of any scale of WT is a band pass filter. Therefore, for each feature extraction, the person in the art can use each appropriate band pass filter to prevent overlapping with the affected frequency of the baseline drift.

FIGS. 15a to 15d show various embodiments of Gabor mother wavelets by tuning different parameters in the Gabor function. In fact, there are a lot of types of Gabor mother wavelet. Thus, in order to choose an appropriate Gabor mother wavelet for the method, waveform and corresponding frequency band may be in the consideration. As described previously, the concept of the method of the present disclosure is to find the waveform similarity between each wave in ECG signals and the corresponding bases. Therefore, after observing the waveforms in FIGS. 12a, 12b, 12c, 14a and 14b for the features in different wave detections, FIG. 15b may be a better choice.

Figure 16:
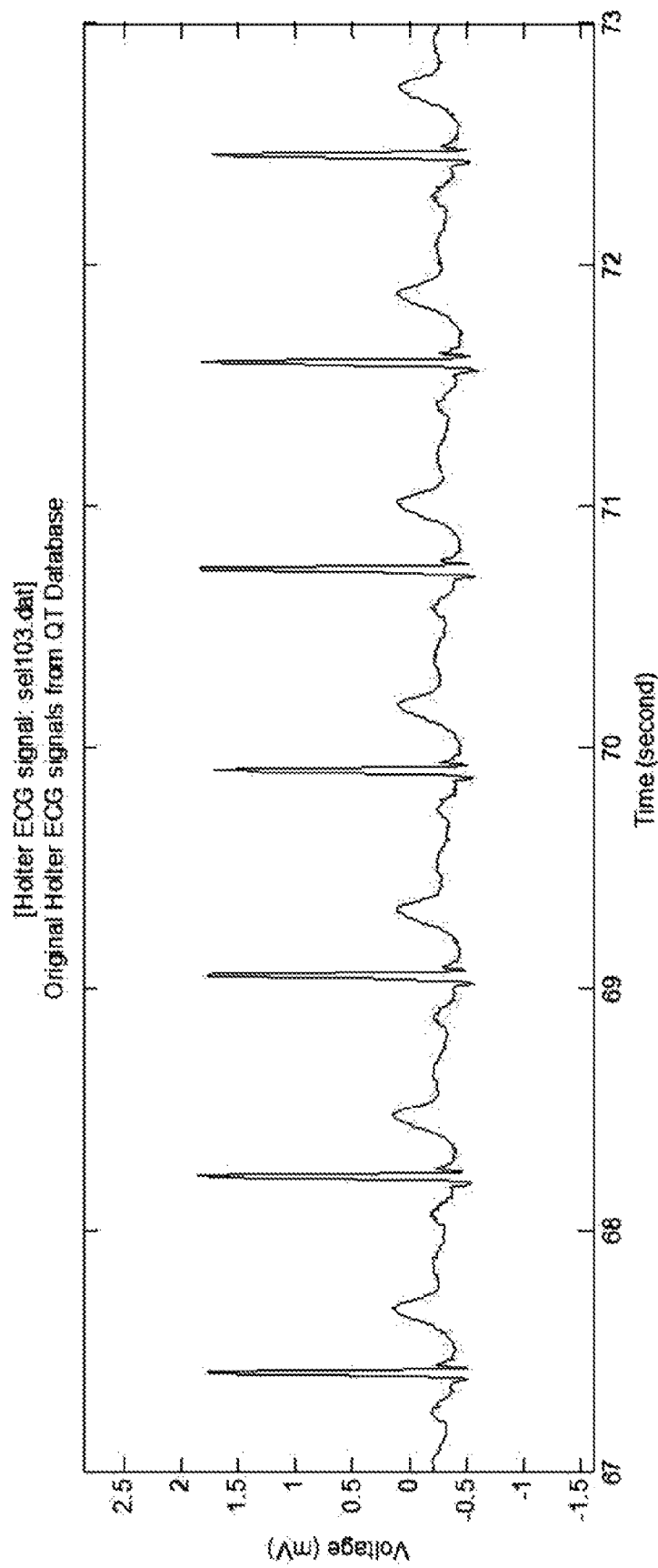
FIG. 16 shows the original signals.
Figure 17:
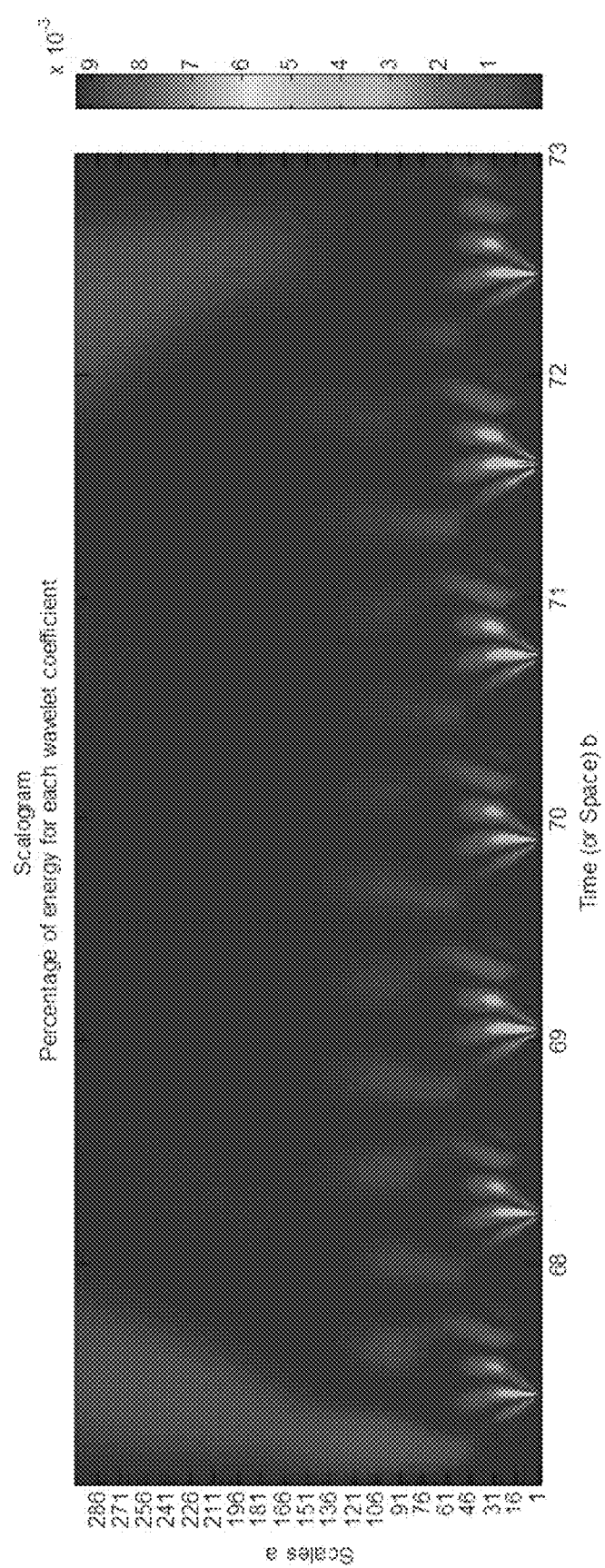
FIG. 17 shows the corresponding wavelet scalogram of CWT with the selected Gabor mother wavelet.

Finally, the embodiment of transferred result of CWT with the selected Gabor mother wavelet is presented. The original signals are shown in FIG. 16 (S0). The corresponding wavelet scalogram of CWT with the selected Gabor mother wavelet is shown in FIG. 17. The X-axis represents the parameter 'b' in WT or time index. The Y-axis represents the parameter 'a', wherein larger 'a' means smaller frequency. The responses are not equal with various scales (parameter 'a') at the same time.

Embodiment of ECG Signal Extraction for R Peak

Before detecting the R peak, it may be noted that the frequency of QRS complex is higher than other parts in the ECG signals. In the QRS complex, the highest voltage point is the position of the R peak. Summarizing the observations, the present disclosure of the extracting tactic of R peak is to distinguish the QRS complex and find the corresponding location concurrently and then to choose the position which contains the maximum voltage. Based on this tactic, time-frequency analysis may be utilized for the R peak detection.

Figure 18:
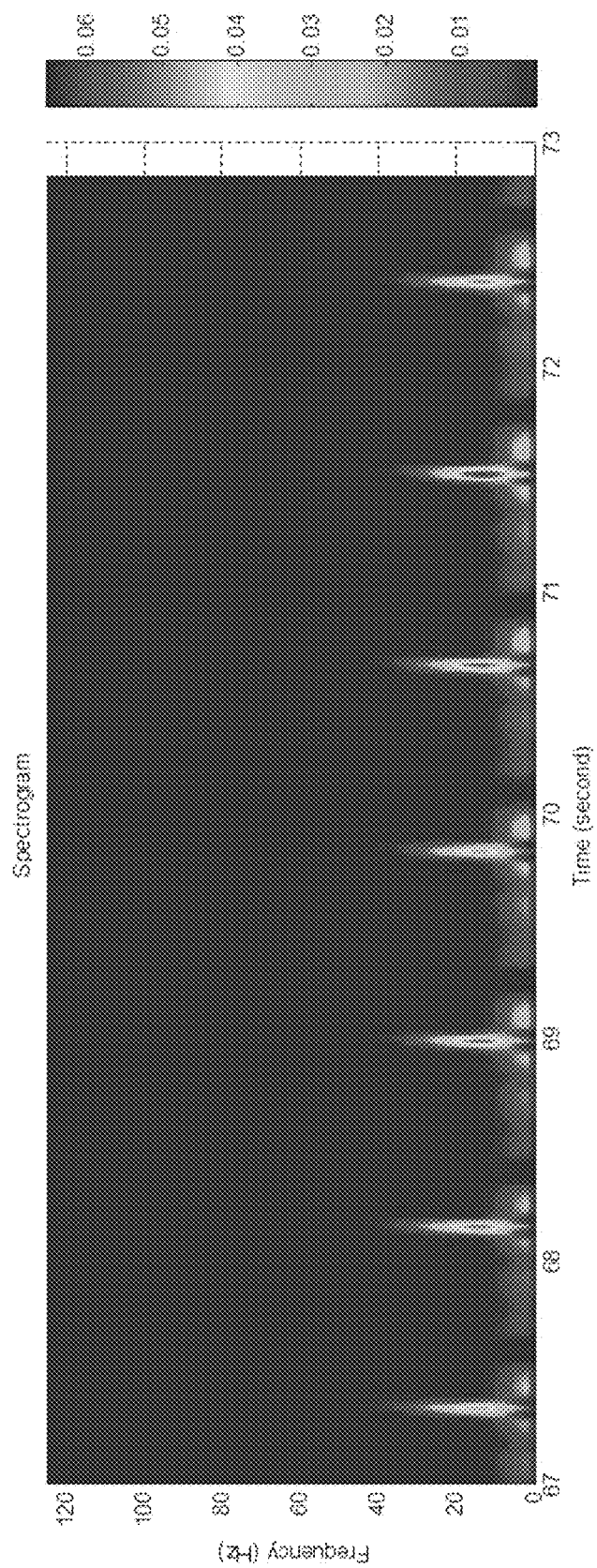
FIG. 18 shows the STFT transferred result.

In general, there are many time-frequency analysis methods. However, short-time Fourier transform (STFT) and wavelet transform (WT) may be two of the most popular methods. Referring back to FIG. 10, in the mid-phase development in the ECG signal extraction method of present embodiment, STFT may be utilized to detect the R peak. The attached transferred result is shown in FIG. 18, wherein the X-axis represents the time index and the Y-axis represents the frequency. What would be noticed is that the Y-axes in FIG. 17 (CWT) and FIG. 18 (STFT) represent different things. According to the transferred result of STFT, the response of the QRS complex part may be enhanced within 10 Hz to 25 Hz. Thus, the positions of QRS complex may also be extracted on the spectrogram concurrently.

The choice between CWT and STFT is discussed. First, STFT may be sufficient in characterizing the QRS complex and may be also easier to implement than WT, but STFT may be insufficient in detecting different widths of the QRS complex due to the "fixed scale" property in STFT. In contrast, CWT has multi-scale property to solve this problem. Hence, when lower complexity is requested STFT may be suggested, and when wider types of QRS complex are considered CWT may be suggested. For this tradeoff, CWT may be adapted since the "practicality" may be more important in the proposed ECG signal extraction method used in health care systems.

Figure 19A:
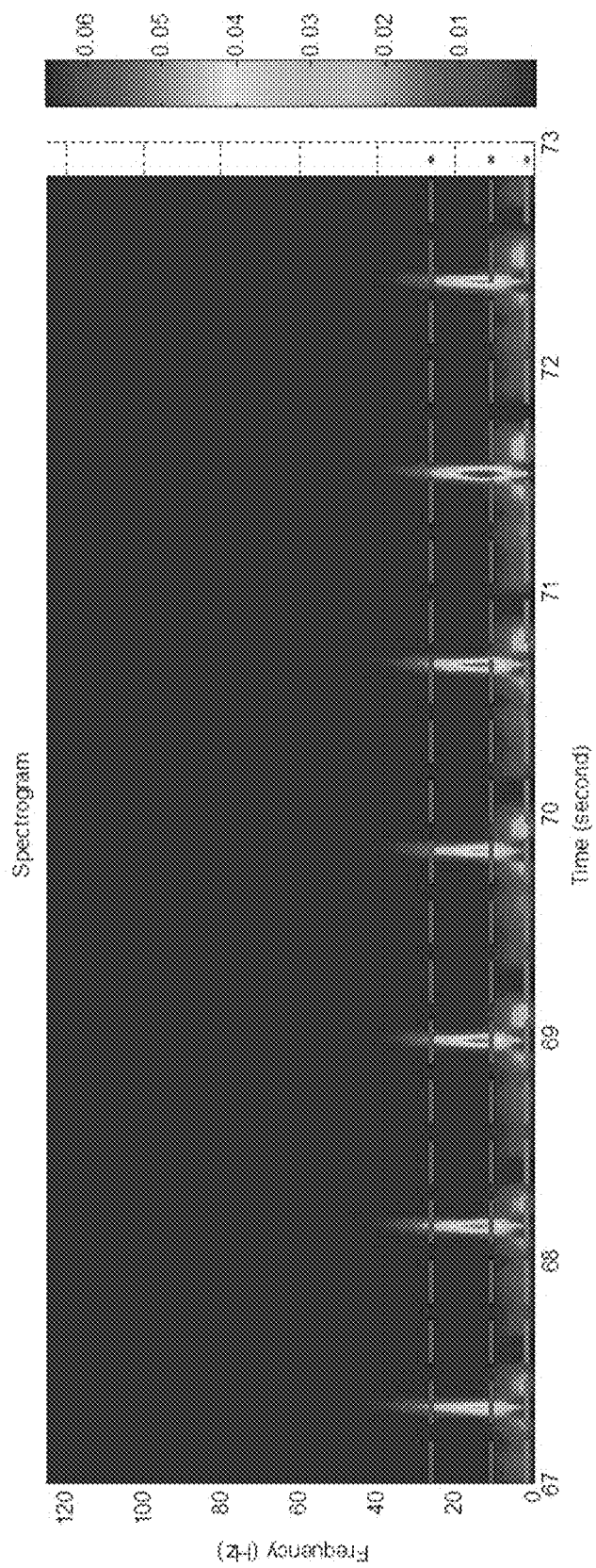
FIGS. 19a and 19b show the selected frequency bands of QRS complex with two red dotted lines (10 Hz to 25 Hz).
Figure 19B:
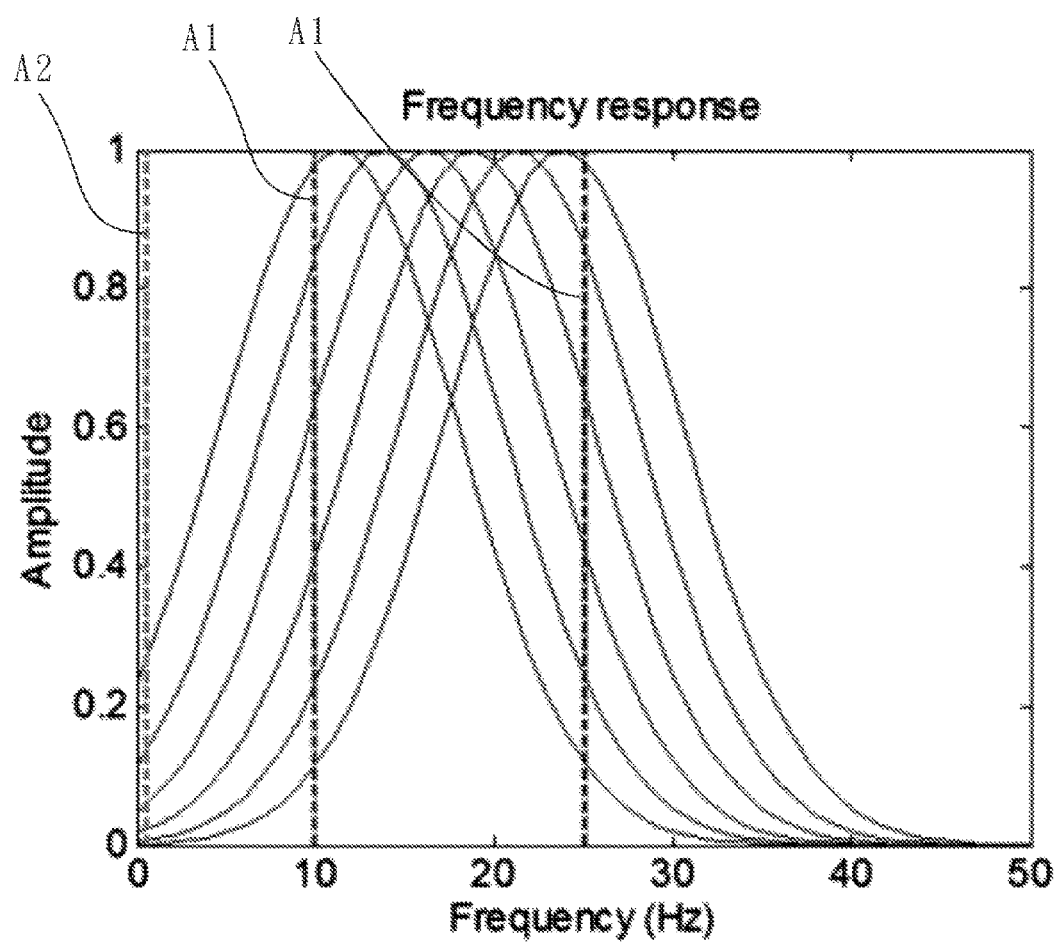
Figure 20A:
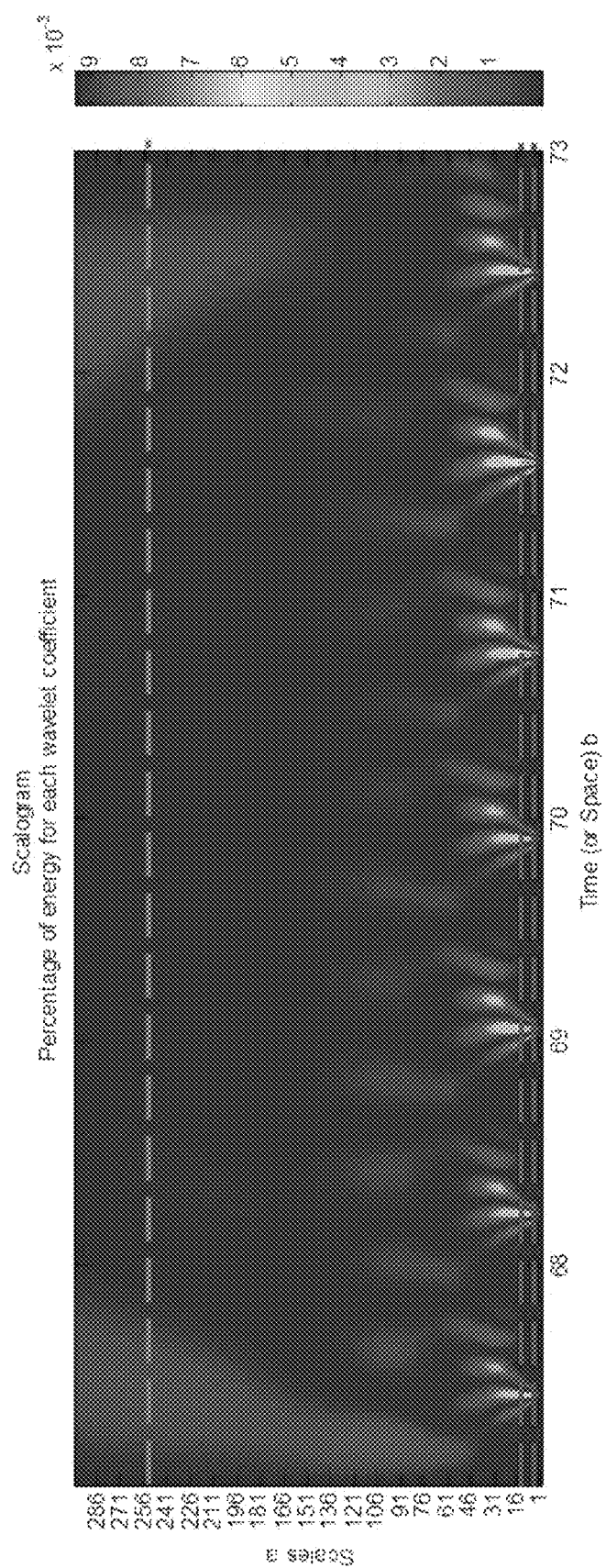
FIGS. 20a and 20b show the selected scales in CWT and its corresponding frequency response.
Figure 20B:
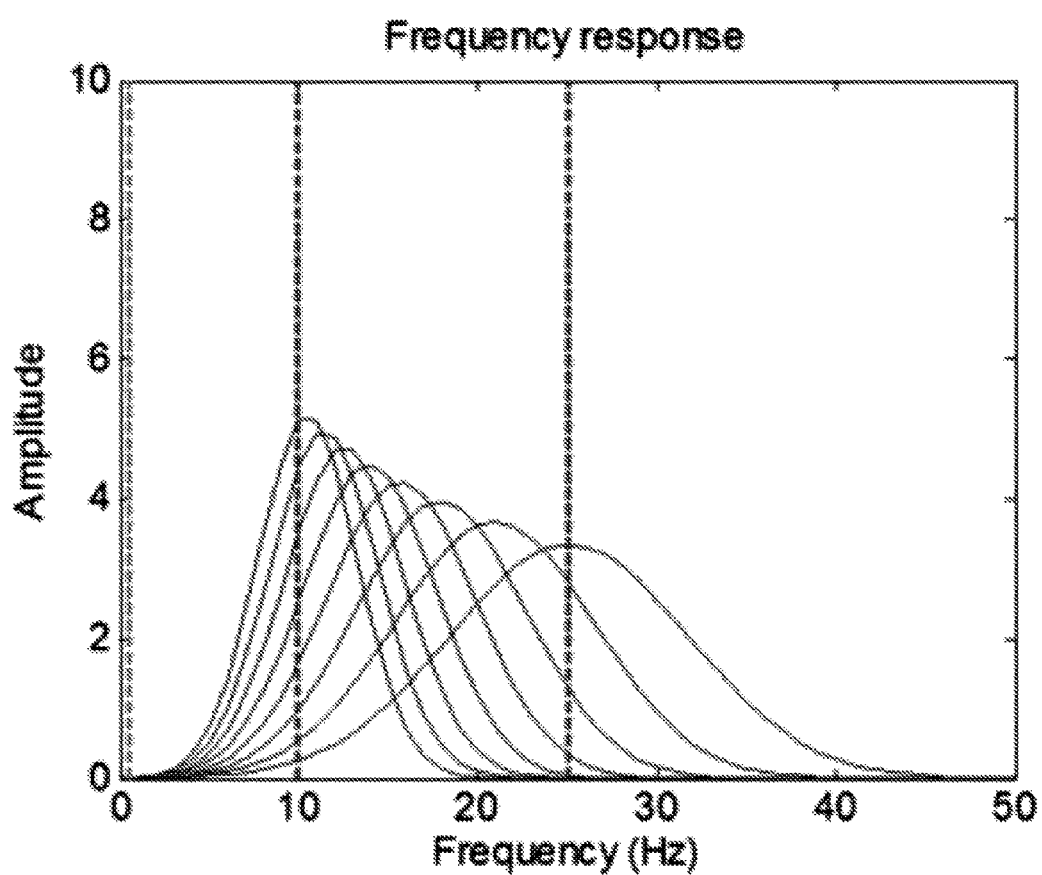

The consecutive sub-bands in STFT and CWT are compared. FIG. 19a shows the selected frequency bands in STFT and FIG. 19b shows the corresponding frequency response. The parts within two dotted lines A1 (10 Hz to 25 Hz) in both FIGS. 19a and 19b represent the selected frequency bands of QRS complex. The parts within 0 Hz to line A2 (0.5 Hz) in both FIGS. 19a and 19b represent general frequency bands of the baseline drift. FIG. 19a shows the transferred result of STFT with the selected response (the response within the two red dotted lines). FIG. 19b shows the sub-bands of the corresponding selected response in FIG. 19a. The selected scales in CWT are shown in FIG. 20a and the corresponding frequency response is shown in FIG. 20b. The different part is that the parts within line A2 (0.5 Hz) to infinite of 'a' (a theoretical value) in FIG. 20a represent general frequency bands of the baseline drift. It can be observed from FIGS. 19b and 20b that STFT mechanism may be affected more than CWT mechanism by the frequency band of the baseline drift. As mentioned above, other features within the QRS complex may be extracted by CWT with three different scales. If the R peak could not only be extracted by CWT but also be with the same three of different scales, the complexity of all ECG feature extraction systems could be lower. Namely, if the R peak can be extracted using CWT with also three different scales, the complexity of all ECG feature extraction systems could be lower. Hence, after summarizing these reasons, it may be motivated to adopt CWT mechanism in the ECG signal extraction method of present embodiment.

Figure 21A:
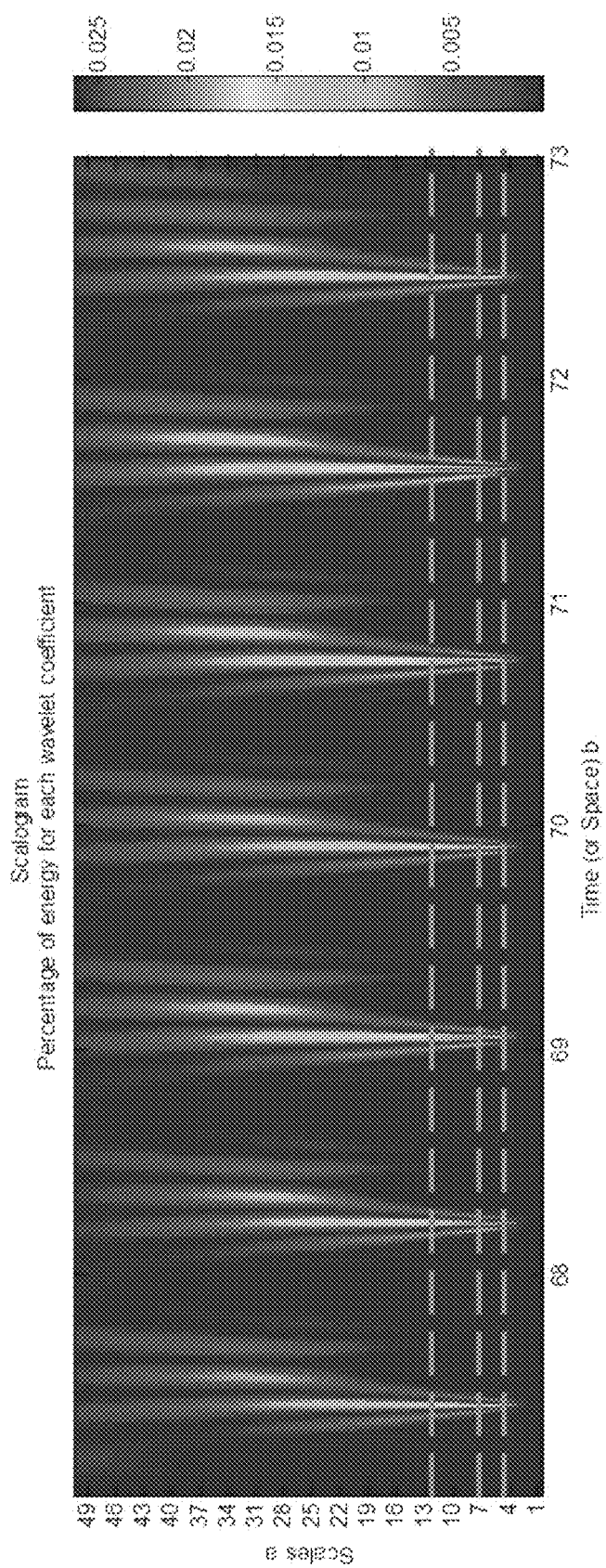
FIG. 21a shows the responses of three different scales of CWT with Gabor mother wavelet, utilizing for the R peak detection, and the summarized result is shown in FIG. 21b.
Figure 21B:
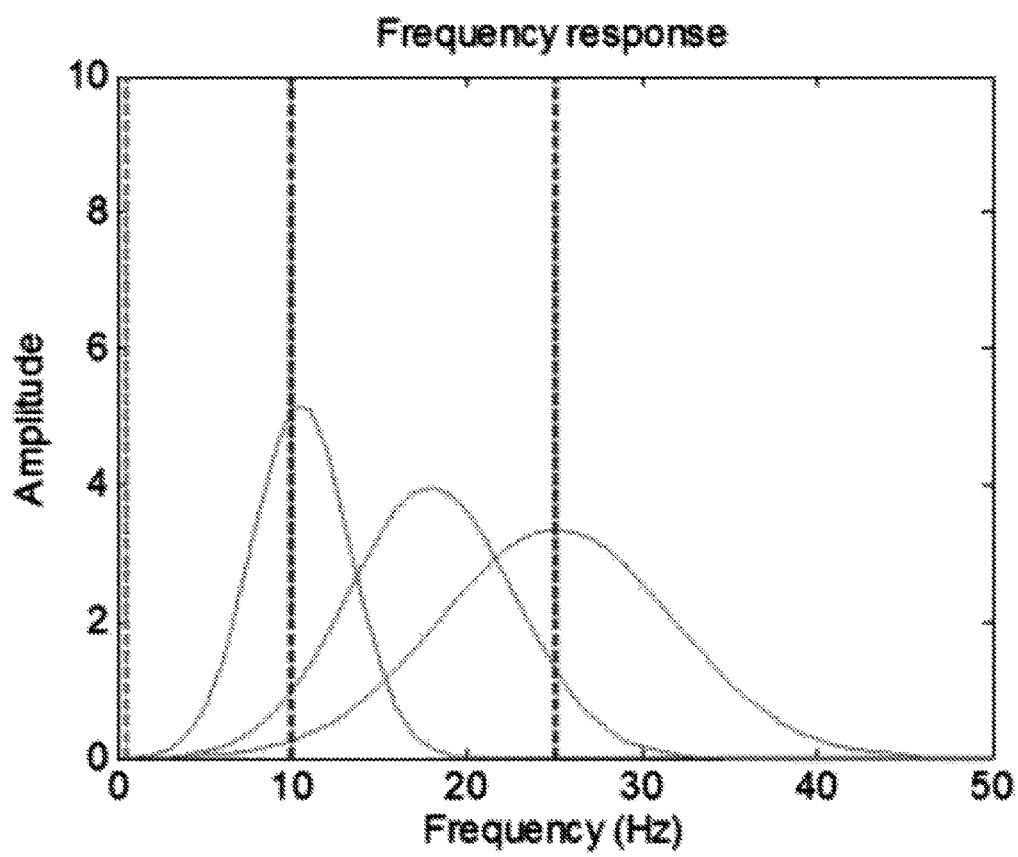
Figure 22A:
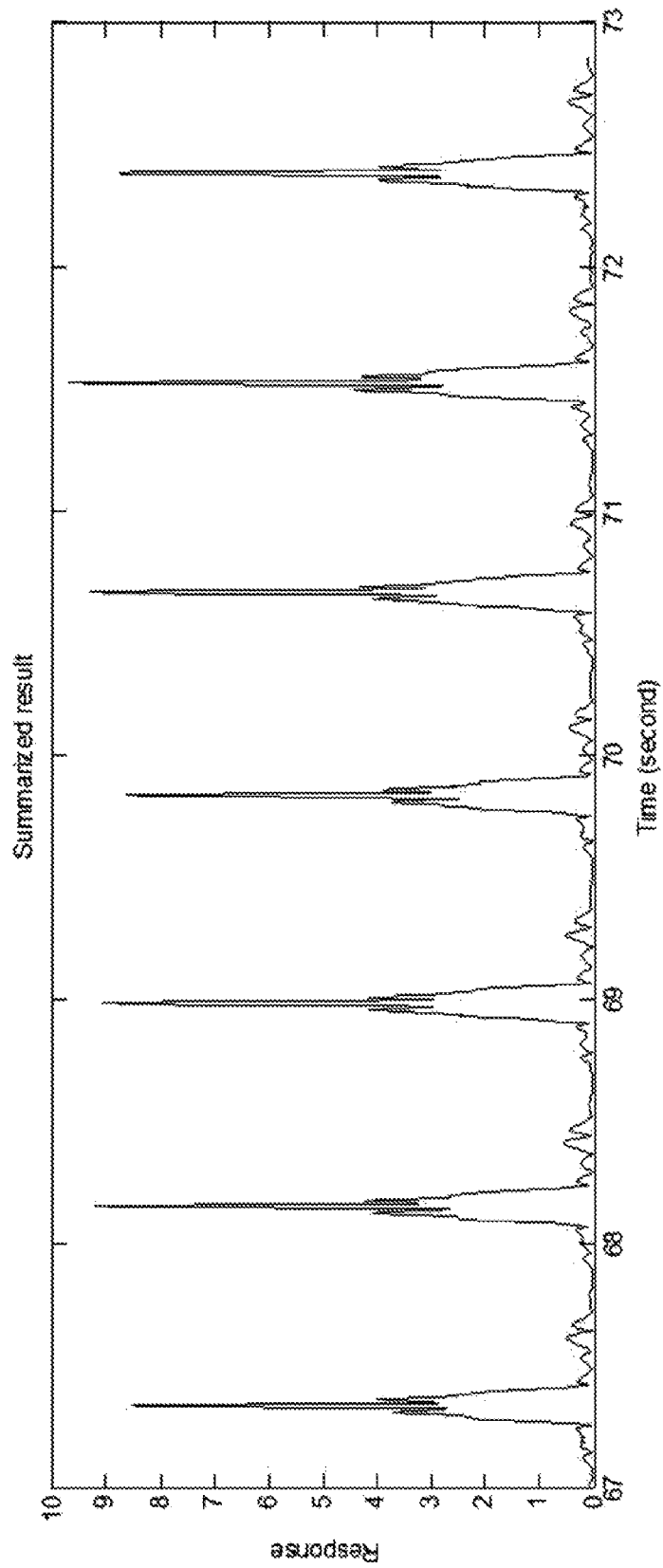
FIGS. 22a and 22b shows adaptive thresholding proposed for finding the R peak candidates.
Figure 22B:
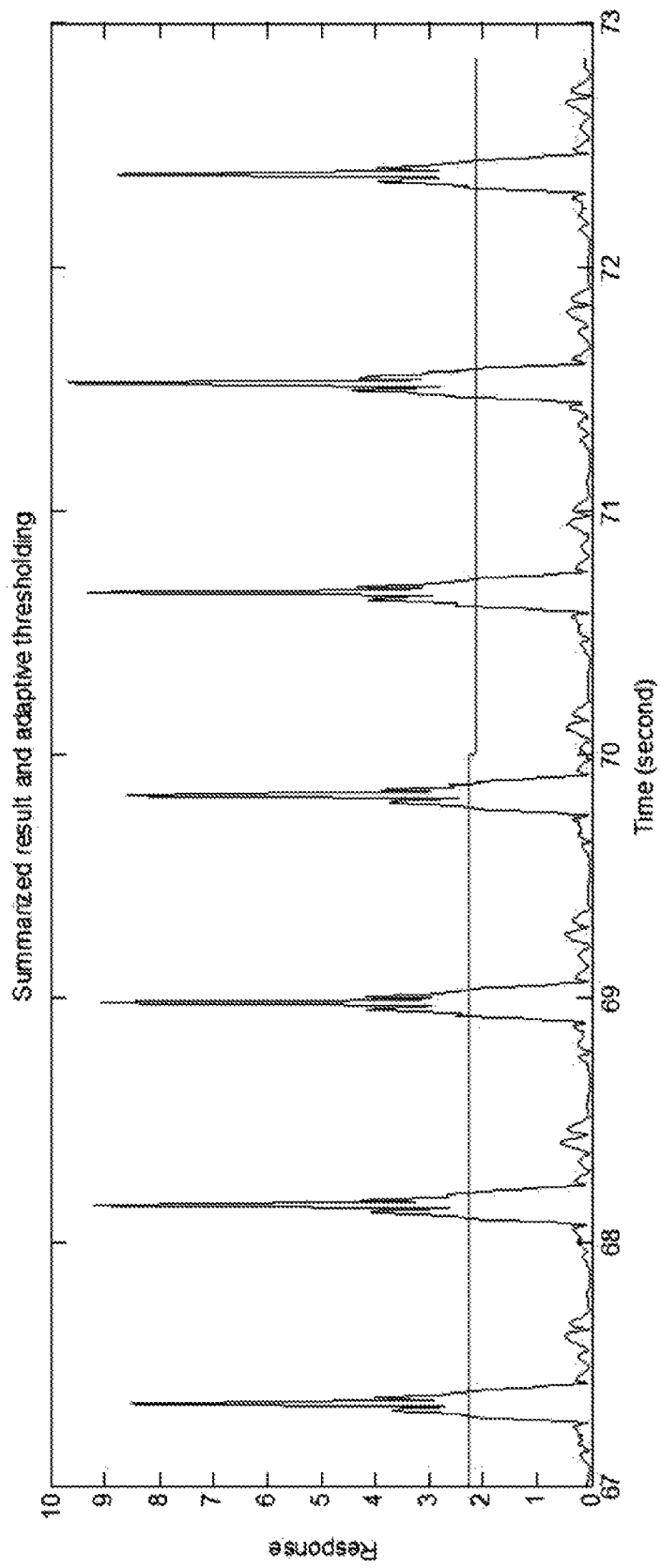
Figure 23:
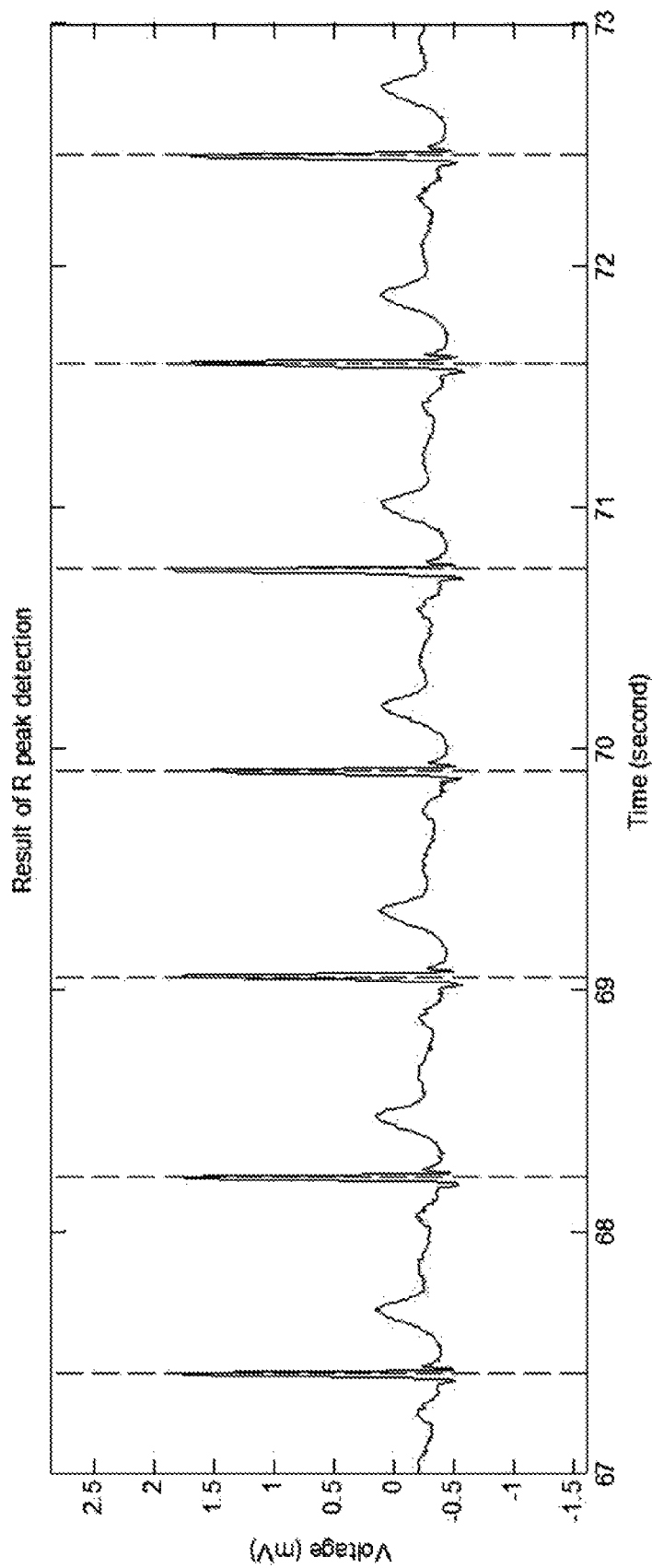
FIG. 23 shows the detected positions corresponding R peak, with red dotted lines are the positions of the R peak.

Then, the R peak detection is discussed. According to the analysis above, the responses of three different scales of CWT with Gabor mother wavelet shown in FIG. 21a may be utilized for the R peak detection (FIG. 21a is the corresponding scalogram generated by performing a time-frequency transformation on the ECG signal received in the step S0). The three dotted lines A3 in FIG. 21a which show the response of the corresponding scales in CWT may be summarized, and the summarized result is shown in FIG. 21b. Note the step S2 is adapted to select a predefined R-pertinent scale from FIG. 21a, and the step S3 is adapted to generate a R-pertinent summarized response (one of the waveforms in FIG. 21b) by performing the time-frequency transformation on the scalogram. However, three predetermined R-pertinent scales can be selected. In the embodiment, adaptive thresholding is proposed for finding the R peak candidates, as shown in FIGS. 22a and 22b. The term "adaptive" may contain two parts. One part is that the value for thresholding may be determined based on the information of the summarized result. Another part of "adaptive" is that the first part may be re-calculated every particular period of time. As an example, the period of time may be set as 3 seconds in the present embodiment. After the adaptive thresholding, every R peak candidate can be found. Finally, the positions with the maximum voltage may be found from the original ECG signals within every R peak candidate. Hence, the positions are the corresponding R peak. The result of the R peak detection is shown in FIG. 23. The dotted lines are the positions of the R peak. From FIG. 23, R peak positions of the ECG signal can be obtained as being located at relative maximum responses on the R-pertinent summarized response.

Embodiment of ECG Signal Extraction for Q, S Peak and QRSon, QRSoff

In the following sections, Q, S Peak and QRSon, QRSoff detections are discussed. As described previously, the waveforms depicted in FIGS. 12a, 12b and 12c may be utilized for the Q, S peak and QRSon, QRSoff detections. Here, three of these Gabor filters may be merged into CWT. The reason to select the waveform in FIG. 15b as the proposed Gabor mother wavelet is because the waveform is most similar to the selected Gabor filters in FIGS. 12a, 12b, 12c, 14a and 14b. In addition, the reason why the three filters in FIGS. 12a, 12b and 12c may be chosen as features within the QRS complex detection is because the waveforms between QRS complex and the proposed selected Gabor filters are similar. The observed result can be obtained by comparing the waveform similarity between FIGS. 12a, 12b and 12c and FIGS. 13a, 13b and 13c. This is one of the reasons why the waveform in FIG. 15b may be selected as the Gabor mother wavelet in the present embodiment.

Figure 24A:
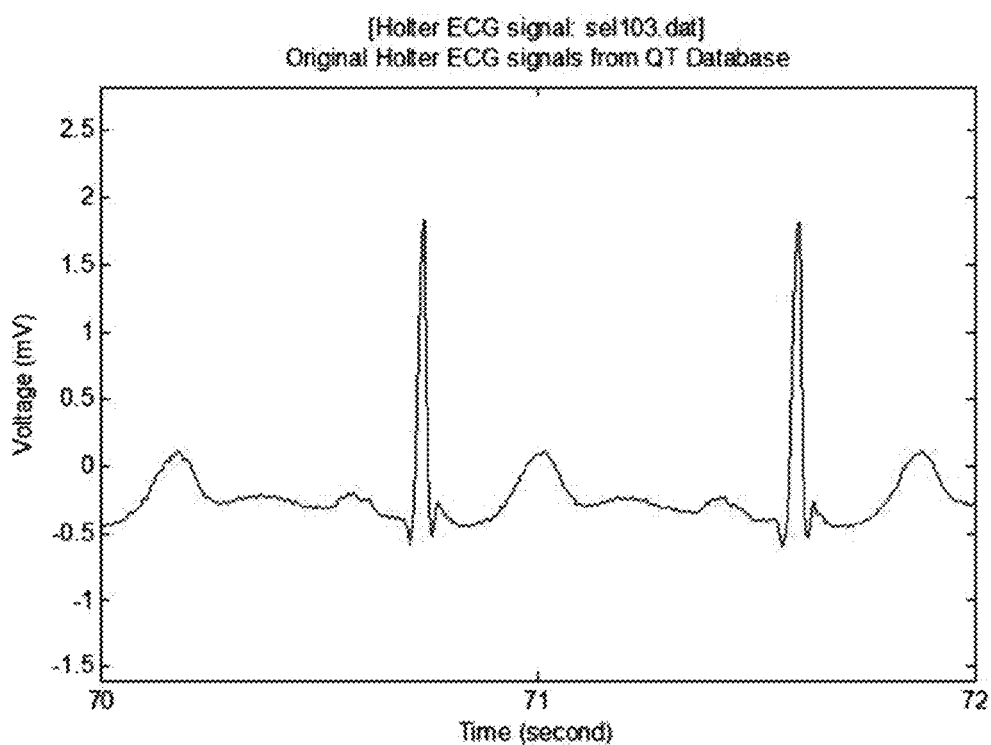
FIG. 24a-24h show the steps and experimental results of the Q, S peak, QRSon and QRSoff detections.
Figure 24B:
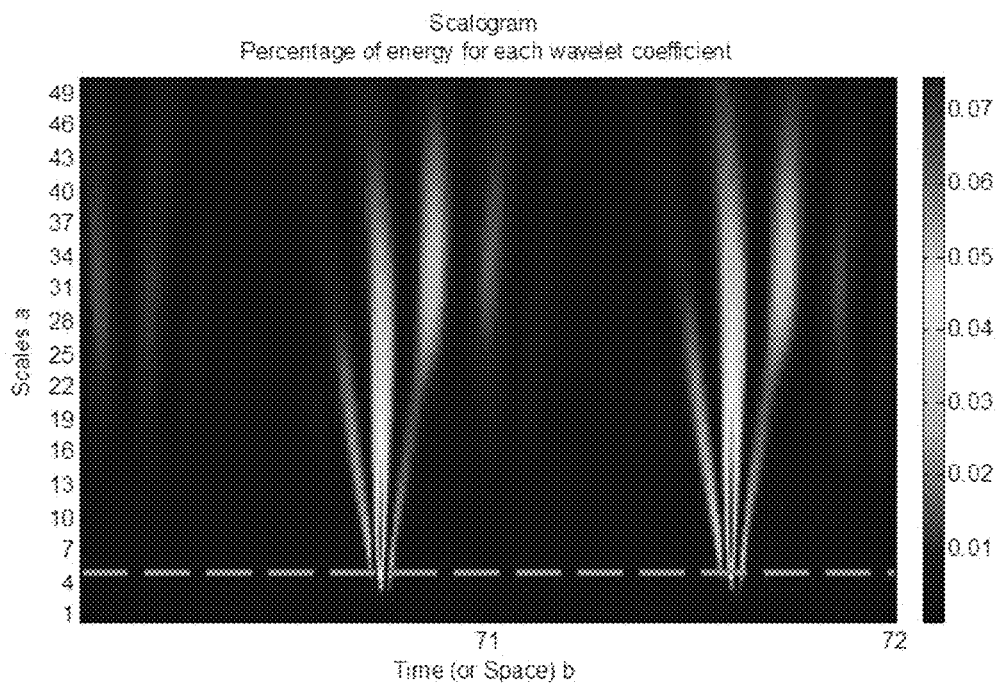
Figure 24C:
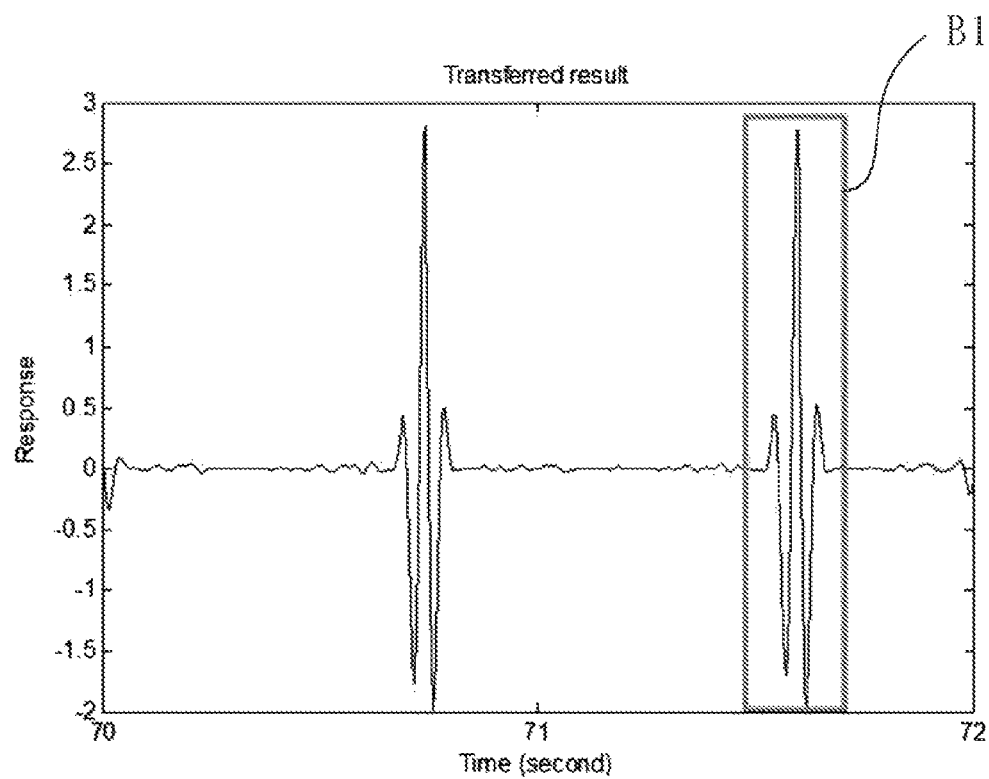
Figure 24D:
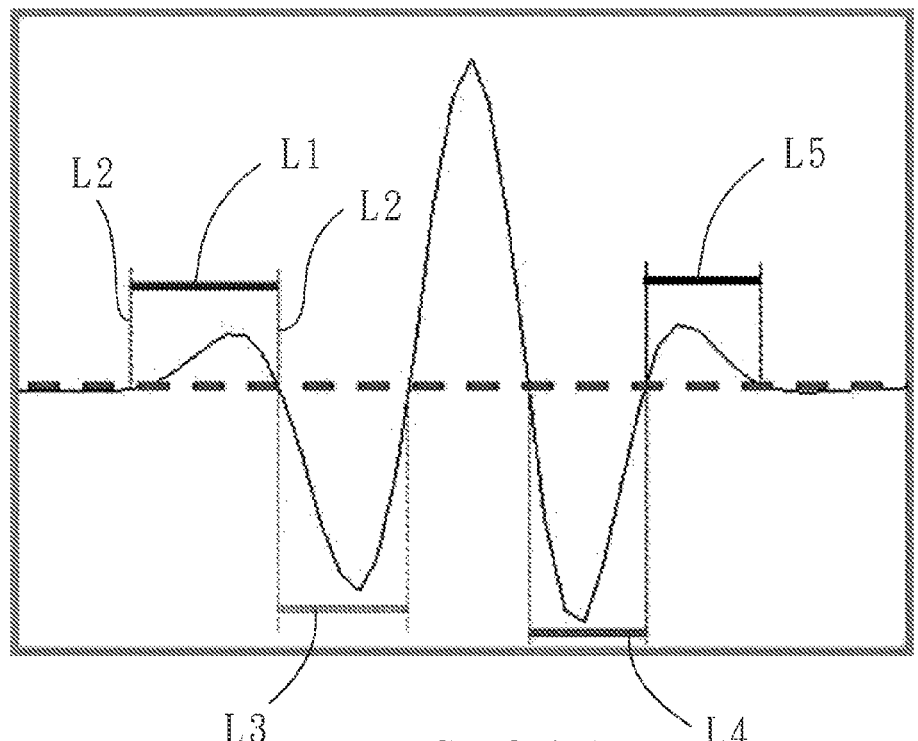
Figure 24E:
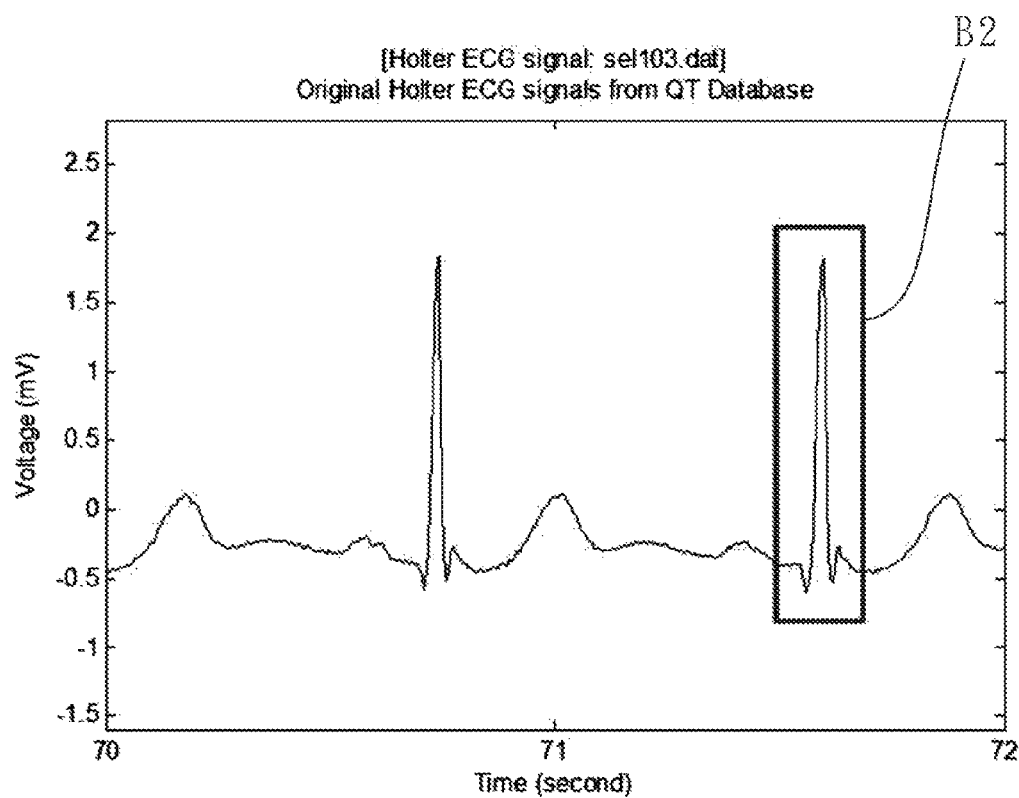
Figure 24F:
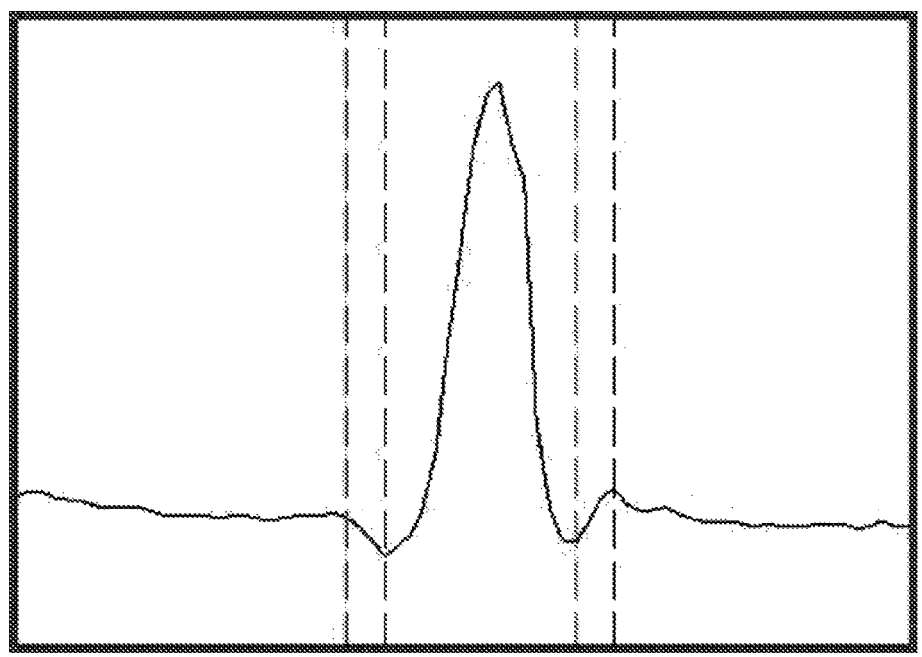

Since Q, S peaks and QRSon, QRSoff in QRS complex are surrounded by R peak, the positions of these features may also be detected after the R peak is found. FIGS. 24a-24h show the steps and experimental results of the Q, S peak, QRSon and QRSoff detections. FIG. 24a shows original ECG signals. The corresponding scalogram of CWT is shown in FIG. 24b. From FIG. 24b, a predefined QRS-pertinent can be selected. The responses within the parts of QRS complex in the ECG signals are enhanced, and the other parts almost disappeared. FIG. 24c depicts the selected response followed by the dotted line in FIG. 24b. In FIG. 24c, a QRS-pertinent transferred response is generated by performing the time-frequency transformation on the selected predefined QRS-pertinent scale. FIG. 24d is the part of response within block B1 in FIG. 24c. After observing the response in FIG. 24d, it can be found that three parts of the responses are positive, and two parts of the responses are negative. The three parts of positive responses from left to right are possible QRSon, R peak, and QRSoff, respectively. The two parts of negative responses from left to right are possible Q peak and S peak, respectively. The part of horizontal line L1 which is the intervals of two vertical lines L2 in FIG. 24d indicates the candidates for QRSon. Similarly, horizontal lines L3, L4 and L5 indicate the candidates for Q peak, S peak, and QRSoff, respectively. After finding the candidates of these features, the corresponding positions may be extracted from the original ECG signals. Q peak and S peak may be found within the boundaries of the corresponding candidates which contain the minimum voltage in the original signals. Subsequently, QRSon and QRSoff may be found within the boundaries of the corresponding candidates which contain the minimum response of second derivative of the original signals. In FIG. 24d, QRSon and QRSoff positions may be determined as being located at relative minimum second derivatives of the response before and behind the R peak position, respectively. The reason why the minimum value of second derivative may be utilized is because the locations of QRSon and QRSoff are on the greatest changed slope and the trend of the slope changes from large to small. FIG. 24f is the part of the original signals within block B2 in FIG. 24e wherein vertical lines L1, L3, L4 and L5 indicate the positions of QRSon, Q peak, S peak, and QRSoff, respectively. Specifically, the Q peak position of the ECG signal may be determined as being located at the relative maximum negative response before the R peak position. In addition, the S peak position of the ECG signal may be determined as being located at the relative maximum negative response behind the R peak position.

Figure 24G:
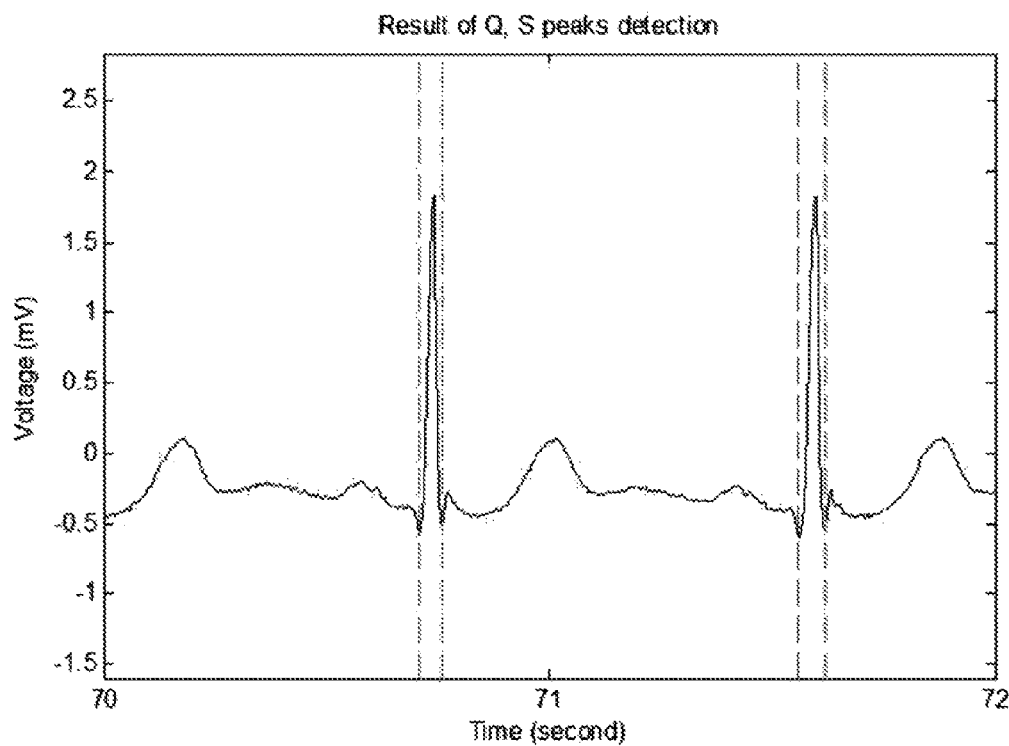
Figure 24H:
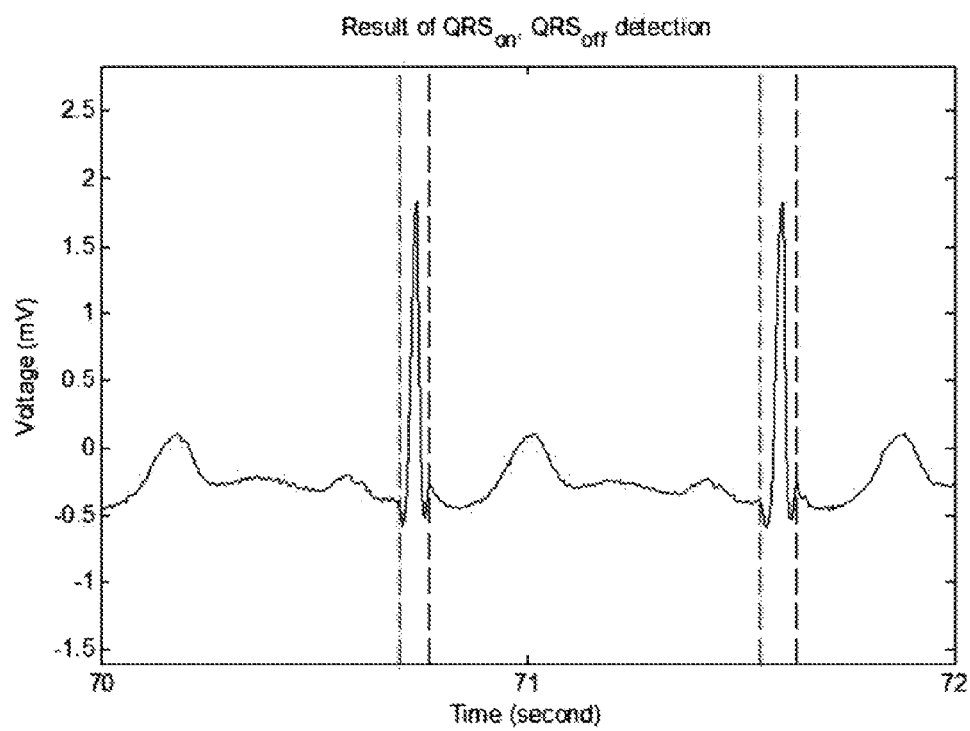

Finally, FIGS. 24g and 24h show the experimental results of the Q, S peak detections as well as the QRSon, QRSoff detections, respectively.

According to the above description, three Gabor filters in FIGS. 12a, 12b and 12c may be used to detect different durations of the QRS complex (FIGS. 13a, 13b and 13c). After the mechanism by Gabor filters is merged in CWT with Gabor mother wavelet, three responses from three scales may be utilized for various durations of the QRS complex detection. The selected scales are the same as three scales used in the R peak detection since the purpose of both R peak detection and Q, S peak, QRSon, QRSoff detections is to enhance the part of the QRS complex.

Figure 25A:
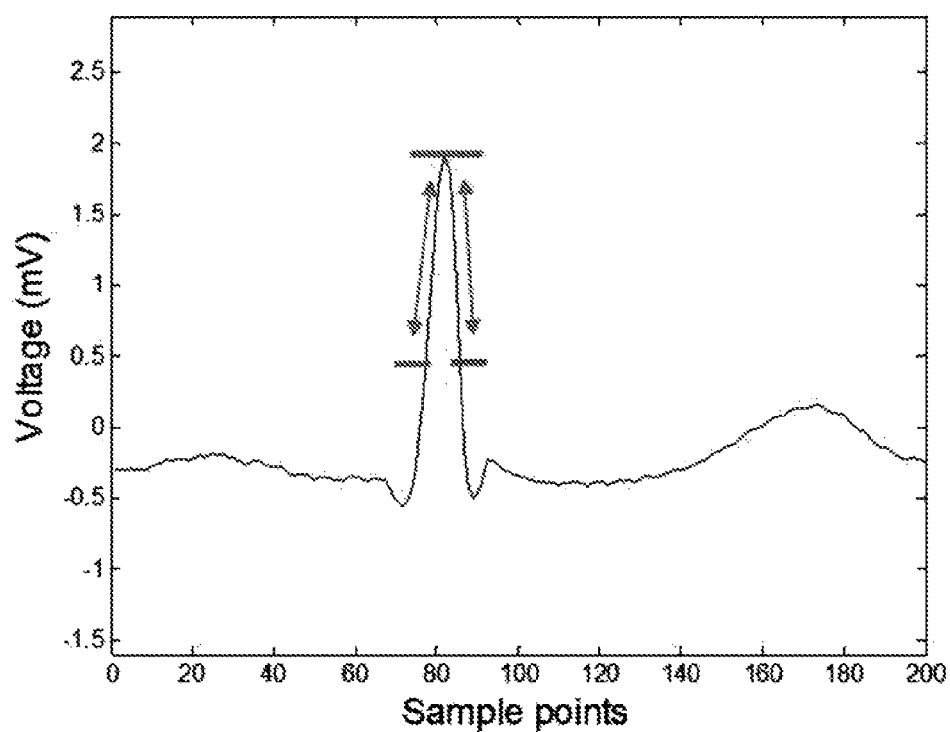
FIGS. 25a, 25b and 25c show the slopes of QR and RS in different durations of QRS complex.
Figure 25B:
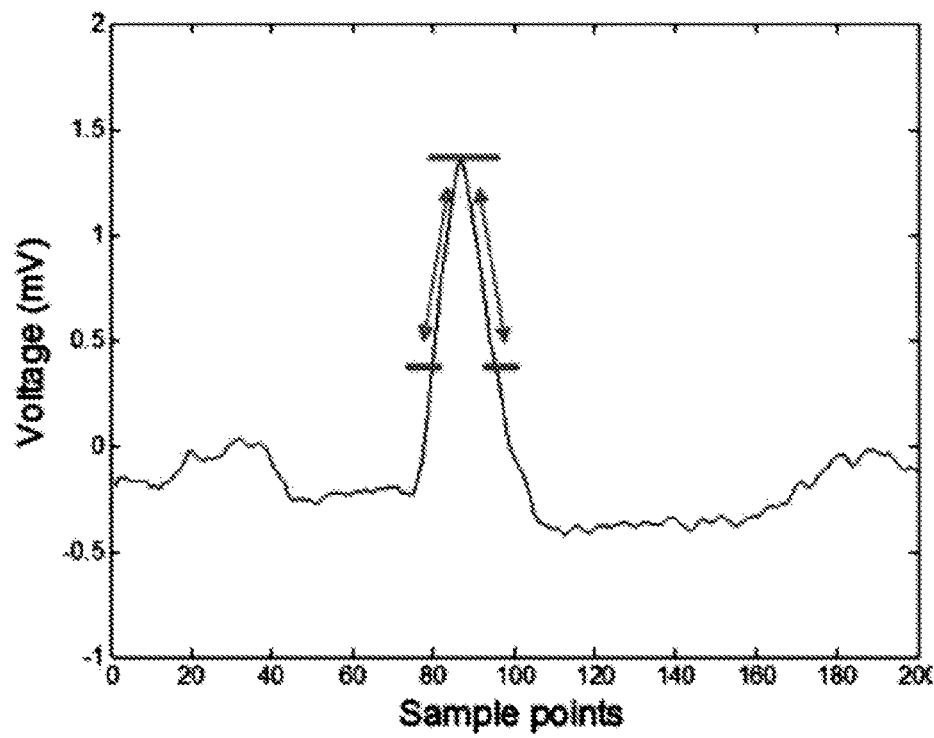
Figure 25C:
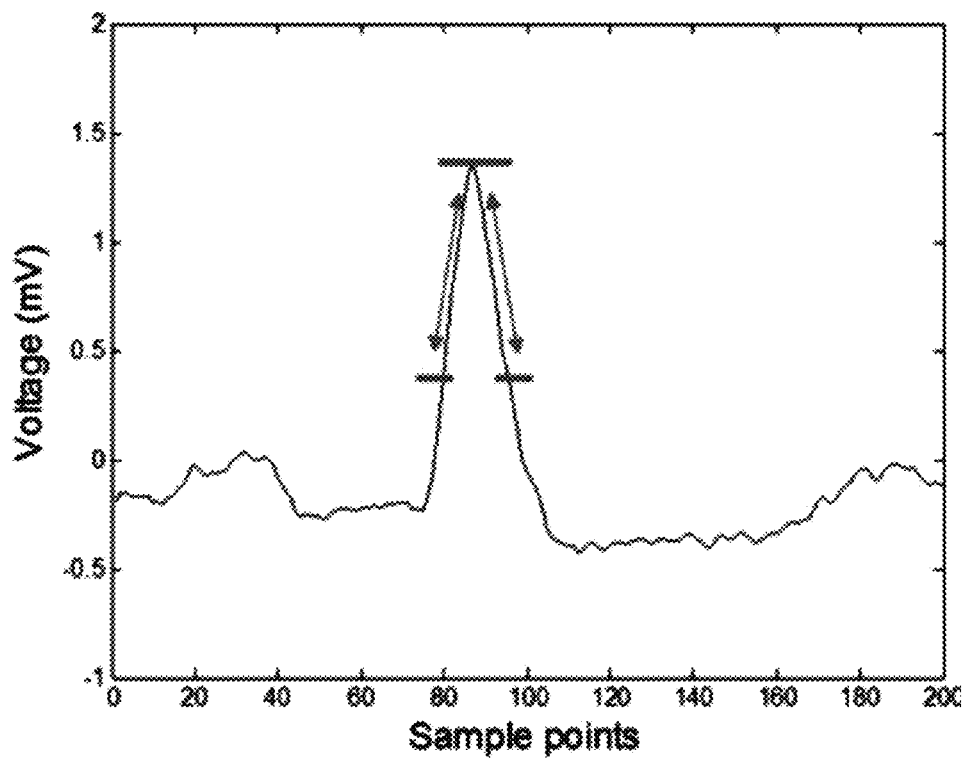
Figure 25D:
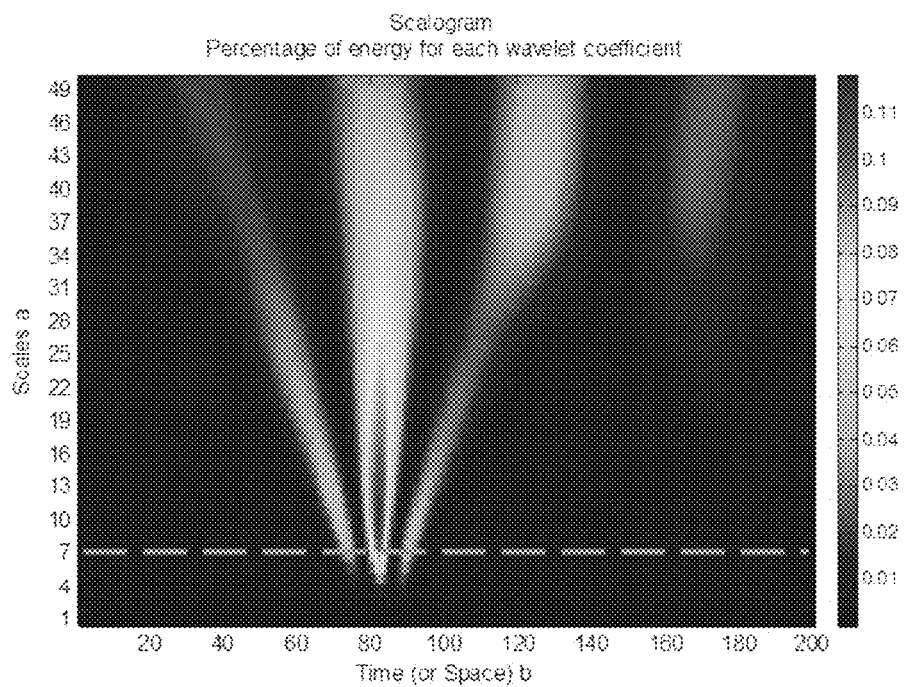
FIGS. 25d, 25e and 25f show the results of the scalogram on FIGS. 25a, 25b and 25c.
Figure 25E:
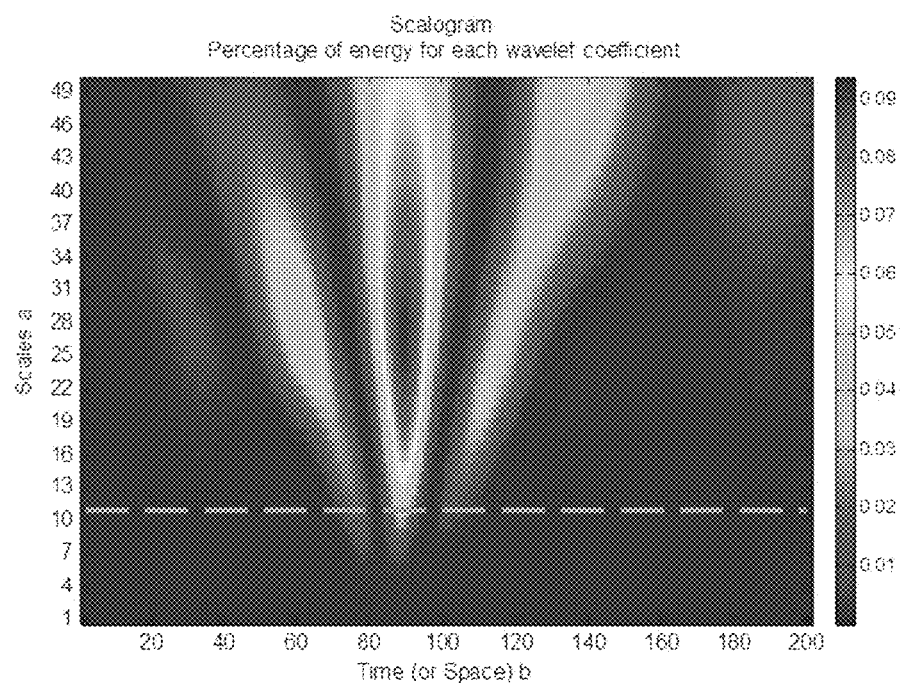
Figure 25F:
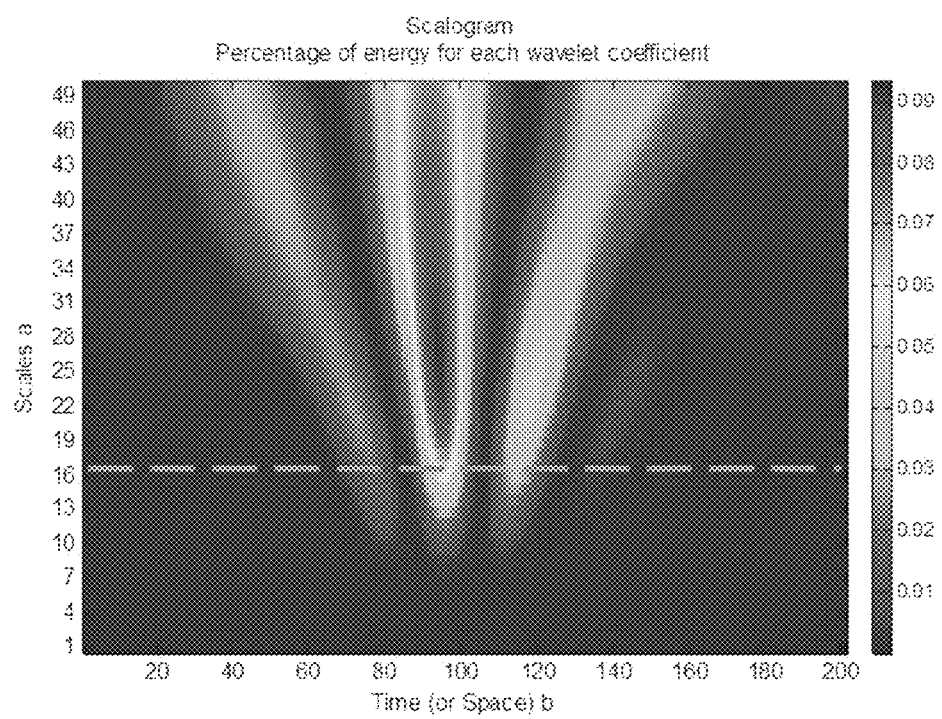
Figure 25G:
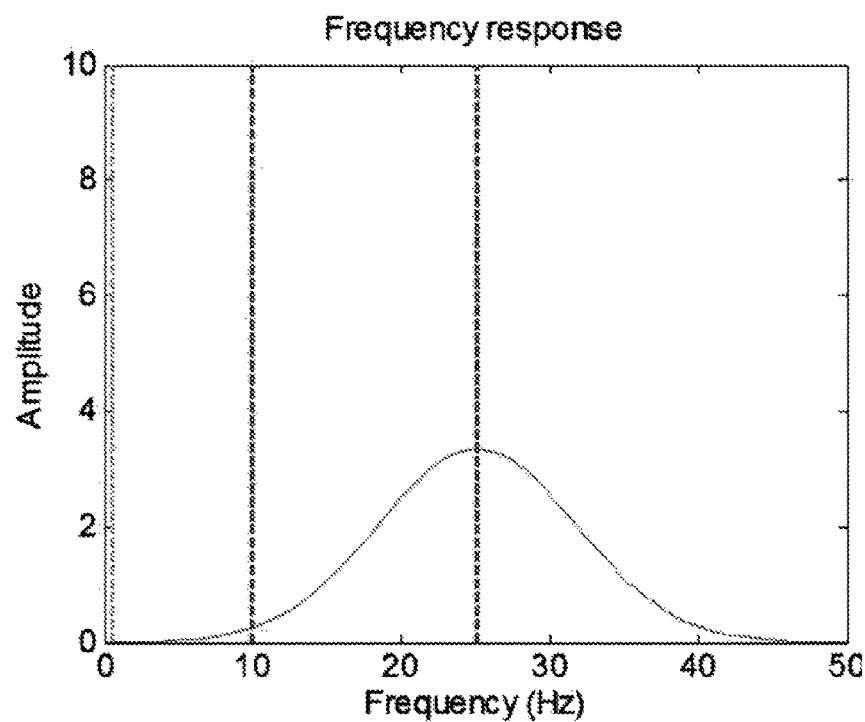
FIGS. 25g, 25h and 25i show the corresponding bandwidths shown in the light blue horizontal dotted line in FIGS. 25d, 25e and 25f, and FIGS. 25j, 25k and 25l show the corresponding experimental results.
Figure 25H:
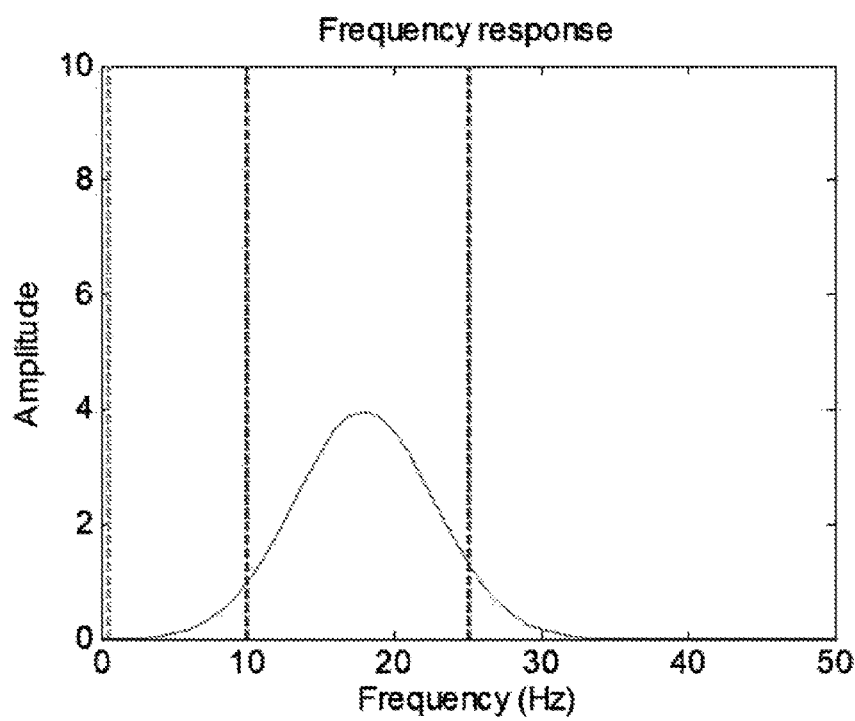
Figure 25I:
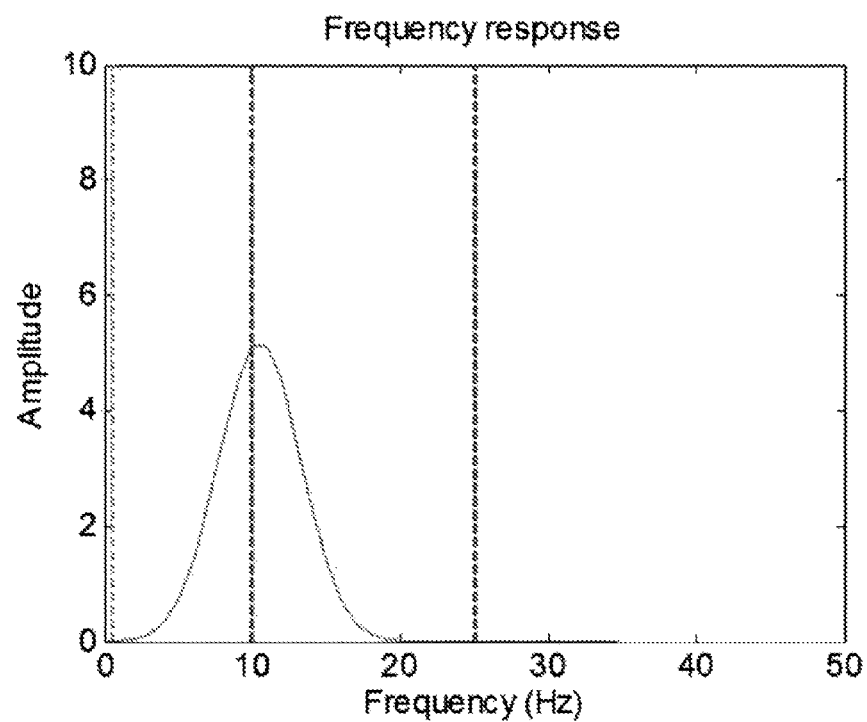
Figure 25J:
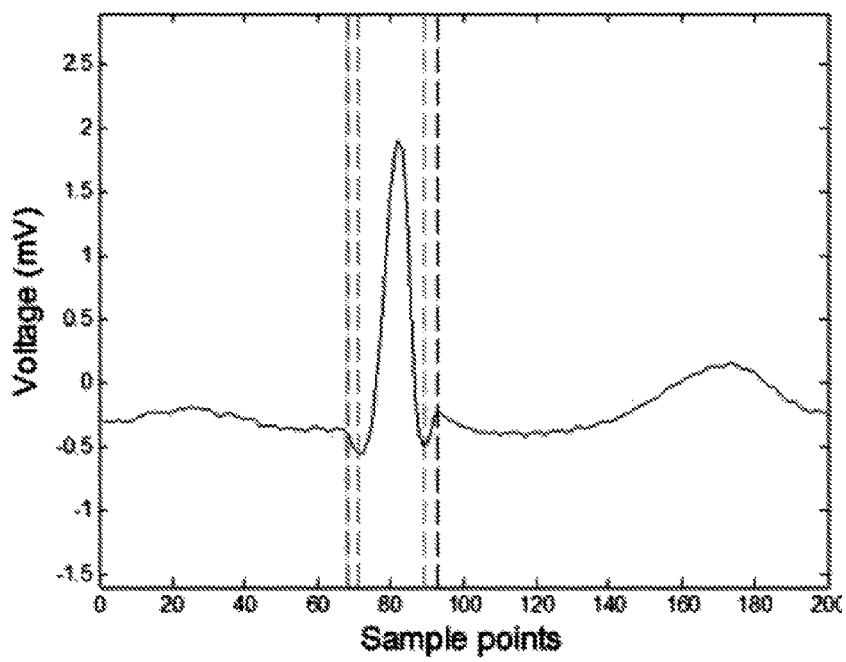
Figure 25K:
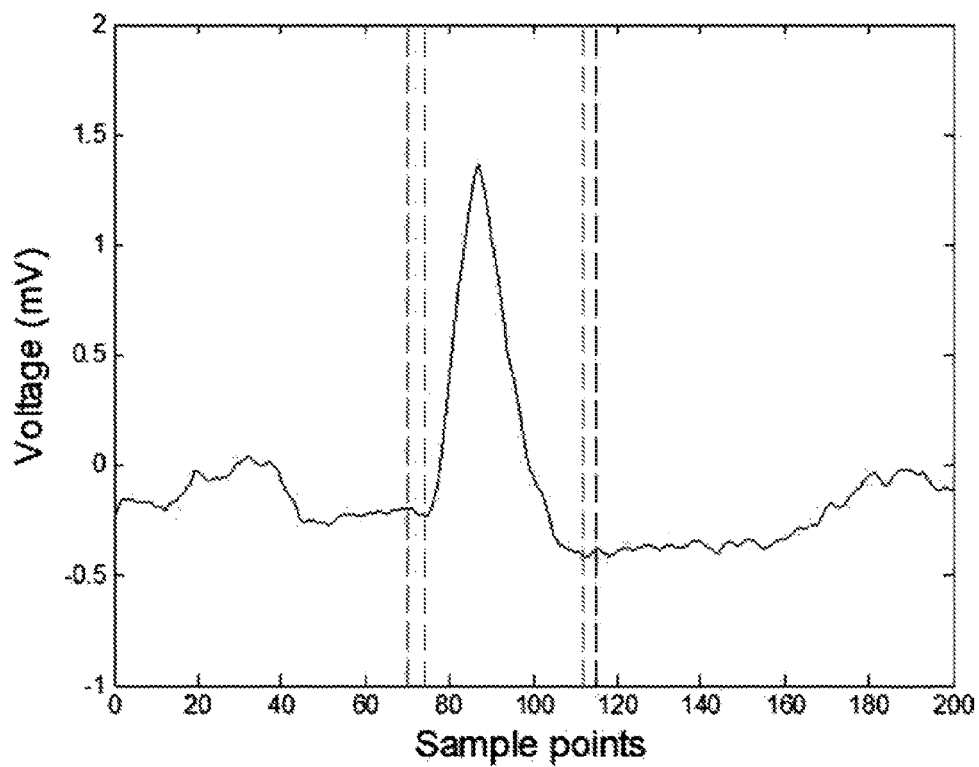
Figure 25L:
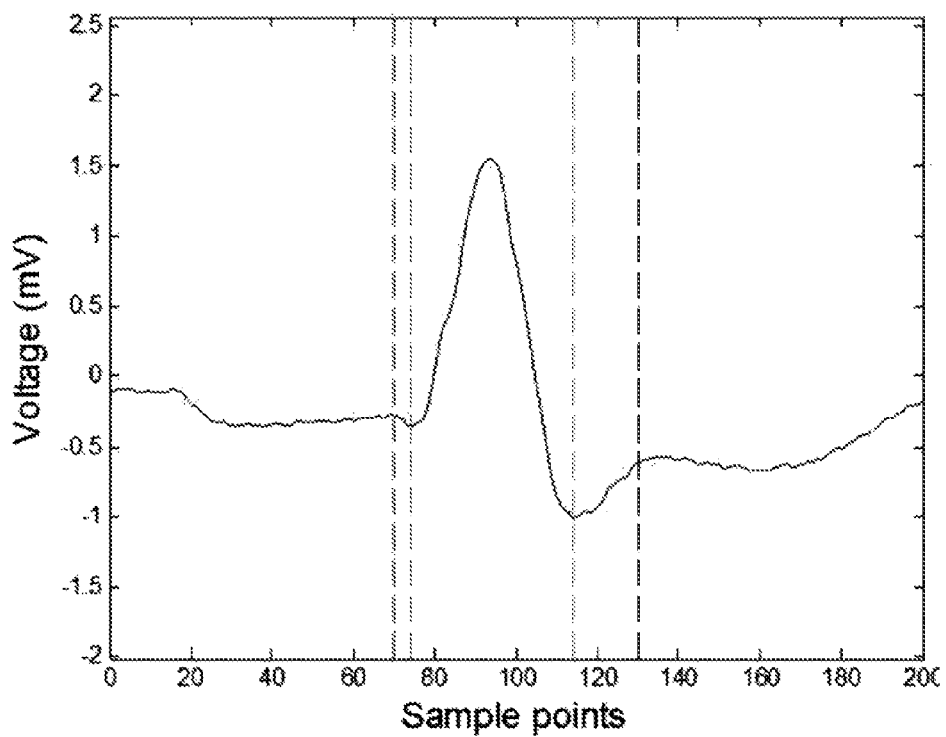

Based on the discussion, the criterion of determining which scale in CWT may be suitable for which duration of QRS complex is decided by the slope of QR and RS. FIGS. 25a, 25b and 25c show the slopes of QR and RS in different durations of QRS complex. The arrows depict the trend of slopes of QR and RS in the corresponding QRS complex. The duration of QRS complex is inversely proportional to the absolute value of the slope. In other words, shorter duration of the QRS complex corresponds to a higher absolute value of the slope. Next, there are three horizontal lines in each of the FIGS. 24a, 24b and 24c. The upper horizontal line represents the location of the R peak, and the left horizontal line may be determined by a few points on the left side of the R peak. Similarly, the right horizontal line may be determined by a few points on the right side of the R peak. In addition, the actual points may be determined by the sampling frequency of the ECG signals. FIGS. 25d, 25e and 25f show the results of the scalogram on FIGS. 25a, 25b and 25c. The responses of FIGS. 25d, 25e and 25f are different since the frequency of different durations of the QRS complex in FIGS. 25a, 25b and 25c are also not equal. This is a reason why selecting suitable scale for Q, S peak, and QRSon, QRSoff detections. The horizontal dotted line in FIGS. 25d, 25e and 25f is the selected scale in the ECG signal extraction method, and the corresponding bandwidths are shown in FIGS. 25g, 25h and 25i. The corresponding experimental results are then shown in FIGS. 25j, 25k and 25l.

Furthermore, a reason why the number of the selected scales is three will be discussed. It is a tradeoff among classification, accuracy and complexity. If the number of the selected scales is less than three, some durations of QRS complex may be missed in the detections. As a result, the accuracy of the features within QRS complex detection may be very low. However, if the number of the selected scales is larger than three, the accuracy may be higher in theory. In practice, it will increase the difficulty in classification since the larger the number the classes are to be classified the lower the accuracy in the classification process. It increases not only the difficulty in classification but also the algorithm complexity. The larger the number the classes are to be classified, the higher complexity the algorithm result is resulted. Based on these reasons, the number of the selected scales for QRS complex detections may be defined as three.

Embodiment of ECG Signal Extraction for P, T Peak

In the following sections, the P, T peak detections are discussed. In general, the frequency of P wave is lower than QRS complex, and T wave is lower than P wave. Hence, after CWT with Gabor mother wavelet, the selected scales for P peak detection may be larger than the scales used in QRS complex detection, and the selected scales for T peak detection may be larger than the scale used in the P peak detection.

Figure 26A:
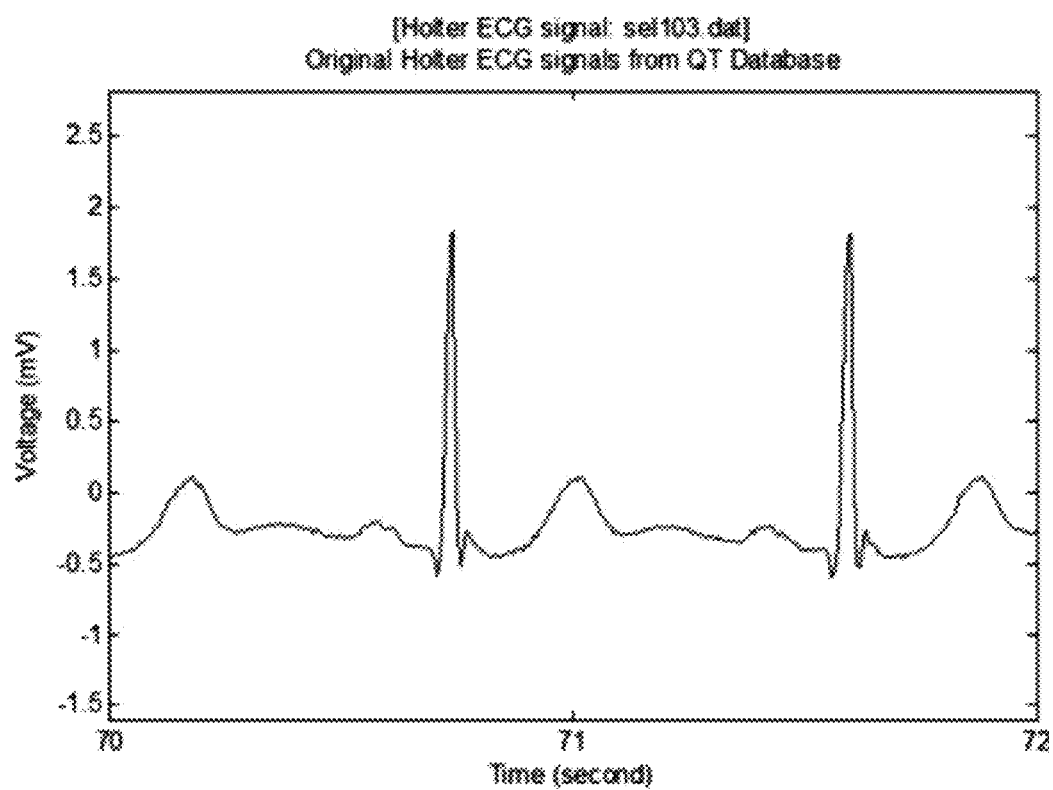
FIG. 26a-26h show the steps and experimental results of the P, T peak detections.
Figure 26B:
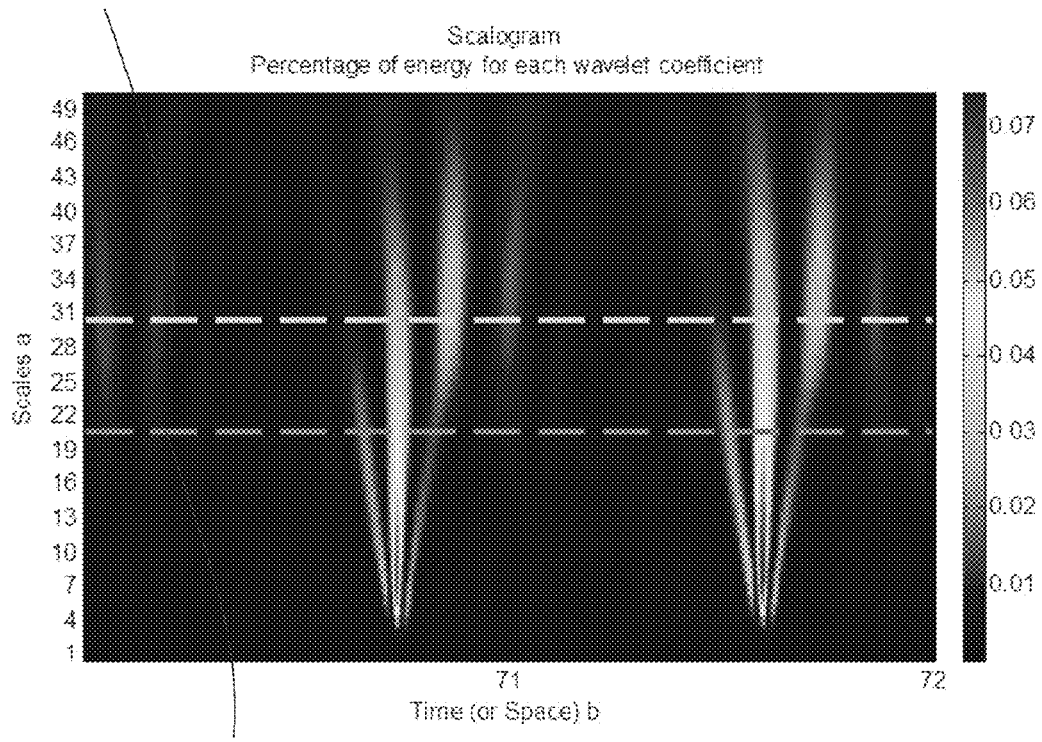
Figure 26C:
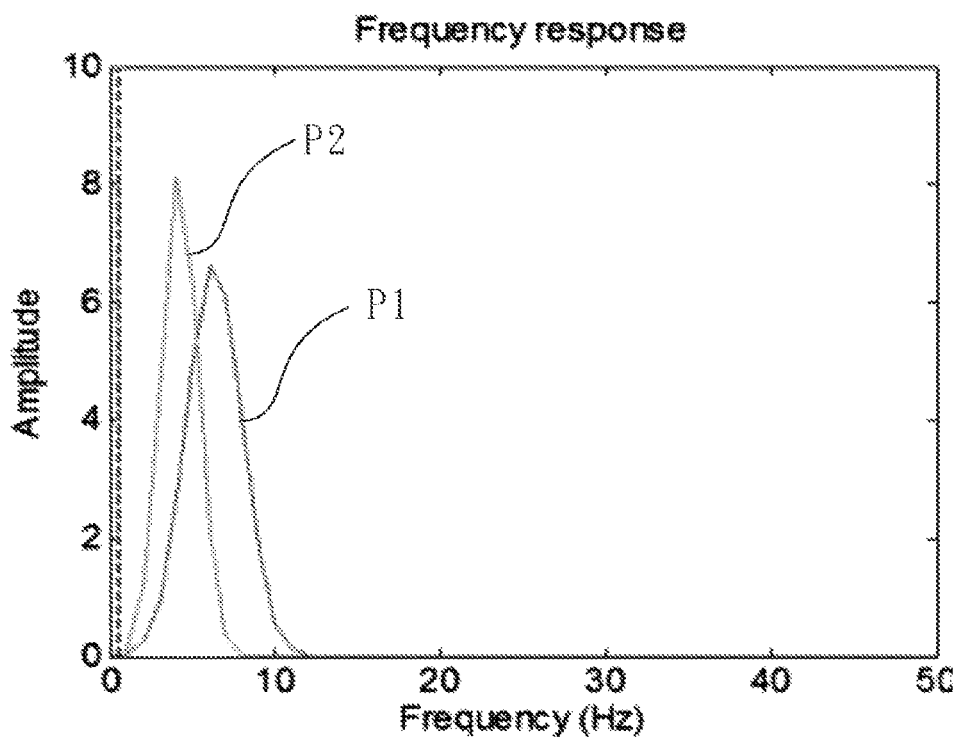
Figure 26D:
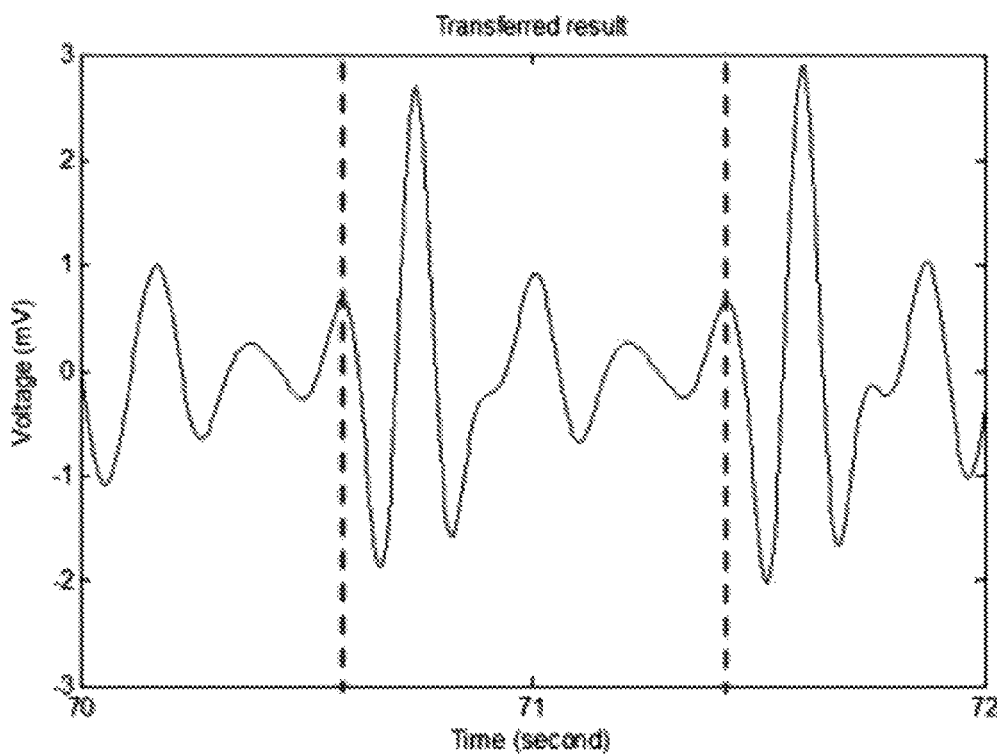
Figure 26E:
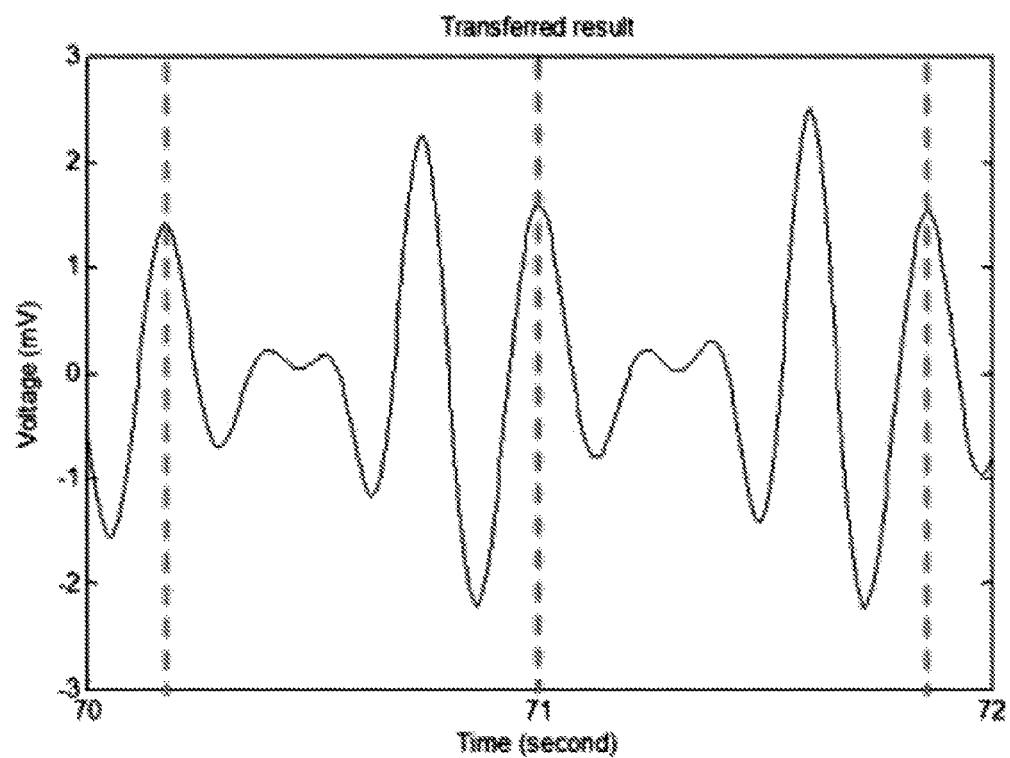
Figure 26F:
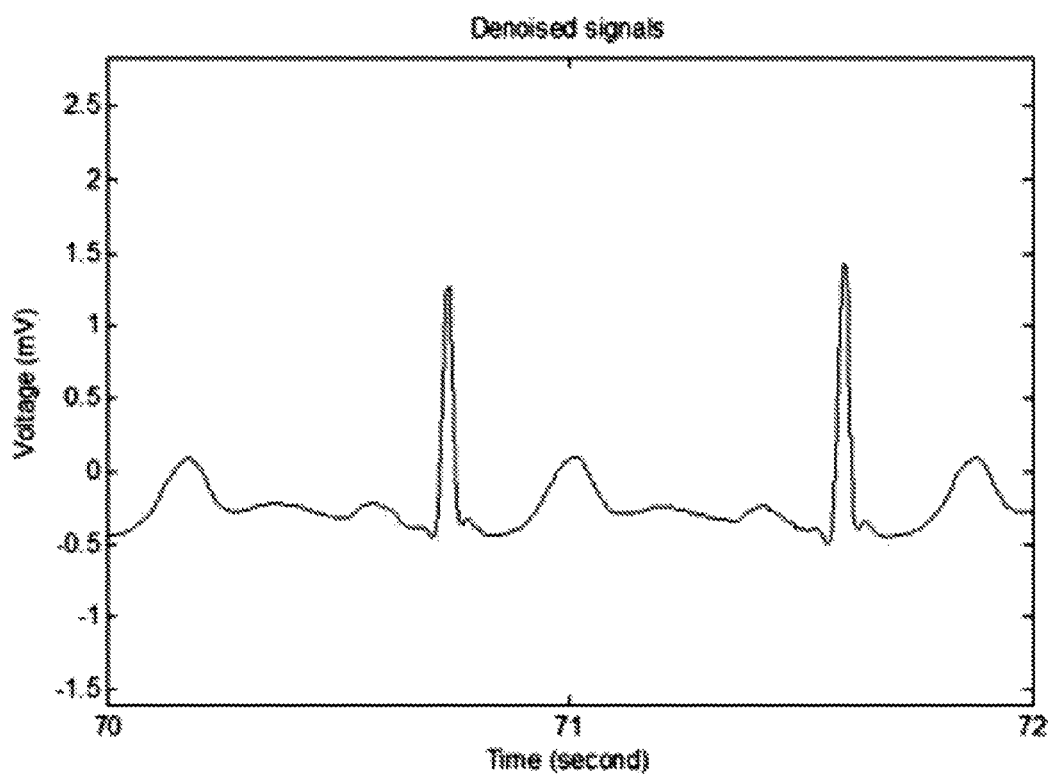
Figure 26G:
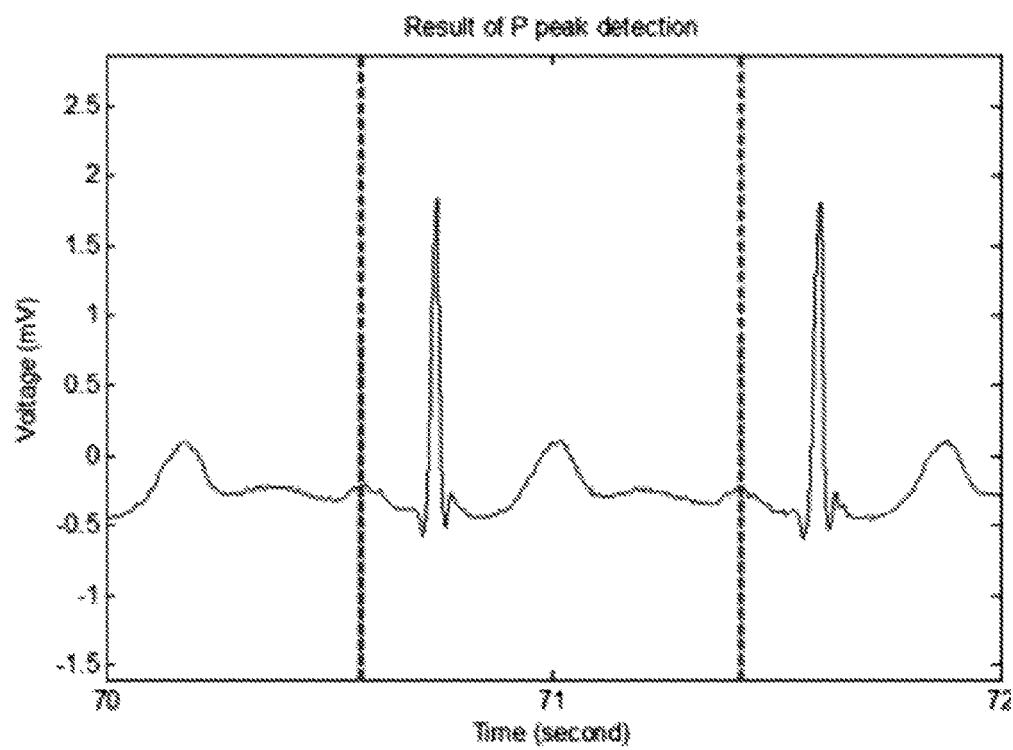
Figure 26H:
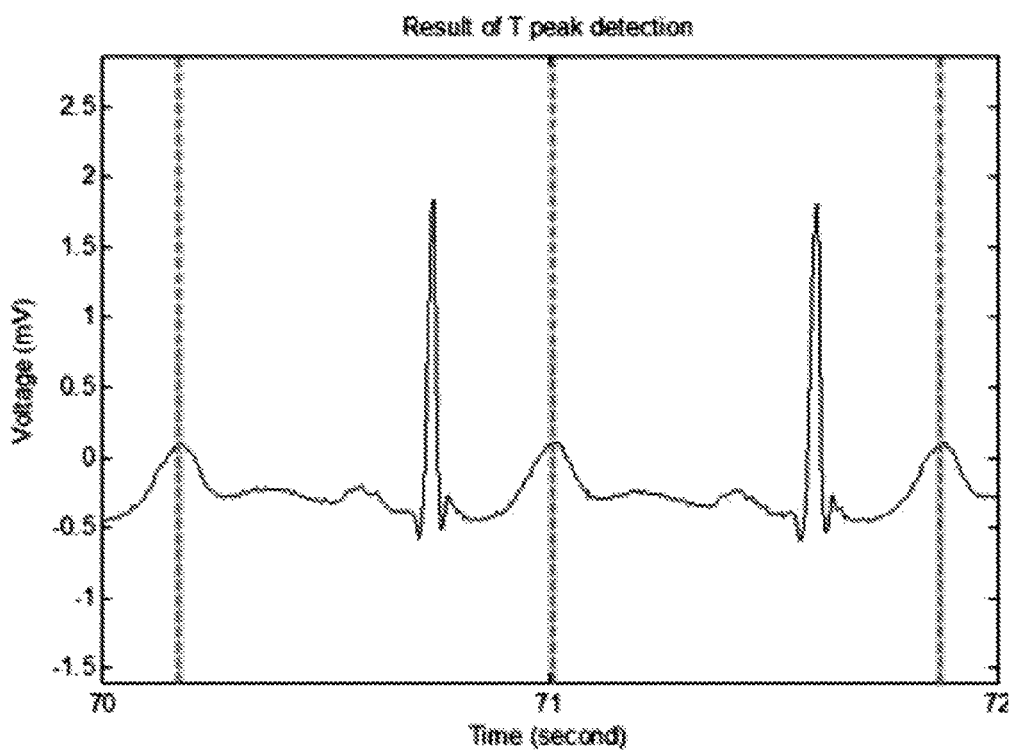

FIGS. 26a-26h show the steps and experimental results of the P, T peak detections. FIG. 26a shows the original ECG signals. FIG. 26b shows the scalogram of CWT with Gabor mother wavelet. The horizontal dotted line A4 indicates the selected scale for the P peak detection, and the horizontal dotted line A5 indicates the selected scale for the T peak detection. The criterion of selecting the scales in the P peak and T peak detections depends on the similarity between each wave in the ECG signals and the corresponding bases as well as the sampling frequency of the ECG signals. The parts P1 and P2 of the waves in FIG. 26c are the pass bands of the selected scales for the P and T peak detections in FIG. 26b, respectively. In FIGS. 26b and 26c, a predefined P-pertinent scale can be selected (line A4). Subsequently, FIGS. 26d and 26e show the transferred response of the selected scales for the P and T peak detections in FIG. 26b, respectively. The response of the P wave is enhanced in FIG. 26d, and the response of the T wave is enhanced in FIG. 26e. Namely, FIG. 26d is the P-pertinent transferred response generated by performing the time-frequency transformation on the selected predefined P-pertinent scale. The rough position of the P peaks depicted by the vertical dotted lines in FIG. 26d can be extracted by finding the position of the first maximum voltage before the corresponding R peak. Similarly, the rough position of the T peaks depicted by the vertical dotted lines in FIG. 26e can be extracted by finding the position of the first maximum voltage behind the corresponding R peak in FIG. 26e. Namely, the T-pertinent transferred response is generated by performing the time-frequency transformation on the selected pre-defined T-pertinent scale. Finally, the actual positions of the P, T peaks can be found on the de-noised signals instead of the original signals since the high frequency noise will affect the detected results. The de-noising step is alpha-trimmed mean filter, which has an adequate performance in reducing the combination of multiple types of noises. This advantage may be useful for processing the ECG signal since the ECG signals are obtained by different monitors. Hence, it is difficult to predict the noise model. FIG. 26f shows the de-noised result by the alpha-trimmed mean filter. Finally, based on the rough positions in FIGS. 26d and 26e, P peaks and T peaks are the positions having the corresponding maximum voltages in the de-noised signals. FIGS. 26g and 26h are the results of the P peaks and T peak detections, respectively. Namely, in FIG. 26g, P peak positions may be determined as being located at relative maximum response before the R peak positions. Similarly, in FIG. 26h, T peak positions may be determined as being located at relative maximum response behind the R peak positions.

In the following section, the Pon, Poff, Ton and Toff detections are discussed. As described previously, P wave and T wave can be viewed as Gaussian like waves. Different standard deviations (scales) of the Gaussian function represent various durations of the windows. Hence, based on the information above, the Pon, Poff, Ton, Toff detections may be performed using different scales of the Gaussian function to estimate the durations of the P wave and T wave. Then, the positions of Pon, Poff, Ton, Toff may be extracted based on the durations of the P wave and T wave. This mechanism is called matching process using Gaussian models with various scales (MPGMVS).

Figure 27A:
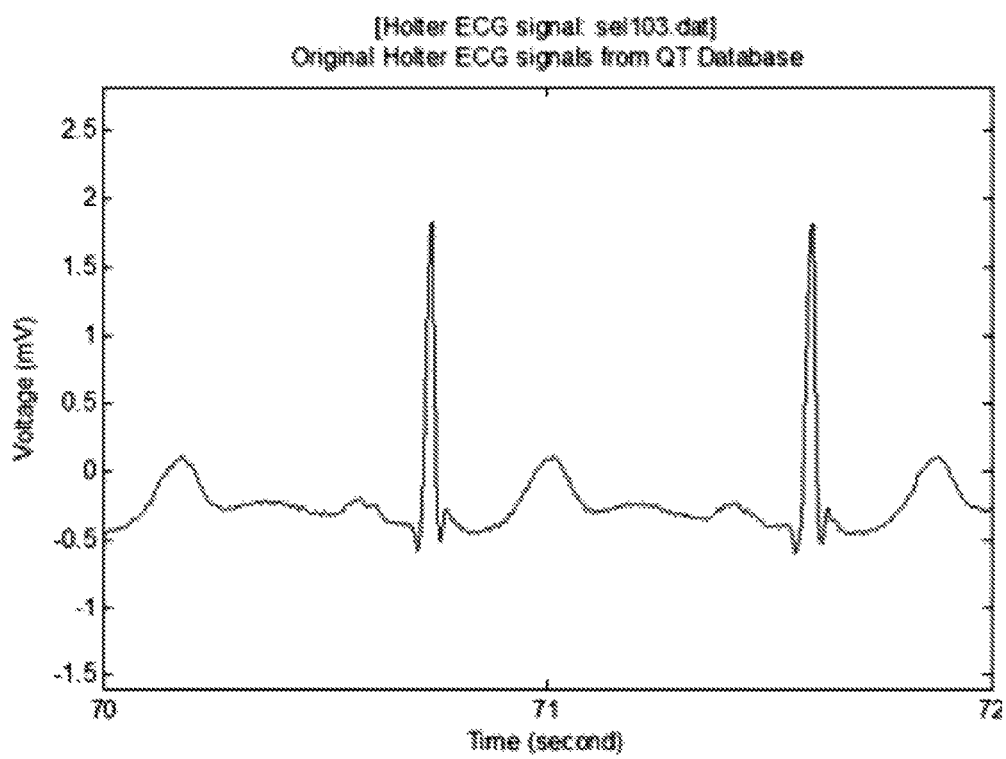
FIGS. 27a and 27b shows the steps and experimental results of the Pon, Poff, Ton, Toff detections.
Figure 27B:
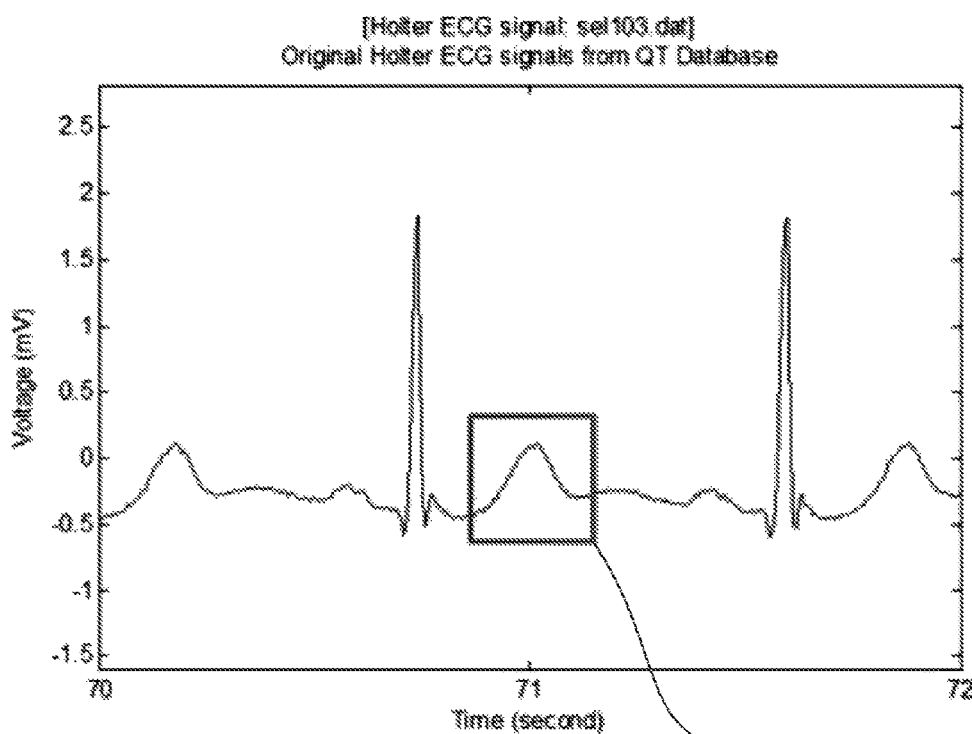
Figure 27C:
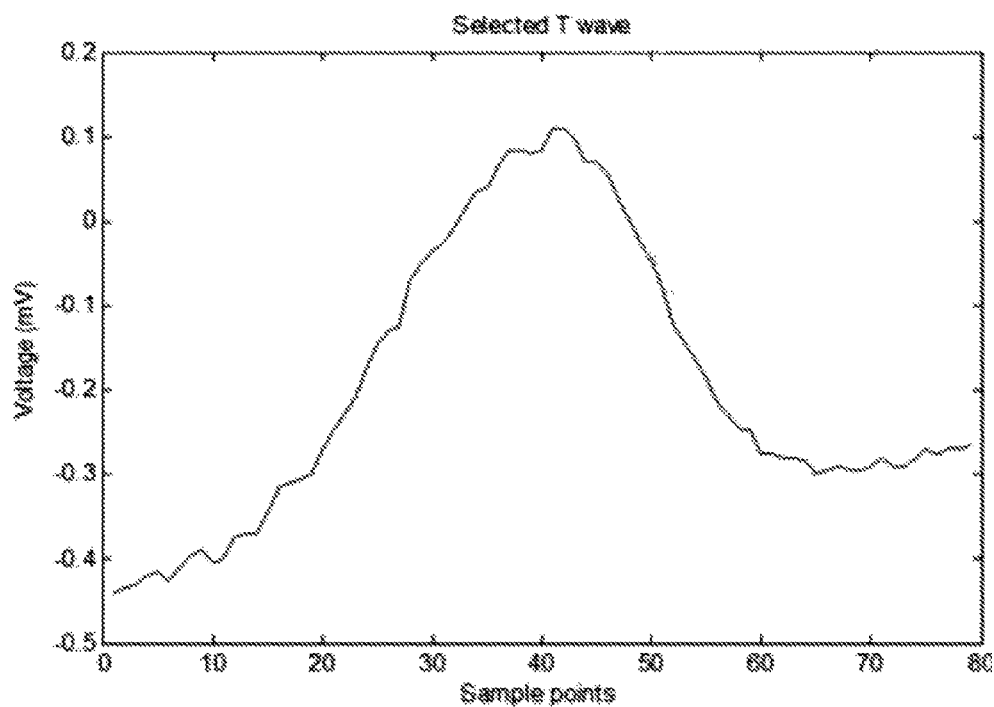
FIG. 27c shows an original T wave.
Figure 27D:
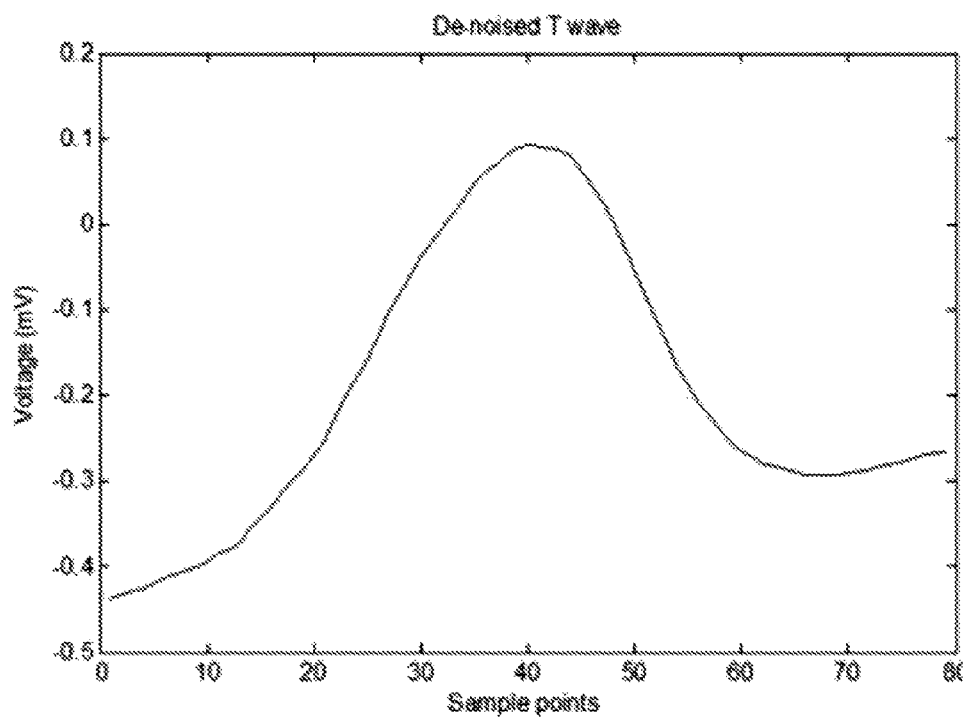
FIG. 27d is the de-noised result of the T wave in FIG. 27c.

FIGS. 27a and 27b show the steps and experimental results of the Pon, Poff, Ton, Toff detections. FIG. 27a depicts the originals signals. The T wave within block B3 in FIG. 27b is an example for Ton and Toff detections, and Pon, Poff could be detected in the same manner. Namely, in FIG. 27b, the T wave of the ECG signal is detected. The location of block B3 depends on the position of the T peak. FIG. 27c is the original T wave. What is noted is there exists some noise on the T wave, which will affect the results of the Ton and Toff detections. In light of this, noise reduction mechanism may be employed using the de-noised mechanism used in the P, T peak detections, e.g. de-noising the wave (S20). FIG. 27d is the de-noised result of the T wave in FIG. 27c.

Figure 27E:
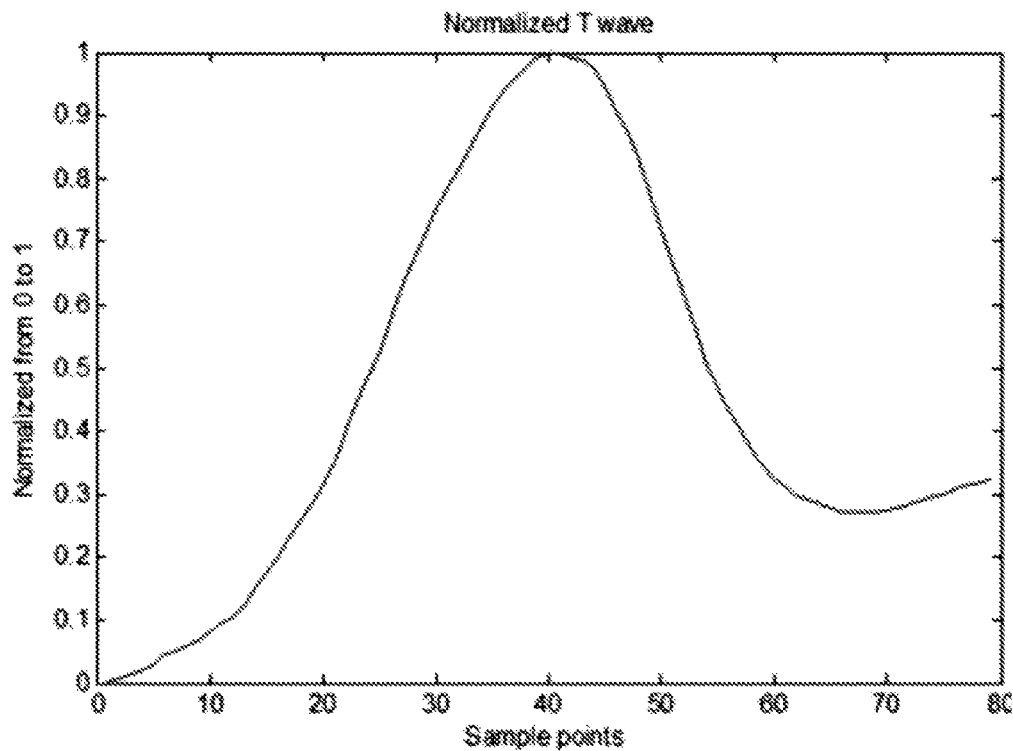
FIGS. 27e and 27f show the results of the normalized T wave and various scales of Gaussian, respectively.
Figure 27F:
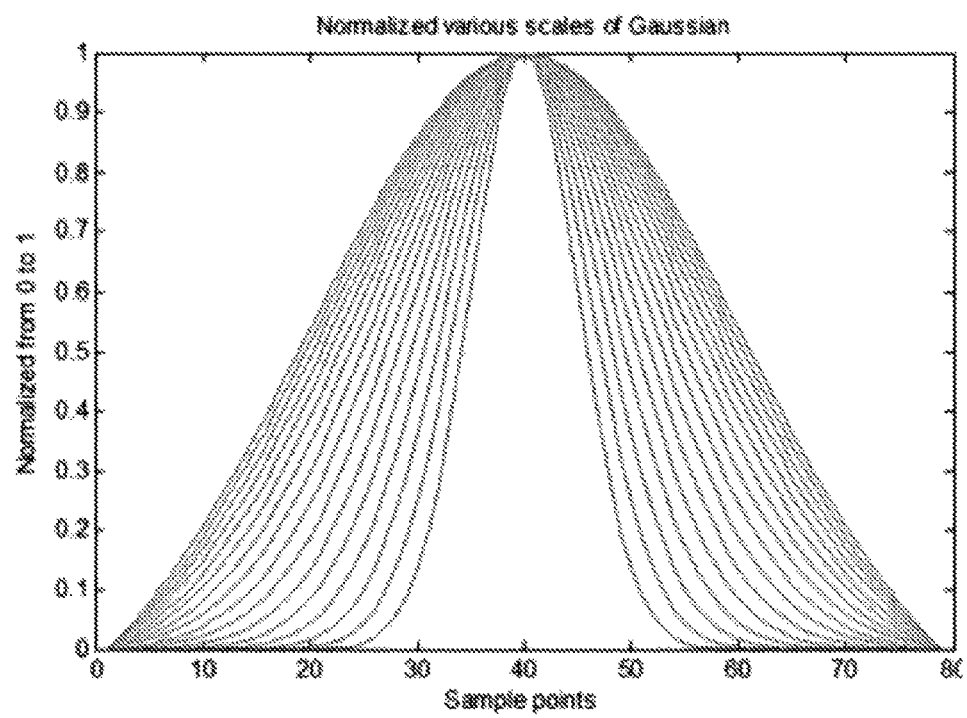

Then, the amplitudes among various T waves are almost different and the amplitudes among various scales of Gaussian are also different. Therefore, normalization on T wave and various scales of Gaussian may be better tasks, e.g. normalizing the left/right wave (S31/S32). FIGS. 27e and 27f show the results of the normalized T wave and various scales of Gaussian, respectively. However, there still exists an issue for the matching process between the de-noised normalized T wave and normalized various scales of Gaussian. The end of the right part of the de-noised normalized T wave in FIG. 27*e* is not the same as the start of the left part of the de-noised normalized T wave in FIG. 27*e*. To the contrary, symmetric Gaussian does not exist such is problem like FIG. 27*f*, namely symmetric Gaussian does not exist as is the problem rendered in FIG. 27*f*. The issue is caused by the baseline drift. Baseline drift not only causes the baseline to be located on a non-zero line but also results in an inequality between the onset and offset voltages. In order to solve this problem, the matching process may be divided by left part and right part based on the position of the T peak, so that Ton and Toff can be detected separately, e.g. a left extraction step and a right extraction step.

Figure 27G:
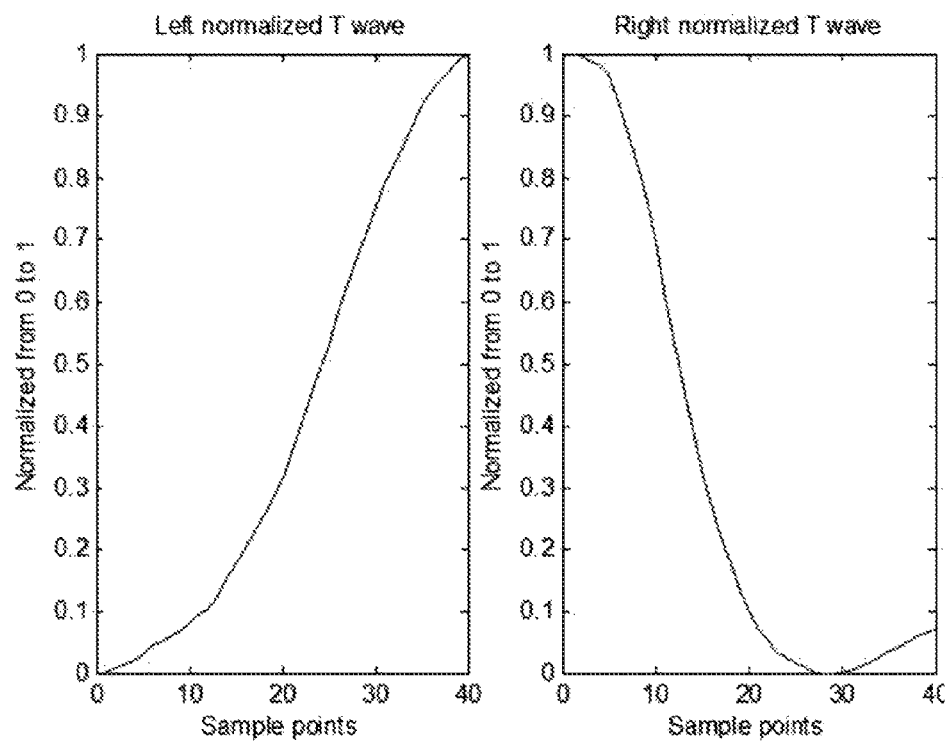
FIG. 27g shows the normalized results of the left and right parts of the T wave.
Figure 27H:
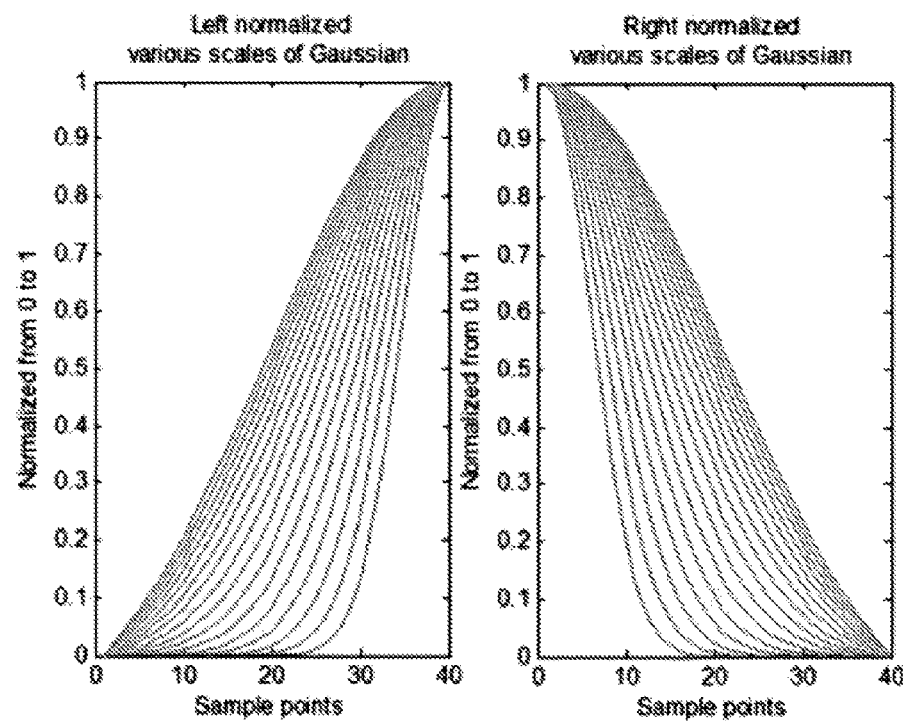
FIG. 27h shows the various scales of Gaussian being separated into left part and right part.

FIG. 27*g* shows the normalized results of the left and right parts of the T wave. It is observed that the effect of the baseline drift does not affect the Ton and Toff detections. Namely, what is shown in FIG. 27*g* is the T wave being separated into left and right waves and being normalized (the same can be applied to P wave). Since the matching process may be performed separately, it may be also needed to separate the entire various scales of Gaussian into left part and right part as shown in FIG. 27*h*. Subsequently, the left part and right part of the normalized T waves are compared with the left part and right part of various scales of Gaussians, respectively, e.g. comparing the normalized left wave with the left/right part of the plurality of scales of Gaussian.

Figure 27I:
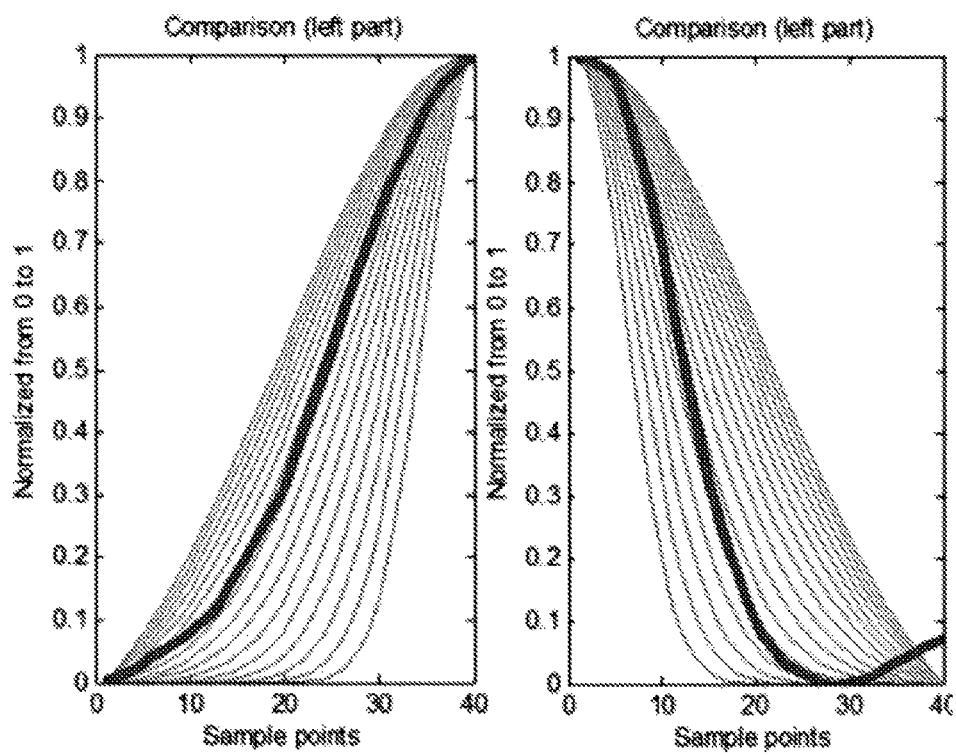
FIG. 27i shows the comparison between FIGS. 27g and 27h.
Figure 27J:
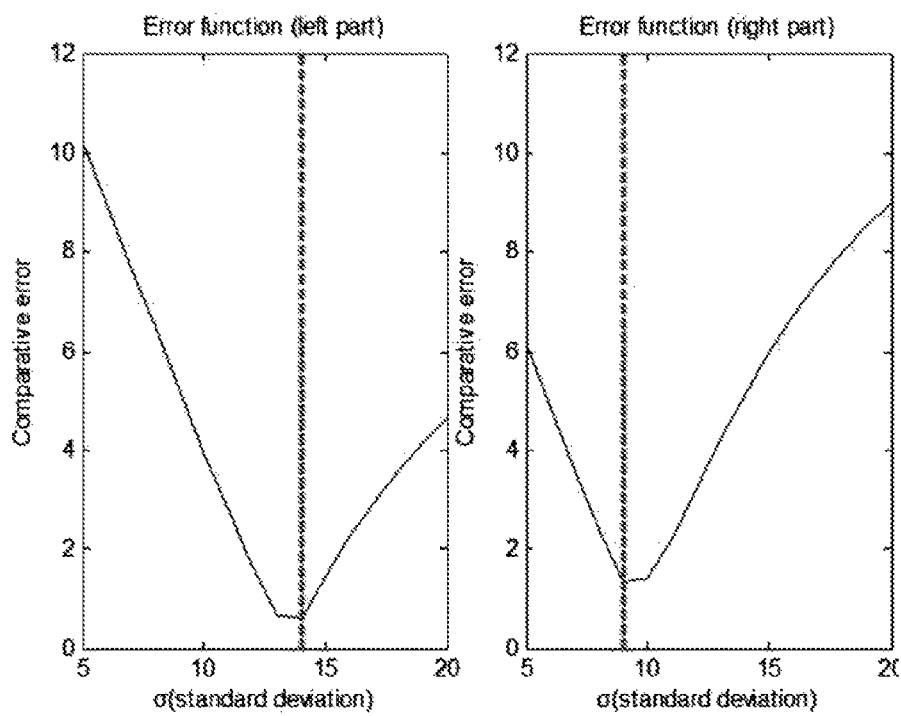
FIG. 27j shows the left part and right part of comparative error functions.

The corresponding step is shown in FIG. 27*i*. In FIG. 27*i*, the normalized left wave of the T wave is compared with a left part of various scales of Gaussian (the same can be applied to P wave). Then, FIG. 27*j* shows the left part and right part of comparative error functions of the T wave, e.g. acquiring the left/right part error function (the same can be applied to P waves). The horizontal axis is the various standard deviations (scales). The vertical axis is the comparative error with various scales. The vertical dotted line indicates the scale with minimum comparative error in the left and right parts of FIG. 27*j* which bears the scales with left and right minimum comparative errors, and proper scales of Gaussian for the left and right parts of the T wave are extracted, e.g. indicating the left minimum comparative error.

Figure 27K:
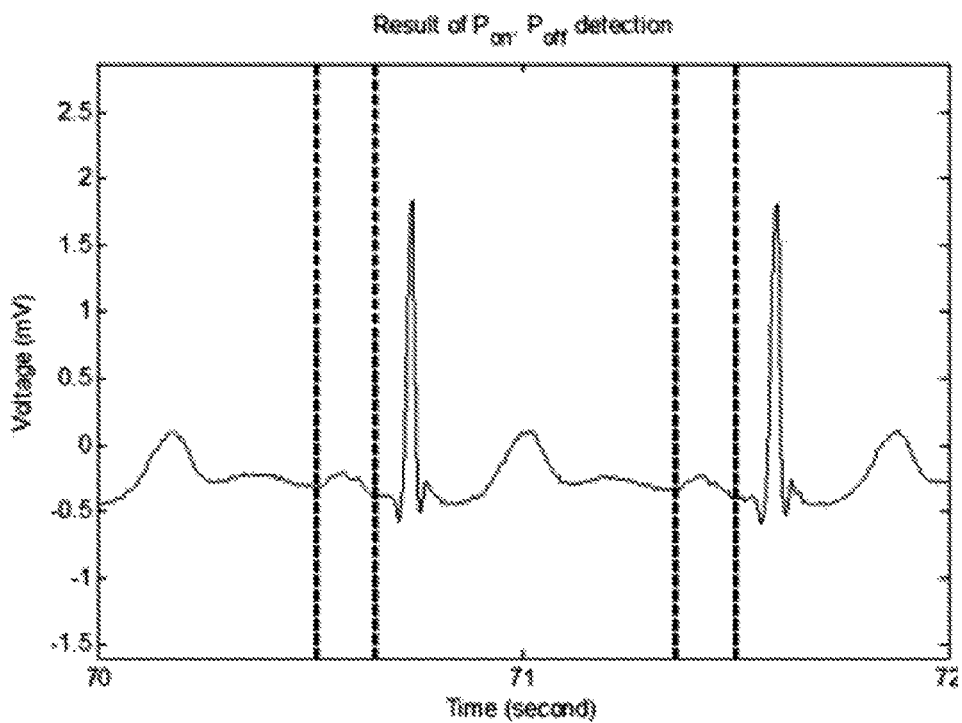
FIGS. 27k and 27l show the experimental results of the Pon, Poff and Ton, Toff detections, respectively.
Figure 27L:
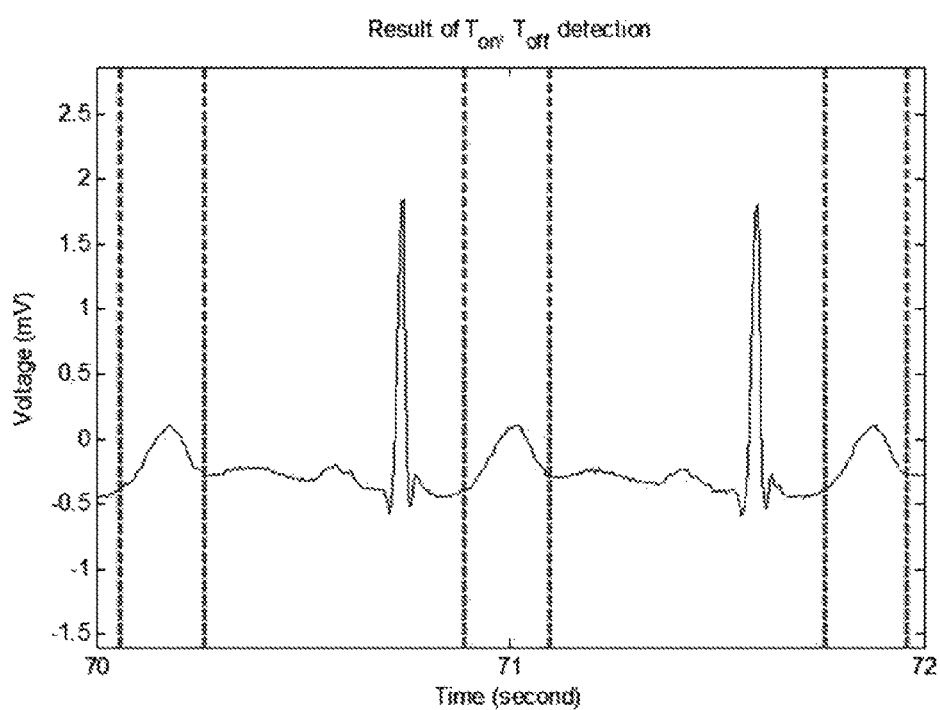

Finally, the durations of the left and right parts of the T wave can be obtained by the extracted scales of Gaussian, e.g. selecting the left/right scale of Gaussian with the left minimum comparative error and obtaining the left duration of the wave according to the selected left/right scale of Gaussian. The positions of Ton and Toff can be detected by the position of the T peak as well as the left and right durations of the T waves. Similarly, the positions of Pon and Poff can also be detected. FIGS. 27*k* and 27*l* show the experimental results of the Pon, Poff and Ton, Toff detections, respectively. In FIG. 27*k*, the left duration of the P wave can be obtained according to the selected left scale of Gaussian, and Pon can be obtained by the left duration of the T wave. Also, the right duration of the P wave can be obtained according to the selected right scale of Gaussian, and Poff can be obtained by the right duration of the P wave. In FIG. 27*l*, the left duration of the T wave can be obtained according to the selected left scale of Gaussian, and Ton can be obtained by the left duration of the T wave. Also, the right duration of the T wave can be obtained according to the selected right scale of Gaussian, and Toff can be obtained by the right duration of the T wave.

Embodiment of ECG Signal Extraction for Amplitudes and Depths

Figure 28:
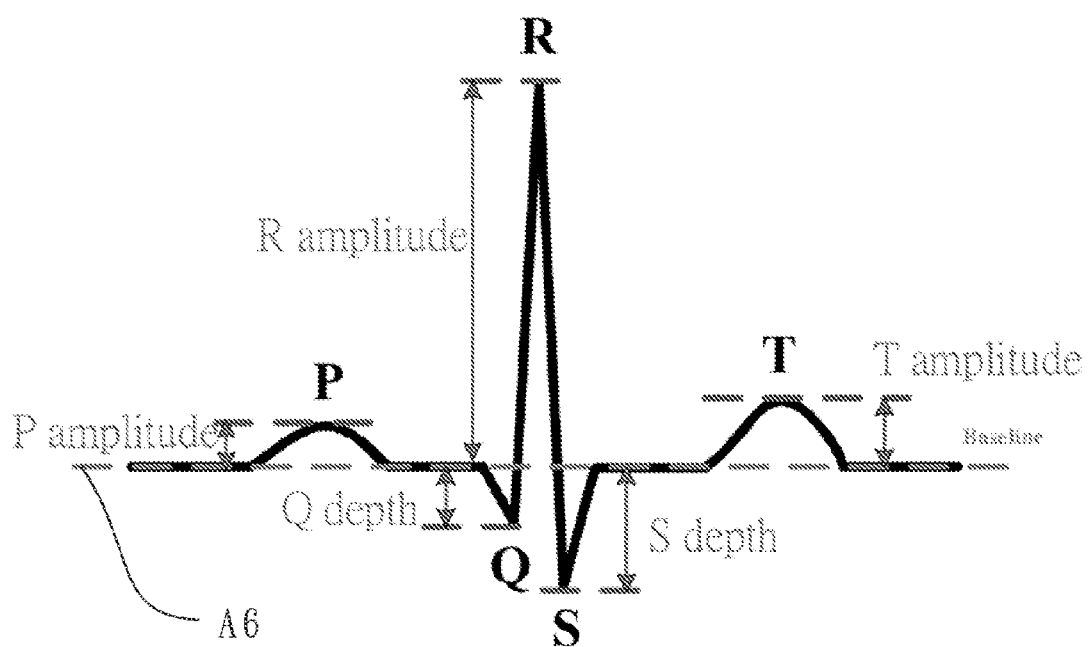
FIG. 28 shows the clinically useful amplitude and depth information.

In the following sections, the amplitude and depth estimations are discussed. The clinically useful amplitude and depth information is shown in FIG. 28. For the amplitude estimation, there are P amplitude, R amplitude and T amplitude. For the depth estimation, there are Q depth and S depth. In FIG. 28, R amplitude can be calculated by determining a difference between the R peak and a linear interpolation line connected between the QRSon and QRSoff positions. In this regard, the Q depth can be calculated by determining a difference between the Q peak and the QRSon, and the S depth can be calculated by determining a difference between the Q peak and the QRSoff.

The horizontal dotted line A6 in FIG. 28 is an ideal baseline having a voltage of zero. In addition, the positions of all onsets and offsets are on the ideal baseline. However, in practice, there exists the issue of baseline drift. As described previously, the baseline drift not only causes the baseline to be located on a non-zero line but also results in an inequality between the onset and offset voltages. As a result, the voltage value of each peak may be not reliable and the voltage difference between the peak and the onset/offset are incorrect. Therefore, the present embodiment for amplitude and depth estimations will calculate the voltage difference among the peak, the onset and the offset.

Figure 29A:
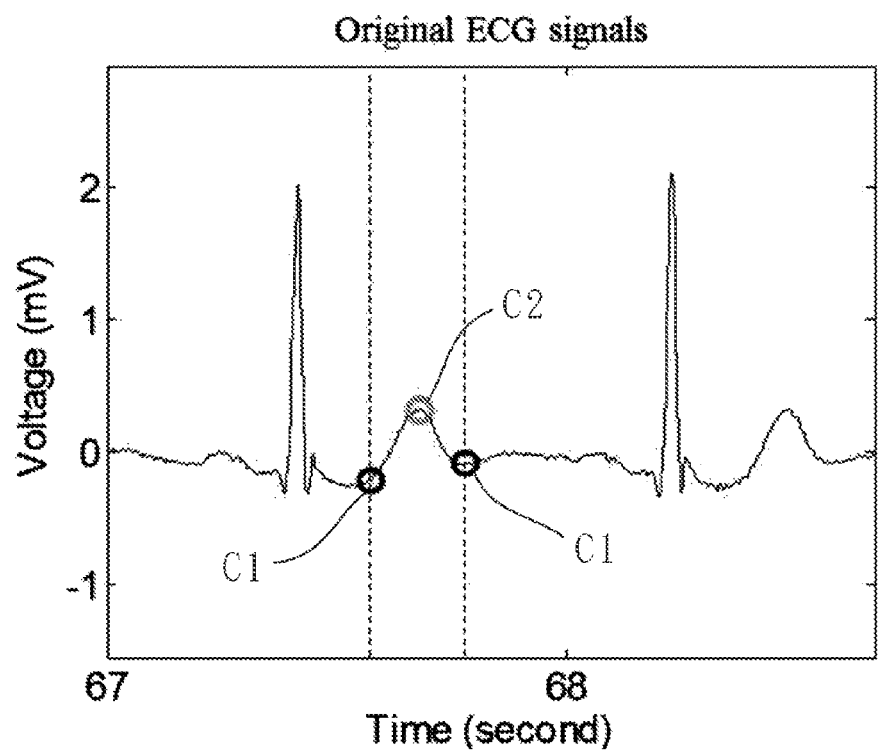
FIG. 29a is the original ECG signals, with two black circles indicate Ton and Toff, with the circle indicates the T peak, with the green circle point indicates the position of the T peak projected on the purple oblique line which is combined by Ton and Toff in FIG. 29b.
Figure 29B:
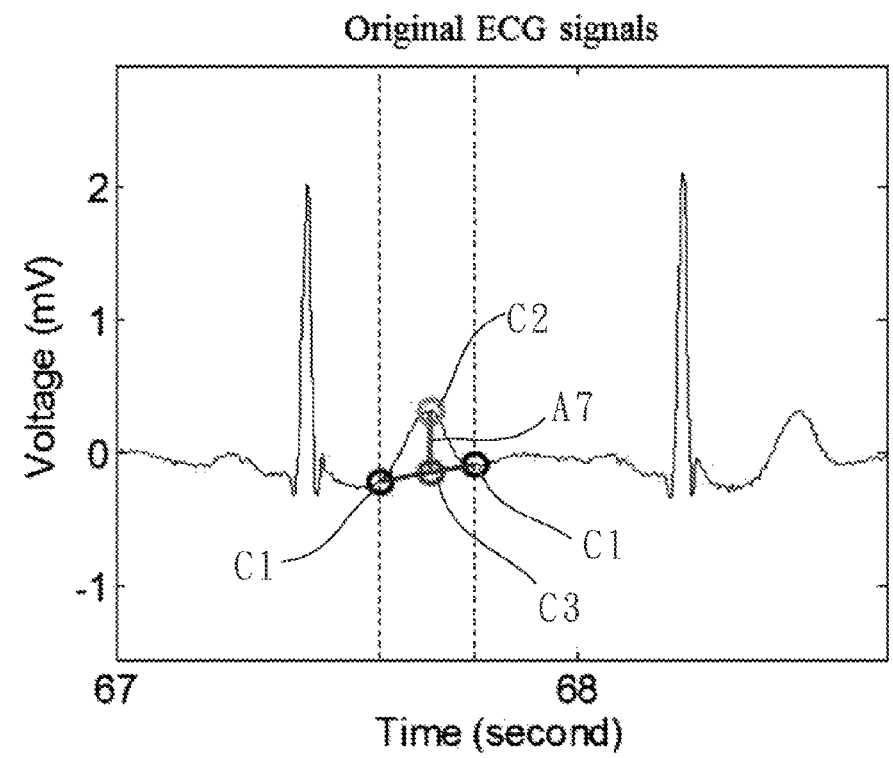

The T amplitude estimation is an example for illustrating the concept. FIG. 29*a* is the original ECG signals. The positions of the two circles C1 indicate Ton and Toff. The position of the circle C2 indicates the T peak. The position of the circle point C3 indicates the position of the T peak projected on the purple oblique line which is combined by Ton and Toff in FIG. 29*b*. Finally, the length of the vertical line A7 obtained from the voltage difference between the circle point C2 and the circle point C3 indicates the estimated T amplitude. Similarly, the P amplitude estimation calculates the voltage difference among the P peak, Pon, and Poff. Thus, the T amplitude can be calculated by determining a difference between the T peak and a linear interpolation line connected between Ton and Toff (the same can be applied to P amplitude). The R amplitude estimation may calculate the voltage difference among the R peak, QRSon and QRSoff. The Q depth estimation calculates the voltage difference between the Q peak and QRSon. The S depth estimation may calculate the voltage difference between the S peak and QRSoff.

The databases used in the embodiment for experiments are MIH-BIH arrhythmia database (MITDB) and QT Database (QTDB). In the MITDB, there are 48 records, and each record contains 2-lead 30 minutes. There exists about 110 thousand annotated beats in MITDB. Without including the normal beat and the unclassifiable beat, MITDB contains 15 different types of arrhythmia. Therefore, MITDB may be the most popular database to assess the accuracy in feature extraction and the classification in the ECG signal processing. Besides, in QTDB, there are 105 records from a lot of databases. In addition, the ECG signal extraction method of the disclosure may be executed by a processor of a computer system along with a necessary database described above.

Although the invention has been described in detail with reference to its presently preferable embodiments, it will be understood by one of ordinary skill in the art that various modifications can be made without departing from the spirit and the scope of the invention, as set forth in the appended claims.

What is claimed is:

1. An electrocardiography signal extraction method, the electrocardiography signal extraction method being performed on a processor of a ECG-signal-extracting computer system, the electrocardiography signal extraction method comprising:

receiving an electrocardiography signal by the processor of the computer system;

performing a time-frequency transformation on the received electrocardiography signal to generate a corresponding scalogram;

selecting a predetermined R-pertinent scale for the corresponding scalogram;

performing the time-frequency transformation on the corresponding scalogram at the selected predetermined R-pertinent scale to generate a R-pertinent summarized response;

obtaining a R peak position of the electrocardiography signal by finding maximum responses on the R-pertinent summarized response;

selecting a predetermined QRS-pertinent scale for the corresponding scalogram;

performing the time-frequency transformation on the corresponding scalogram at the selected predetermined QRS-pertinent scale to generate a QRS-pertinent transferred response;

obtaining a Q peak position of the electrocardiography signal by finding relative maximum negative responses before the R peak position;

obtaining a S peak position of the electrocardiography signal by finding relative maximum negative responses behind the R peak position;

obtaining a QRSon position of the electrocardiography signal by finding relative minimum second derivatives of the responses before the Q peak position;

obtaining a QRSoff position of the electrocardiography signal by finding relative minimum second derivatives of the responses behind the S peak position; and outputting the R peak position, the Q peak position, the S peak position, the QRSon position, and the QRSoff position from the ECG-signal-extracting computer system to a machine or a medium.

2. The electrocardiography signal extraction method as claimed in claim 1, wherein the time-frequency transformation comprises Continuous Wavelet Transform with Gabor mother wavelet.

3. The electrocardiography signal extraction method as claimed in claim 1, wherein the predetermined R-pertinent scale comprises three predetermined R-pertinent scales.

4. The electrocardiography signal extraction method as claimed in claim 1, further comprising:

de-noising the wave before performing the time-frequency transformation;

selecting a predetermined P-pertinent scale for the corresponding scalogram;

performing the time-frequency transformation on the corresponding scalogram at the selected predetermined P-pertinent scale to generate a P-pertinent transferred response;

obtaining a P peak position of the electrocardiography signal by finding relative maximum responses before the R peak position;

selecting a predetermined T-pertinent scale for the corresponding scalogram;

performing the time-frequency transformation on the corresponding scalogram at the selected predetermined T-pertinent scale to generate a T-pertinent summarized response;

obtaining a T peak position of the electrocardiography signal by finding relative maximum responses behind the R peak position; and outputting the P peak position and the T peak position by the processor.

5. The electrocardiography signal extraction method as claimed in claim 4, further comprising:

detecting a P wave of the electrocardiography signal by the P peak position;

separating the P wave into a left wave and a right wave;

normalizing the left wave and a plurality of scales of a Gaussian function;

comparing the normalized left wave with a left part of the normalized scales of the Gaussian function;

acquiring a left part error function;

indicating a left minimum comparative error;

selecting a left scale of the Gaussian function with the left minimum comparative error;

obtaining a left duration of the P wave according to the selected left scale of the Gaussian function;

obtaining a Pon by the left duration and the P peak position;

normalizing the right wave;

comparing the normalized right wave with a right part of the normalized scales of the Gaussian function;

acquiring a right part error function;

indicating a right minimum comparative error;

selecting a right scale of the Gaussian function with the right minimum comparative error;

obtaining a right duration of the P wave according to the selected right scale of the Gaussian function;

obtaining a Poff by the right duration and the P peak position; and obtaining an extracted P wave; and outputting the P extracted wave by the processor.

6. The electrocardiography signal extraction method as claimed in claim 5, further comprising:

estimating a P amplitude by calculating a difference between the P peak and a linear interpolation line connected between Pon and Poff; and outputting the P amplitude by the processor.

7. The electrocardiography signal extraction method as claimed in claim 4, further comprising:

detecting a T wave of the electrocardiography signal by the T peak position;

separating the T wave into a left wave and a right wave;

normalizing the left wave and a plurality of scales of the Gaussian function;

comparing the normalized left wave with a left part of the normalized scales of the Gaussian function;

acquiring a left part error function;

indicating a left minimum comparative error;

selecting a left scale of the Gaussian function with the left minimum comparative error;

obtaining a left duration of the T wave according to the selected left scale of the Gaussian function;

obtaining a Ton by the left duration and the T peak position;

normalizing the right wave;

comparing the normalized right wave with a right part of the normalized scales of the Gaussian function;

acquiring a right part error function;

indicating a right minimum comparative error;

selecting a right scale of the Gaussian function with the right minimum comparative error;

obtaining a right duration of the T wave according to the selected right scale of the Gaussian function;

obtaining a Toff by the right duration and the T peak position;

obtaining an extracted T wave; and outputting the extracted T wave by the processor.

8. The electrocardiography signal extraction method as claimed in claim 7, further comprising:

estimating a T amplitude by calculating a difference between the T peak and a linear interpolation line connected between Ton and Toff; and outputting the T amplitude by the processor.

9. The electrocardiography signal extraction method as claimed in claim 1, further comprising de-noising the wave before performing the time-frequency transformation.

10. The electrocardiography signal extraction method as claimed in claim 1, further comprising de-noising the wave after performing the time-frequency transformation.

11. The electrocardiography signal extraction method as claimed in claim 1, further comprising:

estimating a R amplitude by calculating a difference between the R peak and a linear interpolation line connected between the QRSon position and the QRSoff position;

estimating a Q depth by calculating a difference between the Q peak and QRSon;

estimating a S depth by calculating a difference between the Q peak and QRSoff; and outputting the R amplitude, the Q depth, and the S depth by the processor.

* * * * *